US010617353B2

(12) United States Patent
Tsamir et al.

(10) Patent No.: US 10,617,353 B2
(45) Date of Patent: Apr. 14, 2020

(54) IDENTIFYING A TARGET ANATOMIC LOCATION IN A SUBJECT'S BODY, AND DELIVERING A MEDICINAL SUBSTANCE THERETO

(71) Applicant: OMEQ MEDICAL LTD, M.P. Misgav (IL)

(72) Inventors: Oded Tsamir, Tel Aviv (IL); Lior Margalit, Tel Aviv (IL)

(73) Assignee: OMEQ MEDICAL LTD., M.P. Misgav (IL)

( * ) Notice: Subject to any disclaimer, the term of this patent is extended or adjusted under 35 U.S.C. 154(b) by 295 days.

(21) Appl. No.: 15/321,583

(22) PCT Filed: Jun. 23, 2015

(86) PCT No.: PCT/IB2015/054704
§ 371 (c)(1),
(2) Date: Dec. 22, 2016

(87) PCT Pub. No.: WO2015/198223
PCT Pub. Date: Dec. 30, 2015

(65) Prior Publication Data
US 2017/0231563 A1    Aug. 17, 2017

Related U.S. Application Data

(60) Provisional application No. 62/015,532, filed on Jun. 23, 2014.

(51) Int. Cl.
*A61B 5/00* (2006.01)
*A61B 17/34* (2006.01)
(Continued)

(52) U.S. Cl.
CPC .......... *A61B 5/4896* (2013.01); *A61B 5/0053* (2013.01); *A61B 5/6847* (2013.01);
(Continued)

(58) Field of Classification Search
CPC .............. A61B 5/4896; A61B 17/3401; A61B 17/3496; A61B 90/06; A61B 5/0053;
(Continued)

(56) References Cited

U.S. PATENT DOCUMENTS 4,535,773 A    8/1985    Yoon
5,146,921 A    9/1992    Terwilliger et al.
(Continued)

FOREIGN PATENT DOCUMENTS

CN    103281950 A    9/2013
GB    2446447    *    8/2008
(Continued)

OTHER PUBLICATIONS

Oct. 29, 2016 International Search Report for International Patent Application No. PCT/IB2015/054704.
(Continued)

*Primary Examiner* — Theodore J Stigell
(74) *Attorney, Agent, or Firm* — Pearl Cohen Zedek Latzer Baratz LLP

(57) ABSTRACT

Identifying target anatomic locations in a subject's body, and delivering medicinal substances thereto, following transtissual progression (penetrating, cutting through body tissue) and reaching body tissue with medical device distal tip. Involves acquiring mechanical properties of body tissue. Exemplary medicinal substance is, or includes, a drug (anesthetic agent), and exemplary target anatomic location is epidural space in subject's body. Exemplary system includes: cannular member enclosing cannula lumen; pusher-probe having distal end in cannula lumen and positionable from retracted to protruding positions, wherein
(Continued)

pusher-probe distal end protrudes out of cannula distal end; and extending mechanism including cam member, a follower shiftable from first to second stations on cam member, and plunger selectively traveling in cannula lumen while forcing relative motion between cam member and follower, wherein pusher-probe distal end repositions between retracted and protruding positions. Optionally, includes data-information analyzing device having triggering mechanism via a winged hub member and associated components.

30 Claims, 24 Drawing Sheets

(51) Int. Cl.
    *A61M 25/06*     (2006.01)
    *A61B 90/00*     (2016.01)
    *A61M 5/31*     (2006.01)
    *A61M 25/00*     (2006.01)
(52) U.S. Cl.
    CPC .......... *A61B 5/6848* (2013.01); *A61B 5/6885* (2013.01); *A61B 17/3401* (2013.01); *A61B 17/3496* (2013.01); *A61B 90/06* (2016.02); *A61M 5/31* (2013.01); *A61M 25/065* (2013.01); *A61B 2090/061* (2016.02); *A61B 2090/064* (2016.02); *A61M 2025/0007* (2013.01)
(58) Field of Classification Search
    CPC ................ A61B 5/6848; A61B 5/6885; A61B 2090/061; A61B 2090/064; A61B 5/6847; A61M 25/065; A61M 5/31; A61M 2025/0007

See application file for complete search history.

(56) References Cited

U.S. PATENT DOCUMENTS

| | | | |
|---|---|---|---|
| 5,685,852 A * | 11/1997 | Turkel | A61B 17/3401 604/159 |
| 8,920,388 B2 | 12/2014 | Slocum et al. | |
| 9,801,659 B2 * | 10/2017 | Okazaki | A61B 17/3478 |
| 2009/0093692 A1 | 4/2009 | Hansma | |
| 2012/0209303 A1 | 8/2012 | Frankhouser et al. | |
| 2013/0085413 A1 * | 4/2013 | Tsamir | A61B 5/0053 600/567 |

FOREIGN PATENT DOCUMENTS

| | | | |
|---|---|---|---|
| WO | 2011158227 | * | 12/2011 |
| WO | 2011158227 A2 | | 12/2011 |
| WO | WO 2011/158227 | * | 12/2011 |
| WO | WO 2012/109621 | | 8/2012 |
| WO | 2014097301 | * | 6/2014 |
| WO | 2014097301 A1 | | 6/2014 |

OTHER PUBLICATIONS

Chinese Office Action dated Jan. 2, 2019 for corresponding Chinese Application No. 201580043295.3.

European Search Report dated Nov. 6, 2017 for corresponding EP Application No. EP15810830.8.

* cited by examiner

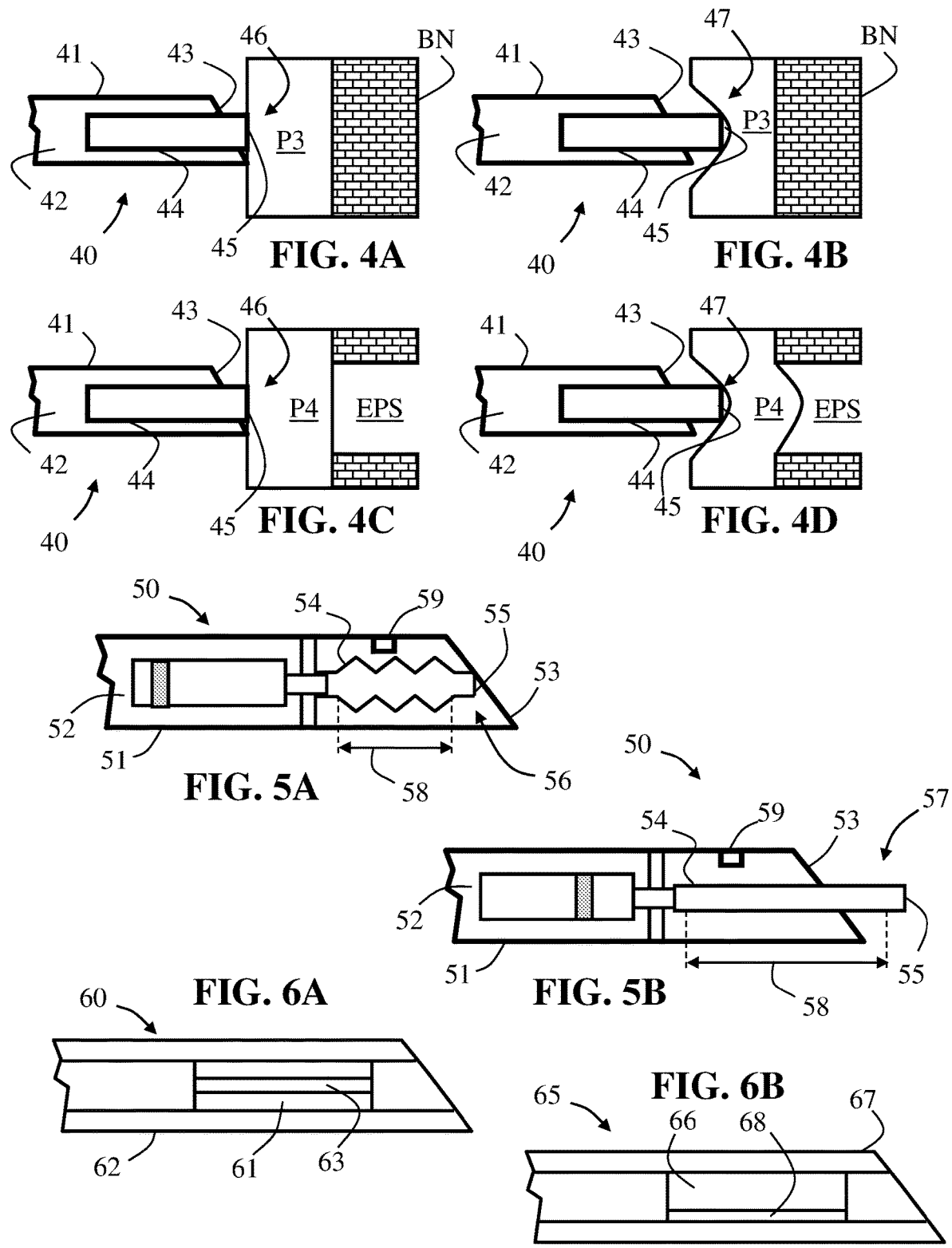

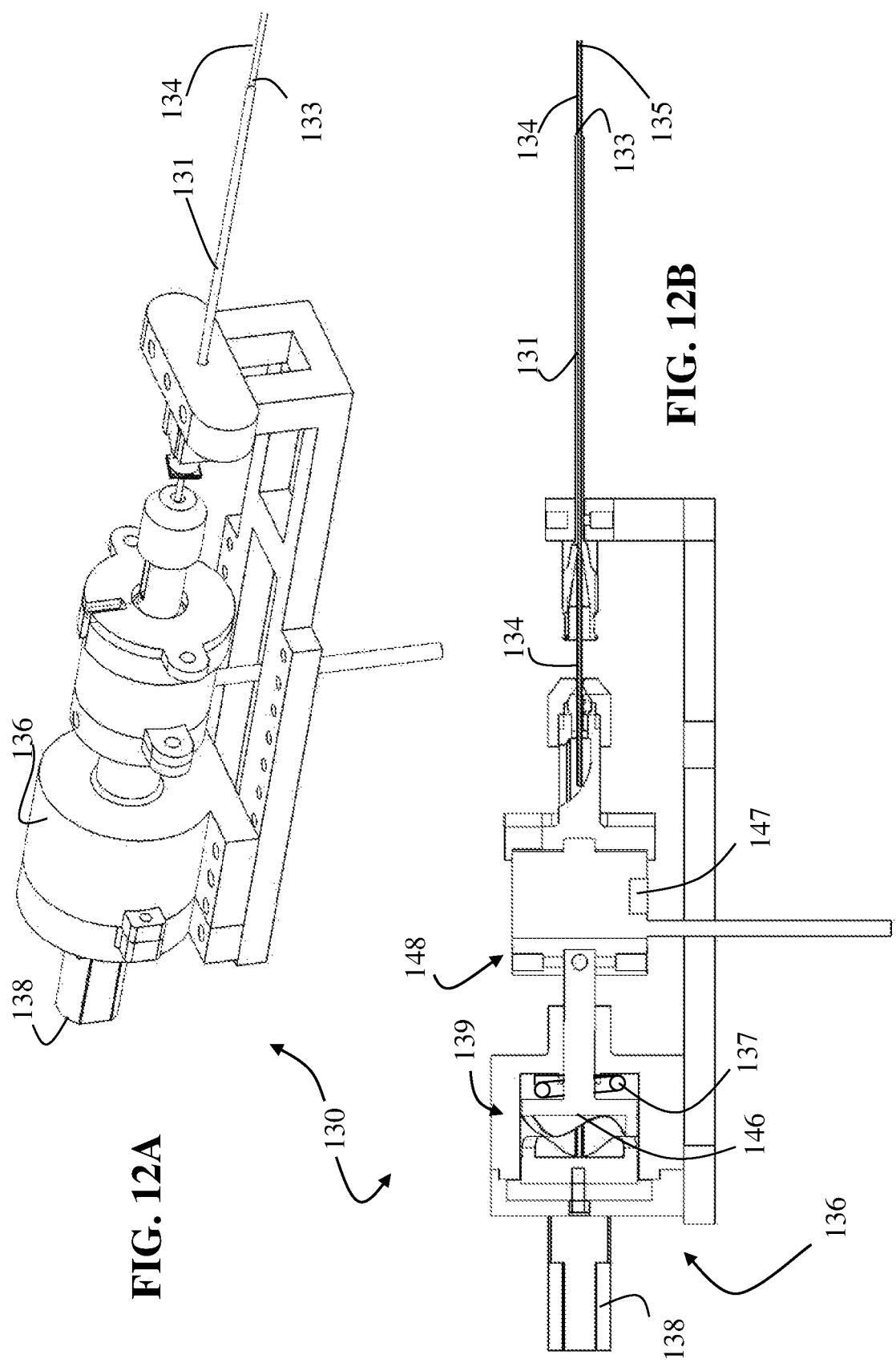

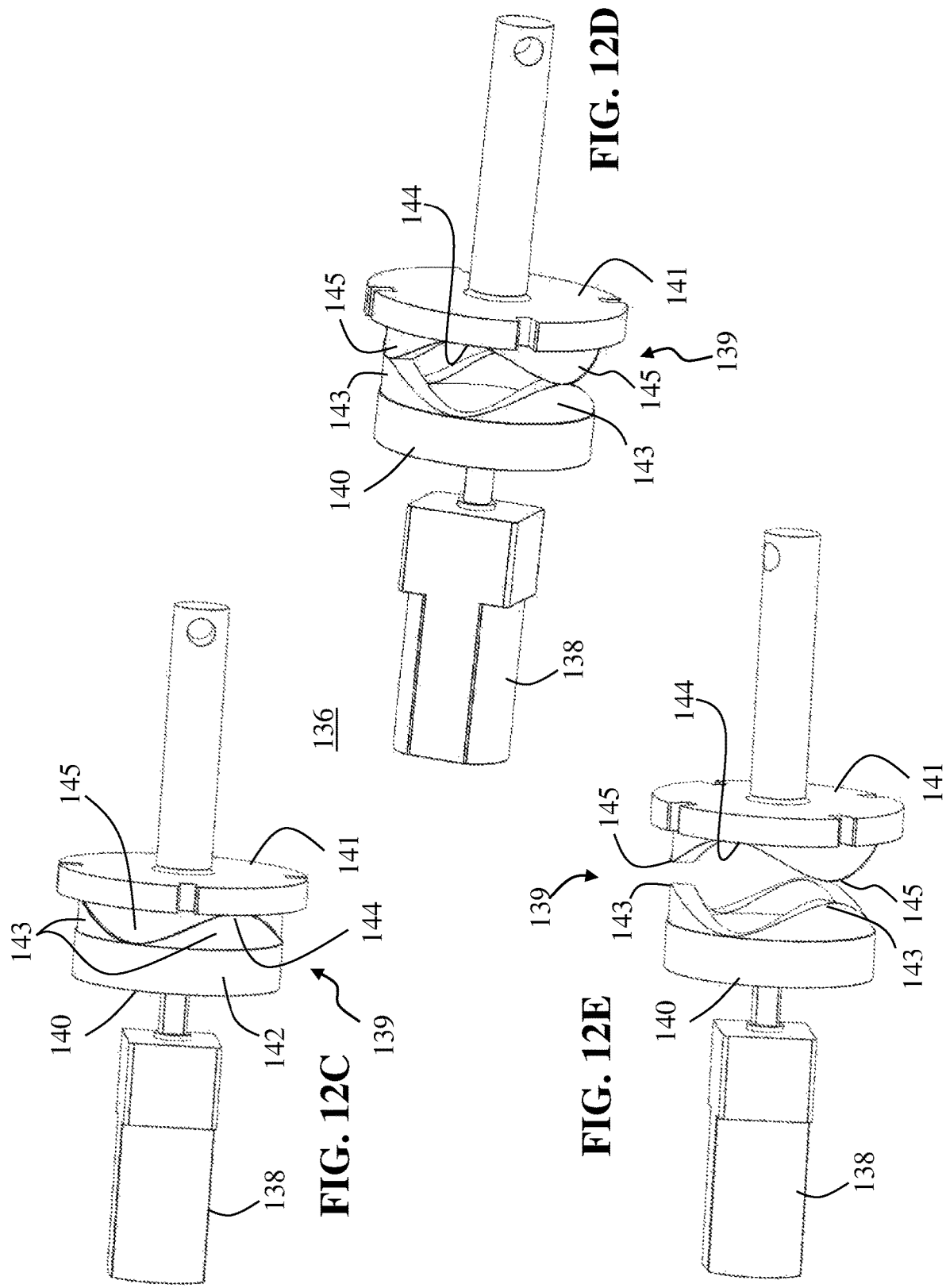

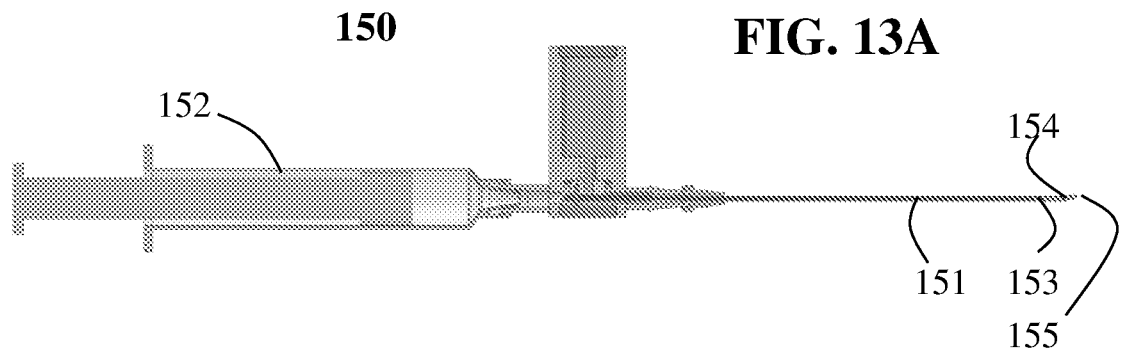
FIG. 13A
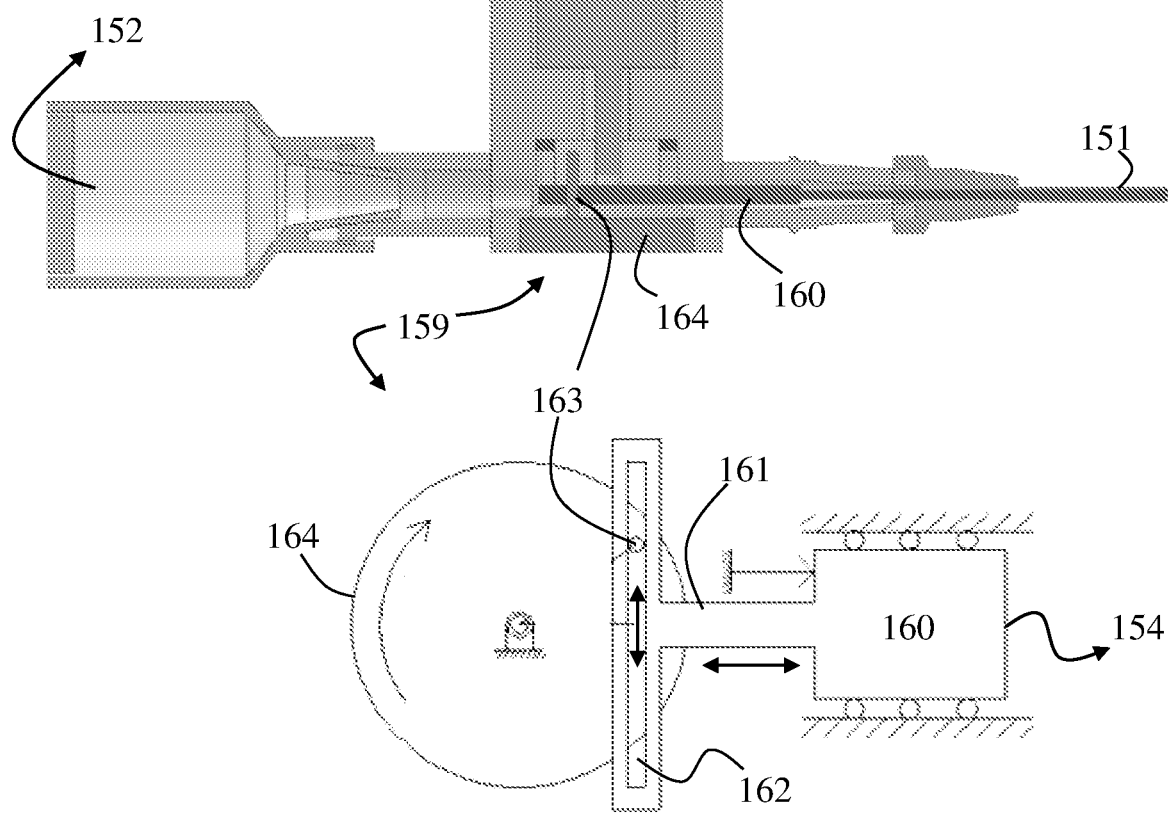
FIG. 13B
FIG. 13C

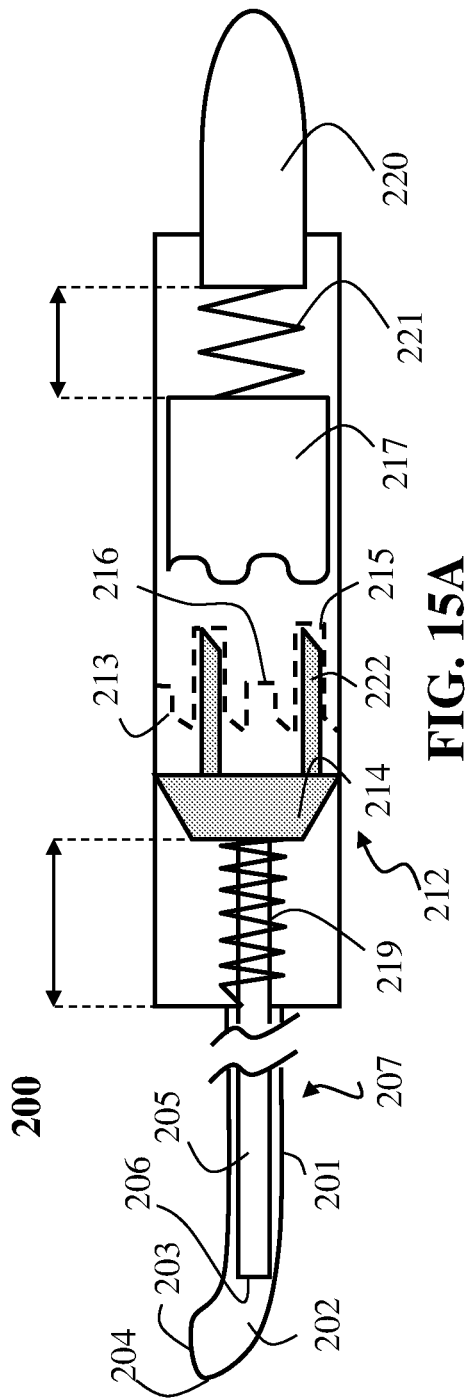
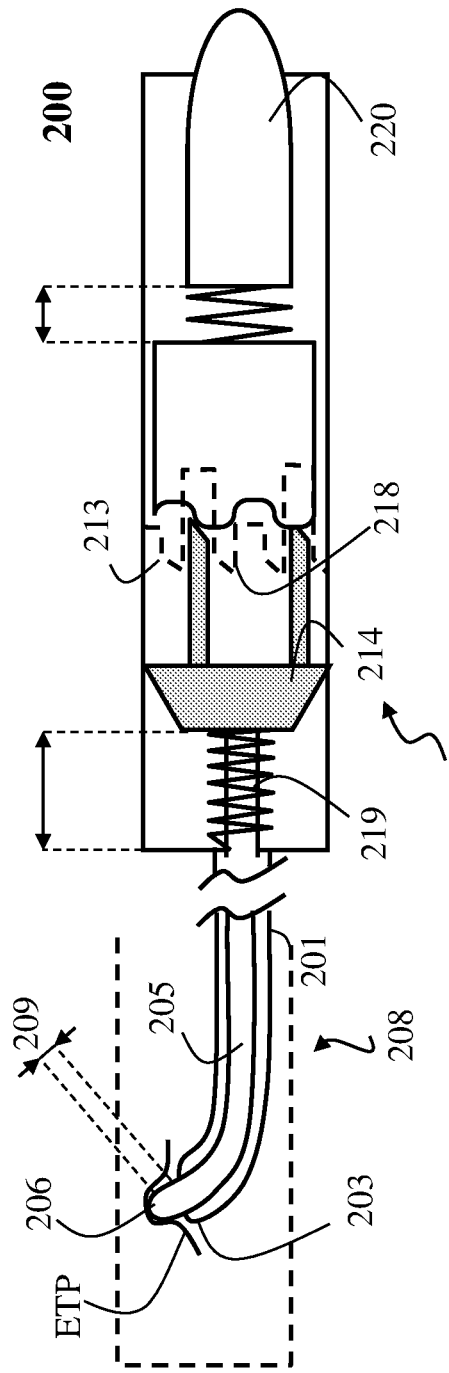
FIG. 15A
FIG. 15B

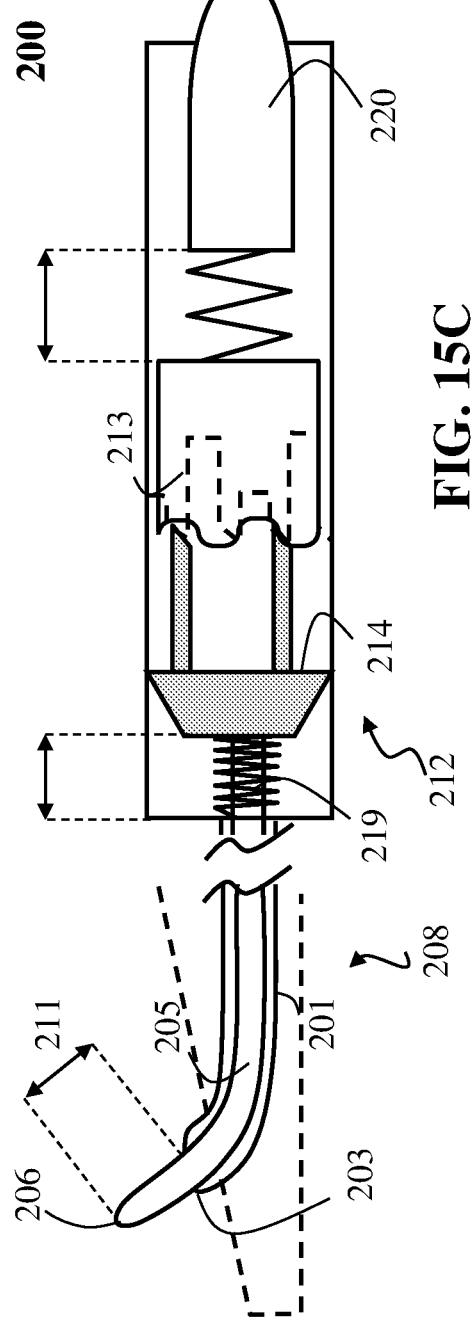
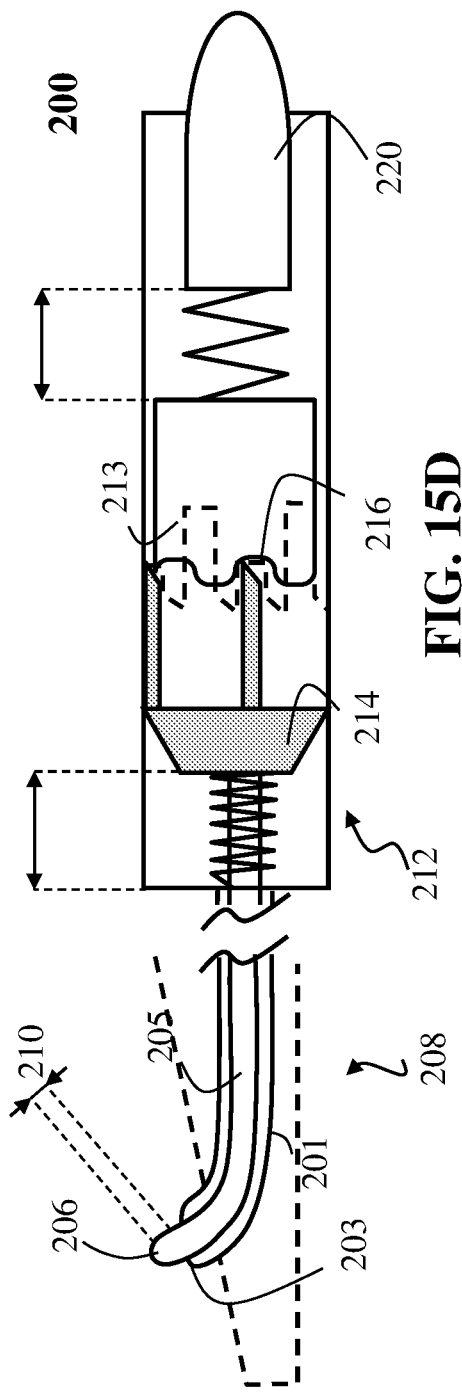
FIG. 15C
FIG. 15D

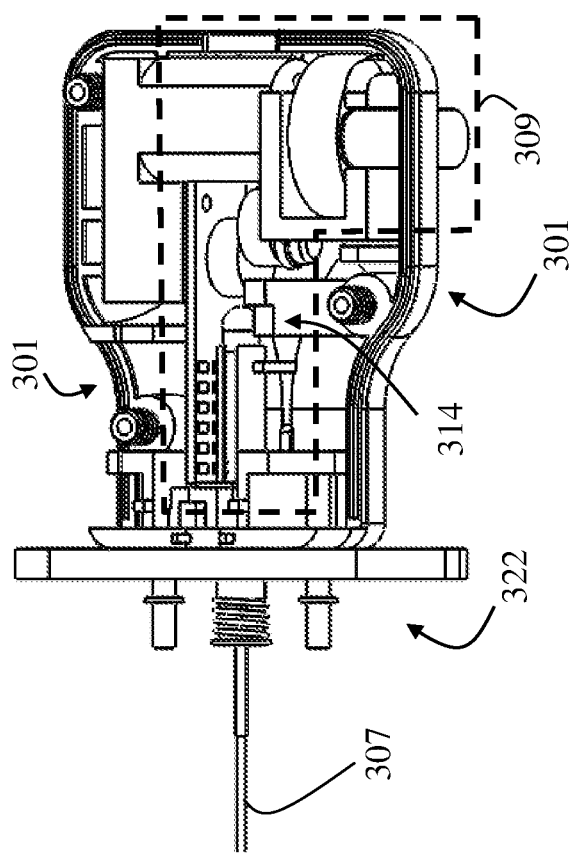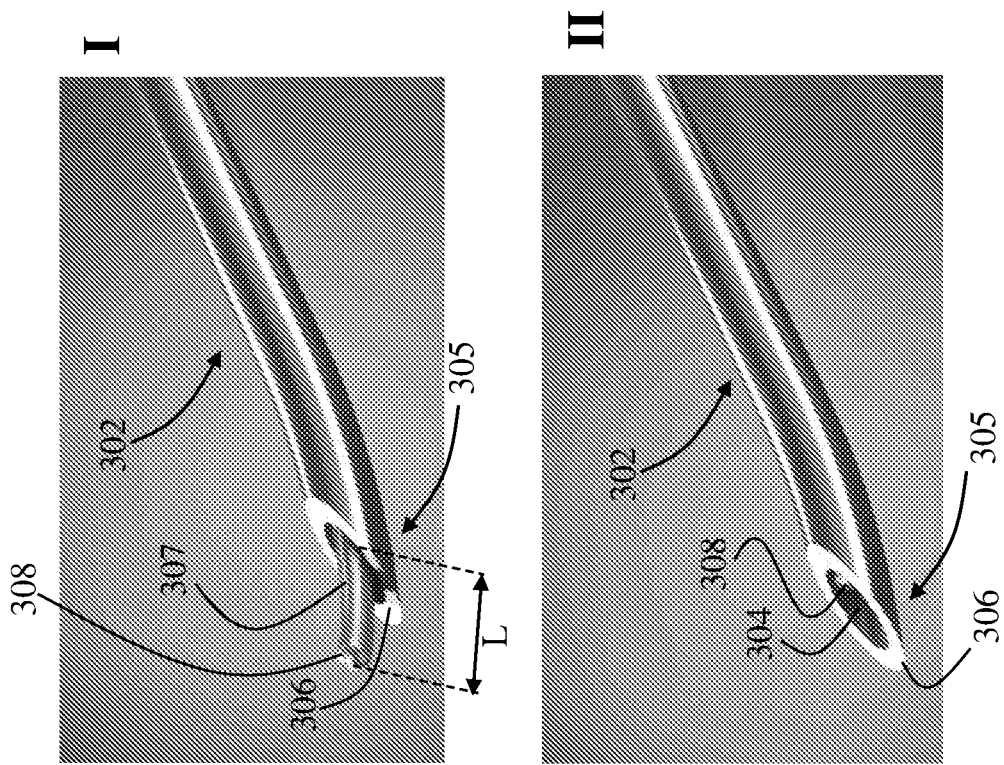
FIG. 16D
FIG. 16C

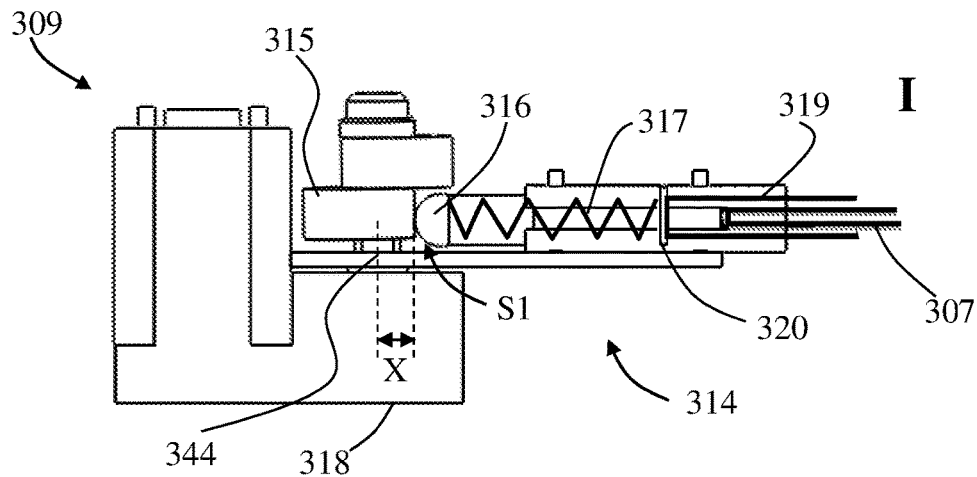
FIG. 16E
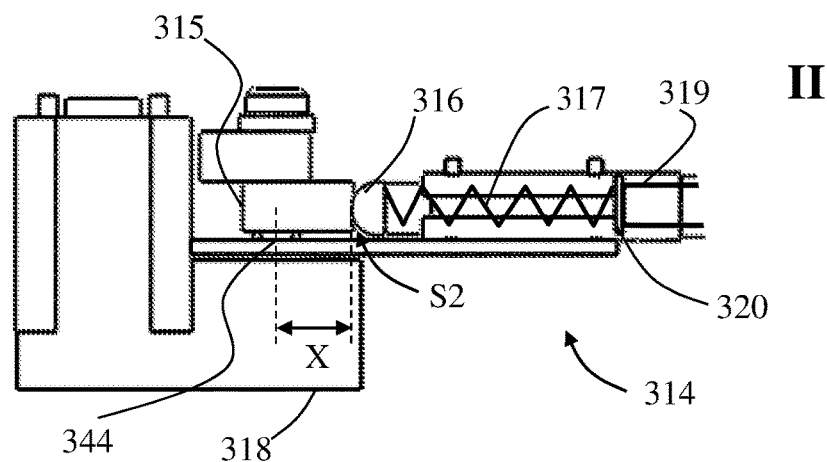
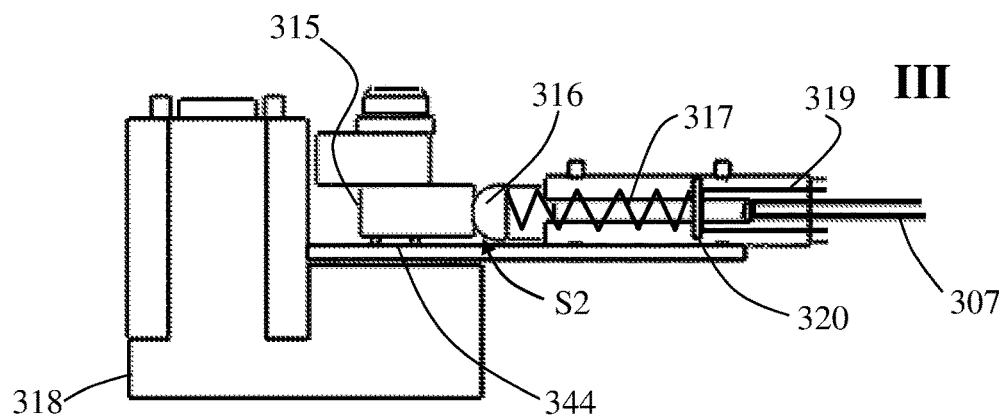

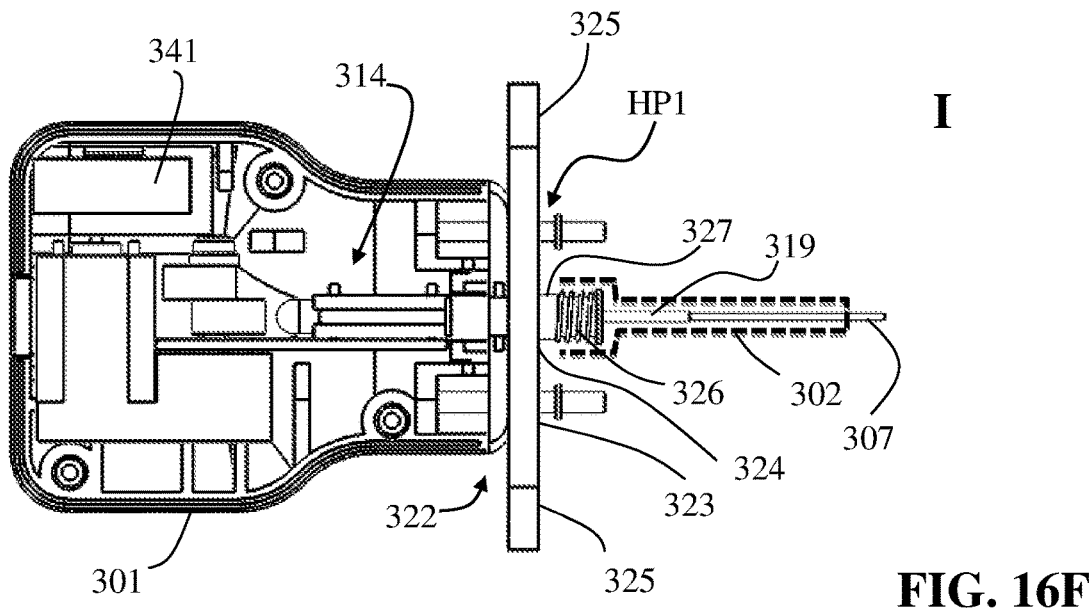
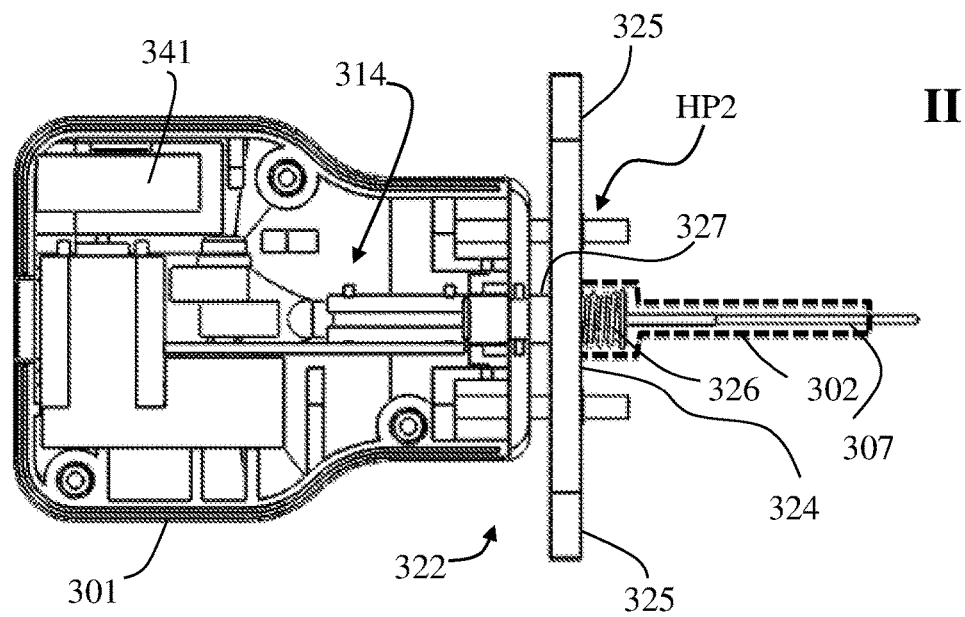
FIG. 16F

400  FIG. 17

*{Delivering a therapeutic substance to a target anatomic location in a subject's body.}*

404

Providing a system including a cannular member enclosing a cannula lumen opened at a cannula distal end having a sharp edge, and further including a pusher-probe having a dull or blunt pusher-probe distal end, and an actuation mechanism adapted to actuate repeated protrusions of the pusher-probe distal end relative to the cannula distal end.

408

Applying the actuating mechanism to effect continuous cycles of a protrusion of the pusher-probe distal end relative to the cannula distal end, followed by an immediate retraction of the pusher-probe distal end when under a retractive force.

412

Advancing towards the target anatomic location in the subject's body by pushing forward the cannular member, via transtissually penetrating soft tissue with the cannula distal end sharp edge at intervals when the pusher-probe distal end is retracted proximally to the sharp edge, wherein the advancing is interrupted with resistance thereto by incoming body tissue mass at other intervals when the pusher-probe distal end is protruded distally to the sharp edge.

416

Recognizing that the cannula distal end is at the target anatomic location for ceasing the advancing.

420

Delivering, via the cannula lumen, the therapeutic substance to the target anatomic location in the subject's body.

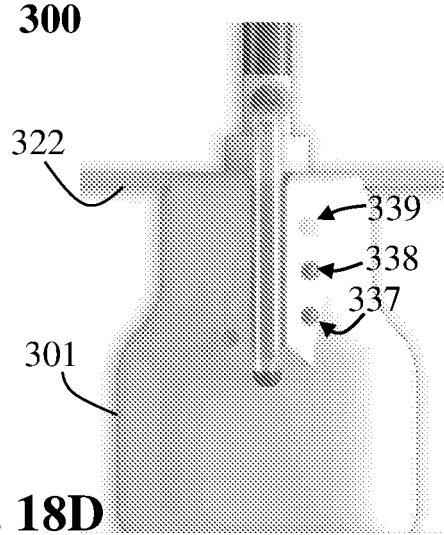
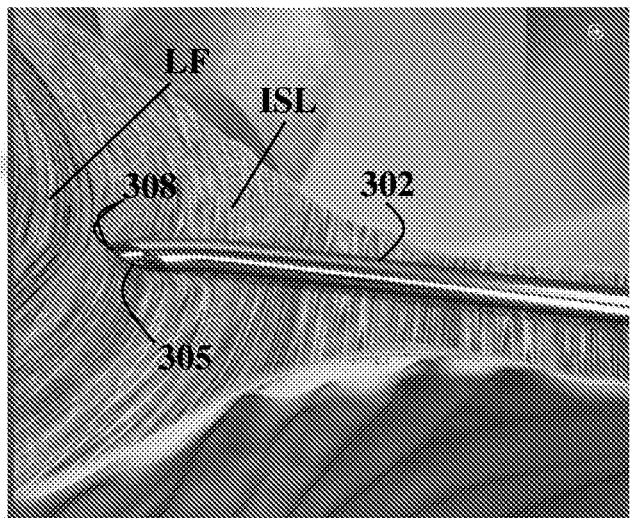
FIG. 18D
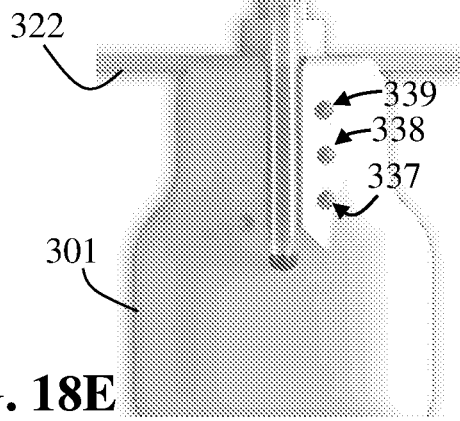
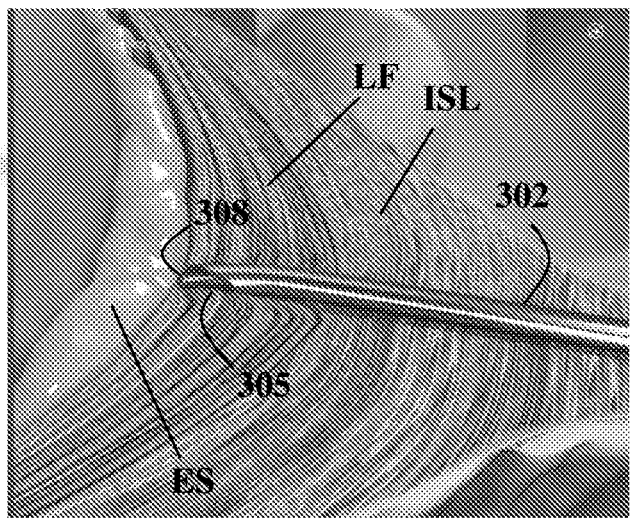
FIG. 18E
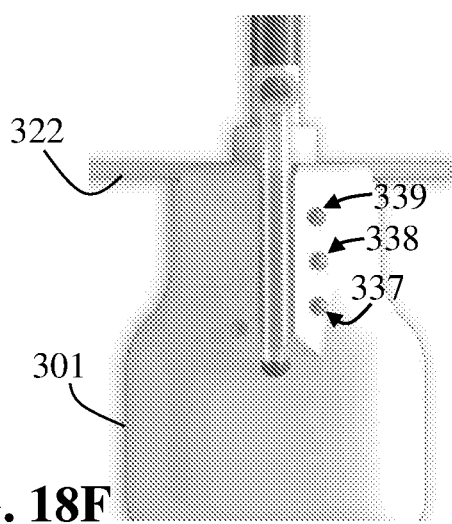
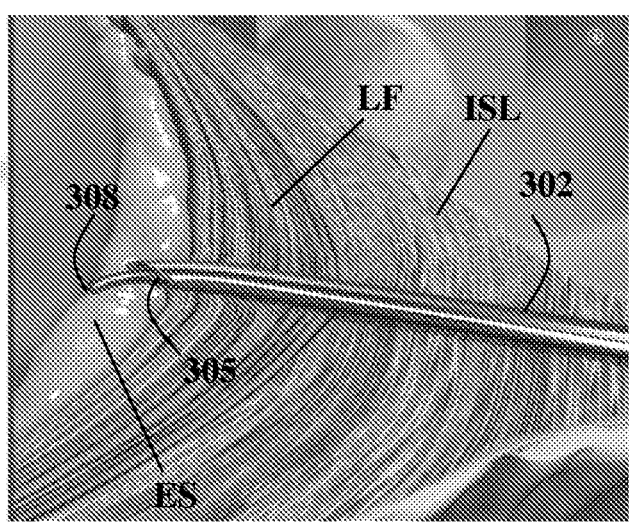
FIG. 18F

IDENTIFYING A TARGET ANATOMIC LOCATION IN A SUBJECT'S BODY, AND DELIVERING A MEDICINAL SUBSTANCE THERETO

RELATED APPLICATIONS

This application is a U.S. National Stage Entry Under 35 U.S.C. 371 of International Application No. PCT/IB2015/054704 filed on Jun. 23, 2015, which claims the benefit of priority under 35 USC 119(e) of U.S. Provisional Patent Application No. 62/015,532, filed Jun. 23, 2014, entitled "Devices And Methods For Identifying An Anatomic Location". The contents of the above applications are incorporated herein by reference in their entirety.

FIELD OF THE INVENTION

The present invention, in some embodiments thereof, relates to identification of bodily locations or tissues, and more particularly, but not exclusively, to techniques (systems, methods) for identifying a target anatomic location in a subject's body, including of humans or other mammals, and for optionally delivering a medicinal substance thereto, or for performing a different treatment or effect to a target tissue, following transtissual progression (penetrating and optionally cutting through layers of body tissue) of a medical device and reaching the body tissue mass with a distal tip thereof. Some embodiments of the present invention involve acquiring mechanical properties of body tissue mass following the medical device transtissual progression. In exemplary embodiments, the medicinal substance is, or includes, a drug, for example, an anesthetic agent, and the target anatomic location is epidural space in the subject's body.

BACKGROUND OF THE INVENTION

Accurately maneuvering and placing an invasive medical device, particularly in the form of a needle, in a small or/and sensitive location in the body of a patient, is an arduous procedure usually involving considerable know-how and skills evolving from years of experience. For example, placing a needle in an epidural space (e.g., for administering medication) needs to be performed accurately and sensitively in order to avoid harm to adjacent tissues, such as the dura mater or even surrounding nerve tissue and blood vessels. Overshooting of the tip of the needle beyond the epidural space may puncture the dura mater, which can cause a leak of the cerebral-spinal fluid (CSF) from around the spinal cord into the epidural space, leading to post-dural puncture headaches syndrome, and possibly also to complications that may lead to paralysis and even death.

The majority of current injection techniques are "blind" techniques, mainly tactile based. For example, the main technique of epidural access is based on the "loss of resistance technique" (LORT). In LORT, a fluid or air filled syringe is attached to a needle. While the needle is advanced through different layers in the insertion site, the physician taps on the syringe. Inside dense ligament layers, the physician feels a strong resistance, but when crossing the ligamentum flavum and entering epidural space, there is a substantial loss of resistance so that the fluid or air from syringe can be easily pushed into the low-pressured epidural space, thus potentially alerting the physician to stop advancing the needle and stationing in the epidural space.

U.S. Pat. No. 8,920,388, to Slocum, et al., describes an apparatus for providing feedback regarding the material in which tip of the apparatus is located as the tip is advanced into matter of varying resistances. The apparatus responds to a change in pressure, force, or other parameter such that when the tip reaches matter of a certain resistance, a change in the parameter is sensed. The apparatus provides a driving force to a penetrating medical device, such as a needle, when the apparatus tip encounters material of high resistance. When the apparatus tip encounters a low resistance material, no further driving force is applied to the apparatus. An inner core may be advanced into the low resistance material for deployment of a gas or a liquid as desired.

Exemplary teachings and practices in the field of the invention, by the same applicant/assignee of the present disclosure, are provided in WIPO PCT Pat. Appl. Int'l. Pub. Nos.: WO 2014/097301; and WO 2011/158227.

SUMMARY OF THE INVENTION

The present invention, in some embodiments thereof, relates to techniques (systems, methods) for identifying a target anatomic location in a subject's body, and for delivering the medicinal substance to the target anatomic location in the subject's body, following transtissual progression (penetrating and optionally cutting through layers of body tissue) of a medical device and reaching the body tissue mass with a distal tip thereof. Some embodiments of the present invention involve acquiring mechanical properties of body tissue mass following the medical device transtissual progression. In exemplary embodiments, the medicinal substance is, or includes, a drug, for example, an anesthetic agent, and the target anatomic location is epidural space in the subject's body.

In some embodiments, the medical device is a specially designed, constructed, and operative 'pusher-probe' whose distal end is provided in a cannula lumen. In exemplary embodiments, the pusher-probe is a noncompliant rigid member, or otherwise being stiffer than incoming tissue mass at least along its longitudinal axis and optionally to bending or collapsing when housed in the cannula. In some embodiments, as such, the pusher-probe is configured and suitable for 'pushing (probing) through' and 'mechanically manipulating' (deforming) soft tissue it encounters and progresses (advances) through, in a manner whereby the pusher-probe exhibits minimal to no deformation.

Exemplary embodiments of the system include a specially designed, constructed, and operative 'extending mechanism' that includes a cam member and associated components configured for enabling selective traveling of the distal end of the medical device (for example, the pusher-probe) in a cannula lumen, such that the medical device distal end (pusher-probe distal end) becomes repositioned between a retracted position and a protruding position.

Exemplary embodiments of the system include a data-information analyzing device having a specially designed, constructed, and operative 'triggering mechanism' that includes a 'winged' hub member and associated components thereof.

According to an aspect of some embodiments of the present invention, there is provided a system for identifying a target anatomic location penetrated to by a medical device distal tip following transtissual progression thereof through a body tissue mass, the system comprising: a cannular member enclosing a cannula lumen opened at a cannula distal end having a sharp edge; a pusher-probe having a pusher-probe distal end provided in the cannula lumen, the pusher-probe distal end is positionable from a retracted position, being enclosed within the cannula lumen, to a protruding position, in which the pusher-probe distal end protrudes out of the cannula distal end to a length in a range of between a minimal protrusion length and a maximal protrusion length; and an actuation mechanism adapted to actuate repeated protrusions of the pusher-probe distal end relative to the cannula distal end including continuous cycles of a protrusion of the pusher-probe distal end relative to the cannula distal end followed by an immediate retraction of the pusher-probe distal end when under a retractive force.

According to some embodiments of the invention, the actuation mechanism includes an extending mechanism comprising a cam member, and a follower shiftable from a first station to a second station on the cam member, wherein the follower is configured for applying forces to the pusher-probe thereby effecting change in position of the pusher-probe distal end relative to the cannula distal end, in accordance with distance of the follower from rotation center of the cam member or/and with resistance to the pusher-probe by incoming body tissue mass.

According to some embodiments of the invention, the pusher-probe distal end is configured for remaining in the retracted position, when the follower rests in the first station.

According to some embodiments of the invention, the pusher-probe distal end is configured for remaining in the minimal protrusion length, when the follower rests in the second station.

According to some embodiments of the invention, the first station and second station are separated by an edge, and the follower includes at least one engaging member movable between the first station and the edge or between the second station and the edge, wherein the extending mechanism is arranged such that only upon the pusher-probe distal end reaching the maximal protrusion length, each of the at least one engaging member shifts from the first station to the second station across the edge.

According to some embodiments of the invention, the extending mechanism includes a measuring spring between the follower and the pusher-probe, configured to change in length between a first compressed or unstressed length and a second compressed length related to a difference between an activating force applied thereto by the follower and an opposing resistive force applied thereto by the pusher-probe.

According to some embodiments of the invention, the resistive force equals the resistance to the pusher-probe by the incoming body tissue mass.

According to some embodiments of the invention, the extending mechanism further comprising a plunger configured for selective traveling in the cannula lumen while forcing relative motion between the cam member and the follower, wherein via the selective traveling, the pusher-probe distal end repositions between the retracted position and the protruding position.

According to some embodiments of the invention, the actuating mechanism further comprises a push button and a tactile spring interconnected with the plunger.

According to some embodiments of the invention, the actuating mechanism is variable in length, and confined to a first length within a first range of lengths when pressed against the pusher-probe with the distal end thereof at the maximal protrusion length, and confined to a second length within a second range of lengths, nonintersecting with the first range of lengths, when pressed against the pusher-probe with the distal end thereof in the protruding position with the length being less than the maximal protrusion length, wherein each of the at least one engaging member is allowed to shift across the edge when the actuating mechanism is at the first length and to retract back to the first station or to the second station when the actuating mechanism is at the second length.

According to some embodiments of the invention, the push button is manually operable.

According to some embodiments of the invention, the extending mechanism includes a measuring spring between the follower and the pusher-probe configured to change in length between a first length and a second length related to a difference between an activating force applied thereto by the follower and an opposing resistive force applied thereto by the pusher-probe.

According to some embodiments of the invention, the extending mechanism is configured such that a length or a change in length of said measuring spring correlate with a mechanical property of the body tissue mass.

According to some embodiments of the invention, the resistive force equals the resistance to the pusher-probe by the incoming body tissue mass.

According to some embodiments of the invention, the measuring spring is connected to a marking flag provided between the measuring spring and the pusher-probe, the marking flag is movable with motions of the pusher-probe relative to a stationary proximity sensor, applicable to measuring distance to the marking flag, between a predetermined range of distances, therefrom.

According to some embodiments of the invention, the range of distances is between 0 and 7 mm.

According to some embodiments of the invention, a complete single rotation cycle of the cam member around the rotation center thereof affects an activation cycle of the pusher-probe, including a single protrusion maneuver followed by a single retraction of the pusher probe distal end, wherein the system is configured such that the activation cycle includes an effective measuring period being equal to, or shorter in duration than, the entire cycle duration, the effective measuring period corresponds with the proximity sensor measuring particularly of distances within the range of distances.

According to some embodiments of the invention, the effective measuring period is determined by at least one of:
  any continuous period in which said measuring spring is stressed,
  any continuous period in which said marking flag is distanced away from said proximity sensor by no more than a predetermined value or/and by 4 mm or less, and
  relative positioning of said cam member.

According to some embodiments of the invention, the pusher-probe is noncompliant and rigid relative to the body tissue mass if provided at least partially within the cannula.

According to some embodiments of the invention, the pusher-probe distal end is configured to mechanically manipulate a portion of the body tissue mass, via thrusting into and then releasing contact with the portion of the body tissue mass, during the repositioning of the pusher-probe distal end to the retracted position or/and to the protruding position.

According to some embodiments of the invention, the system further comprises a sensor adapted to correlate a mechanical property of the body tissue mass with a sensed affect resulting from the body tissue mass reacting to the mechanical manipulation.

According to some embodiments of the invention, the system further comprises a data-information analyzing device including an integrated circuit or/and a data-information processing/programming unit programmed to assign a numerical value to the sensed affect.

According to some embodiments of the invention, the data-information analyzing device comprises a memory, wherein the data-information processing/programming unit is programmed to store a database of previous numerical values assigned to previous sensed affects or/and other stored information, and to compare the numerical value of the sensed affect to the previous numerical values of the database.

According to some embodiments of the invention, the system further comprises a trigger mechanism comprised of: a winged hub member including a hub body coupled with at least one wing-like flange sized and shaped for effective finger pressing thereto, the hub body is slidably connected via a structural portion of the system proximally to the cannular member and slidable from a first hub position to a second hub position distal to the first hub position.

According to some embodiments of the invention, the trigger mechanism comprises a hub retracting mechanism configured for resisting motion of the winged hub member away from the first hub position.

According to some embodiments of the invention, the hub retracting mechanism is configured for allowing only if pressed distally with a force greater than a predetermined threshold force.

According to some embodiments of the invention, the hub retracting mechanism is configured for retracting the winged hub member relative to the structural portion of the system after reaching the second hub position or/and if pressed distally with a force less than the predetermined threshold force.

According to some embodiments of the invention, the system further comprises a hub locator configured for signaling to the data-information analyzing device a predetermined signal corresponding to at least one of a location of the winged hub member at the second hub position and a location of the winged hub member away from the first hub position, for at least 0.3 second; wherein the data-information analyzing device is programmed to assign the numerical value to the sensed affect, or/and to indicate proximity of, or positioning in, a target anatomic location, only upon or while receiving the predetermined signal from the hub locator.

According to some embodiments of the invention, the winged hub member includes two of the wing-like flanges connected at opposing locations around the hub body, so as to allow pressing thereof in-parallel by two fingers from two sides around the cannular member.

According to some embodiments of the invention, the pusher-probe distal end is sized or/and shaped so as to prevent penetration thereof into the body tissue mass during the repositioning.

According to some embodiments of the invention, the pusher-probe is configured such that fluid travels thereacross or/and therethrough when in the retracted position or/and when in the protruding position.

According to some embodiments of the invention, the maximal protrusion length is equal to or less than about 5 mm.

According to some embodiments of the invention, the distance of the pusher-probe distal end to the cannula distal end in the protruding position is determined according to the mechanical property of the body tissue mass, and wherein the distance is in a range of between about 0.2 mm and about 5 mm.

According to some embodiments of the invention, the pusher-probe distal end is configured to non-traumatically mechanically manipulate the body tissue mass by at least one of laterally stretching, distally compressing, distally curving, distally bending, distally pushing, and rotationally twisting, the body tissue mass, or/and by at least partially immersing in the body tissue mass.

According to some embodiments of the invention, the system further comprises a signifying device linked with at least one of the data-information analyzing device and the sensor, and including at least one of a visual signaling unit and an audio signaling unit.

According to some embodiments of the invention, the system further comprises a coupling to a loss of resistance (LOR) type syringe or/and wherein the cannular member includes or is in a form of an epidural needle.

According to some embodiments of the invention, the coupling is in fluid communication with the cannula lumen.

According to some embodiments of the invention, the system further comprises a fluid channel having an at least partially transparent portion provided between the coupling and the cannula lumen, thereby allowing presence of fluid thereinside.

According to some embodiments of the invention, the system is configured such that the retractive force is applied by a retraction spring changeable in length during pusher-probe distal end repositioning from the retracted position to the protruding position.

According to some embodiments of the invention, the actuation mechanism is adapted for automatic reciprocal repositioning of the pusher-probe distal end between the retracted position and the protruding position during a defined actuation period.

According to some embodiments of the invention, the actuation mechanism includes a motion source for providing continuous reciprocal repositioning to the pusher-probe distal end relative to the cannular member distal end.

According to some embodiments of the invention, the reciprocal repositioning includes a plurality of stroke cycles, each comprising a single forward stroke from the retracted position to the protruding position, and a single backward retraction from the protruding position to the retracted position, wherein the stroke cycles have a frequency in a range of between about 0.5 Hz and about 10 Hz.

According to some embodiments of the invention, the reciprocal repositioning facilitates unhindered transtissual progression of the medical device through soft tissue with a progression velocity equal to or less than about 5 mm per second.

According to some embodiments of the invention, the sensed effect is sampled with a sampling rate in a range of between about 50 Hz and about 1,000 Hz.

According to an aspect of some embodiments of the present invention, there is provided a system for acquiring mechanical properties of a body tissue mass following transtissual progression of a medical device and reaching the body tissue mass with a distal tip thereof, the system comprising: a cannular member enclosing a cannula lumen opened at a cannula distal end; a pusher-probe having a dull or blunt pusher-probe distal end provided in the cannula lumen, the pusher-probe distal end is positionable from a retracted position, being enclosed within the cannula lumen, to a protruding position, in which the pusher-probe distal end protrudes out of the cannula distal end to a length up to a maximal protrusion length, wherein when the cannula distal end is located in front of the body tissue mass, and during repositioning thereof to the retracted position or/and to the protruding position, the pusher-probe distal end is configured to mechanically manipulate a portion of the body tissue mass, via thrusting into and then releasing contact with the body tissue; an actuation mechanism adapted to actuate protrusion of the pusher-probe distal end relative to the cannula distal end and to allow an immediate follow-up retraction of the pusher-probe distal end if under a retractive force; and a sensor adapted to correlate a mechanical property of the body tissue mass with a sensed effect resulting from the mechanical manipulation causing the body tissue mass to react thereto.

According to some embodiments of the invention, the pusher-probe is noncompliant and rigid relative to the body tissue mass if provided at least partially within the cannula.

According to some embodiments of the invention, the pusher-probe is configured such that fluid travels thereacross or/and therethrough when in the retracted position or/and when in the protruding position.

According to some embodiments of the invention, the pusher-probe distal end is configured to effect the mechanical manipulation non-traumatically to the body tissue mass by at least one of laterally stretching, distally compressing, distally curving, distally bending, distally pushing, and rotationally twisting, the body tissue mass, or/and by at least partially immersing in the body tissue mass.

According to some embodiments of the invention, the actuation mechanism includes a selectively engageable coupling comprising a drive member releasably engageable with a piston member connected to the pusher-probe.

According to some embodiments of the invention, the system is configured such that the mechanical manipulation causing the body tissue mass to react thereto includes the retractive force applied by the body tissues mass at a contact area with the pusher-probe distal end.

According to some embodiments of the invention, the system further comprises a data-information analyzing device including an integrated circuit or/and a data-information processing/programming unit programmed to assign a numerical value to the sensed effect.

According to some embodiments of the invention, the data-information analyzing device comprises a memory, wherein the data-information processing/programming unit is programmed to store a database of previous numerical values assigned to previous sensed effects or/and other stored information, and to compare the numerical value of the sensed effect to the previous numerical values of the database.

According to some embodiments of the invention, the system further comprises a signifying device linked with the sensor and including at least one of a screen, a LED, a printer, an audio signal transducer, a tactile signal transducer, and an audiovisual transducer.

According to some embodiments of the invention, the system further comprises a loss of resistance (LOR) type syringe.

According to some embodiments of the invention, the system is configured such that the retractive force is applied by a retraction spring configured for changing in length from a lower stress to a higher stress during pusher-probe distal end repositioning from the retracted position to the protruding position, intended for repositioning the pusher-probe distal end in the retracted position when the pusher-probe is not forced distally towards protruding.

According to some embodiments of the invention, the actuation mechanism is adapted for automatic reciprocal repositioning of the pusher-probe distal end between the retracted position and the protruding position during a defined actuation period.

According to some embodiments of the invention, the reciprocal repositioning includes a plurality of stroke cycles, each comprising a single forward stroke from the retracted position to the protruding position, and a single backward retraction from the protruding position to the retracted position, wherein the stroke cycles have a frequency in a range of between about 0.5 Hz and about 10 Hz.

According to some embodiments of the invention, the reciprocal repositioning facilitates unhindered transtissual progression of the medical device through soft tissue with a progression velocity equal to or less than about 5 mm per second.

According to some embodiments of the invention, the system further comprises a trigger mechanism.

According to an aspect of some embodiments of the present invention, there is provided a system for delivering a medicinal substance to a target location in a subject's body, the system comprising: a cannular member enclosing a cannula lumen opened at a cannula distal end having a sharp edge; a pusher-probe having a pusher-probe distal end provided in the cannula lumen, the pusher-probe distal end is positionable from a retracted position, being enclosed within the cannula lumen, to a protruding position, in which the pusher-probe distal end protrudes out of the cannula distal end to a length in a range of between a minimal protrusion length and a maximal protrusion length; and an actuation mechanism adapted to actuate repeated protrusions of the pusher-probe distal end relative to the cannula distal end including continuous cycles of a protrusion of the pusher-probe distal end relative to the cannula distal end followed by an immediate retraction of the pusher-probe distal end when under a retractive force.

According to some embodiments of the invention, the actuation mechanism includes an extending mechanism comprising a cam member, and a follower shiftable from a first station to a second station on the cam member, wherein the follower is configured for applying forces to the pusher-probe thereby effecting change in position of the pusher-probe distal end relative to the cannula distal end, in accordance with distance of the follower from rotation center of the cam member or/and with resistance to the pusher-probe by incoming body tissue mass.

According to some embodiments of the invention, the extending mechanism includes a measuring spring provided between the follower and the pusher-probe and configured to change in length between a first length and a second length related to a difference between an activating force applied thereto by the follower and an opposing resistive force applied thereto by the pusher-probe.

According to some embodiments of the invention, the resistive force equals the resistance to the pusher-probe by the incoming body tissue mass.

According to some embodiments of the invention, the pusher-probe is noncompliant and rigid relative to the body tissue mass within the cannula.

According to some embodiments of the invention, the pusher-probe distal end is configured to mechanically manipulate a portion of the body tissue mass, via thrusting into and then releasing contact with the portion of the body tissue mass, during the repositioning of the pusher-probe distal end to the retracted position or/and to the protruding position.

According to some embodiments of the invention, the system further comprises a sensor adapted to correlate a mechanical property of the body tissue mass with a sensed affect resulting from the body tissue mass reacting to the mechanical manipulation.

According to an aspect of some embodiments of the present invention, there is provided a method for acquiring mechanical properties of a body tissue mass, the method comprising: providing a system comprised of a cannular member enclosing a cannula lumen opened at a cannula distal end and including a pusher-probe having a dull or blunt pusher-probe distal end; transtissueally penetrating soft tissue with the cannular member until reaching the body tissue mass non-penetrated by the cannula distal end; mechanically manipulating a portion of the body tissue mass by repositioning the pusher-probe distal end to a protruding position located outside of the cannula distal end; allowing the pusher-probe distal end to immediately retract back to the retracted position, and recording a sensed effect resulting from the mechanical manipulation causing the body tissue mass to react thereto.

According to some embodiments of the invention, the method further comprises: correlating the recorded sensed effect with a mechanical property of the body tissue mass.

According to some embodiments of the invention, the pusher-probe is axially supported by an elastic member configured to continuously force the pusher-probe distal end to proximally shift within the cannula lumen up to the retracted position, such that the pusher-probe distal end immediately retracts following the allowing.

According to some embodiments of the invention, providing the system includes a syringe, and further comprising applying the syringe with the cannular member to facilitate performing of a loss of resistance technique at an anatomic location inside of or beyond the body tissue mass.

According to some embodiments of the invention, the method comprises repeating the transtissueally penetrating, the mechanically manipulating, the allowing, and the recording, until detecting a signal indicative of a target tissue or of a space adjacent to or between tissues.

According to some embodiments of the invention, the method further comprises: delivering a fluid through or across the pusher-probe, or through the cannula lumen in absence of the pusher-probe, into or adjacent to the target tissue or the space.

According to some embodiments of the invention, the delivering is performed after at least one of removing the pusher-probe from the cannula lumen, and passing a catheter via the cannula lumen towards the target tissue or the space adjacent to or between tissues.

According to some embodiments of the invention, the method further comprises delivering a medicinal substance or/and a medical tool across or through the pusher-probe into, or adjacent to, the target tissue or the space.

According to an aspect of some embodiments of the present invention, there is provided a method for delivering a medicinal substance to a target anatomic location in a subject's body, the method comprising: providing a system comprised of a cannular member enclosing a cannula lumen opened at a cannula distal end having a sharp edge, the system further comprising a pusher-probe having a dull or blunt pusher-probe distal end, and an actuation mechanism adapted to actuate repeated protrusions of the pusher-probe distal end relative to the cannula distal end; applying the actuating mechanism to effect continuous cycles of a protrusion of the pusher-probe distal end relative to the cannula distal end, followed by an immediate retraction of the pusher-probe distal end if under a retractive force; advancing towards the target anatomic location in the subject's body by pushing forward the cannular member, via transtissually penetrating soft tissue with the cannula distal end sharp edge at intervals when the pusher-probe distal end is retracted proximally to the sharp edge, wherein the advancing is interrupted with resistance thereto by incoming body tissue mass at other intervals when the pusher-probe distal end is protruded distally to the sharp edge; recognizing the cannula distal end is at the target anatomic location for ceasing the advancing; and delivering, via the cannula lumen, the medicinal substance to the target anatomic location in the subject's body.

According to some embodiments of the invention, the target anatomic location is an epidural space and the medicinal substance is a drug.

According to some embodiments of the invention, the drug is, or includes, an anesthetic agent.

According to some embodiments of the invention, the pusher-probe distal end remains noncompliant and rigid relative to the body tissue mass, thereby projecting in line with the cannula distal end when protruded distally to the sharp edge.

According to some embodiments of the invention, in the method, the system further comprises a sensor adapted to correlate a mechanical property of the body tissue mass with a sensed effect resulting from the resistance to advancing of the pusher-probe distal end by the body tissue mass; and wherein the recognizing is effected by at least one of: measuring a sensed effect resulting from the resistance to protrusion of the pusher-probe distal end during the advancing; correlating the sensed effect to a previous record indicative of a known bodily region or/and body tissue mass; comparing the sensed effect with an immediately preceding recorded sensed effect; and signaling upon at least one of measuring a sensed effect resulting from body tissue mass resistance in magnitude taken from a range or ranges of predetermined values, measuring a sensed effect being at least 20-50% different than the immediately previous recorded sensed effect, and measuring a change between recorded sensed effects being indicative of a known bodily region or/and body tissue mass or of penetration from a first bodily region characterized by a first tissue type to a second bodily region characterized by a second tissue type.

According to some embodiments of the invention, the signaling is produced using at least one of a visual signaling unit and an audio signaling unit.

According to some embodiments of the invention, the known bodily region or/and body tissue mass includes at least one of bone tissue, subcutaneous tissue, interspinous ligament, ligamentum flavum, epidural space, fatty tissue, and dura mater.

According to some embodiments of the invention, in the method, the system further comprises a trigger mechanism including a winged hub member slidable from a first hub position to a second hub position distal to the first hub position, wherein at least one of the applying, advancing and recognizing is facilitated only if the winged hub member is at, or distal to, the second hub position.

According to some embodiments of the invention, the pusher-probe is axially supported by an elastic member configured to continuously force the pusher-probe distal end to proximally shift within the cannula lumen.

According to some embodiments of the invention, providing the system includes a syringe, and further comprising applying the syringe with the cannular member to facilitate performing of a loss of resistance technique at an anatomic location inside of or beyond the body tissue mass.

According to some embodiments of the invention, the delivering includes removing the pusher probe from cannula lumen.

According to some embodiments on the invention, the method further comprises ceasing at least one of the applying and the advancing immediately upon the recognizing.

Optionally, the ceasing includes holding the pusher-probe so that the distal end thereof protrudes distally to the sharp edge of the cannula distal end.

Unless otherwise defined, at technical or/and scientific terms used herein have the same meaning as commonly understood by one of ordinary skit in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4D schematically illustrate exemplary mechanical manipulations of differently supported body tissue mass portions using an exemplary system including an exemplary pusher-probe, according to some embodiments of the invention;

FIGS. 5A-5B schematically illustrate an exemplary system including an exemplary axially expandable pusher-probe, according to some embodiments of the invention;

FIGS. 6A-6B schematically illustrate exemplary systems including exemplary pusher-probes configured to allow passage of fluid therethrough and thereacross, respectively, according to some embodiments of the invention;

FIGS. 12A-12E illustrate an exemplary system including an exemplary motor and an exemplary clutch coupling, according to some embodiments of the invention;

FIGS. 13A-13C schematically illustrate an exemplary system including an exemplary motor and an exemplary scotch yoke mechanism, according to some embodiments of the invention;

FIGS. 15A-15D schematically illustrate an exemplary manually controllable system including an exemplary extending mechanism, according to some embodiments of the invention;

FIGS. 16A-16H illustrate exemplary embodiments of a system for delivering a medicinal substance to a target anatomic location in a subject's body, according to some embodiments of the invention;

FIG. 17 is a flow diagram of an exemplary embodiment of a method for delivering a medicinal substance to a target anatomic location in a subject's body, according to some embodiments of the invention; and FIGS. 18A-18G illustrate exemplary embodiments of implementing an exemplary method for delivering a medicinal substance to a target anatomic location in a subject's body, using the exemplary system illustrated in FIGS. 16A-16H, according to some embodiments of the invention.

DESCRIPTION OF SPECIFIC EMBODIMENTS OF THE INVENTION

Figure 1A:
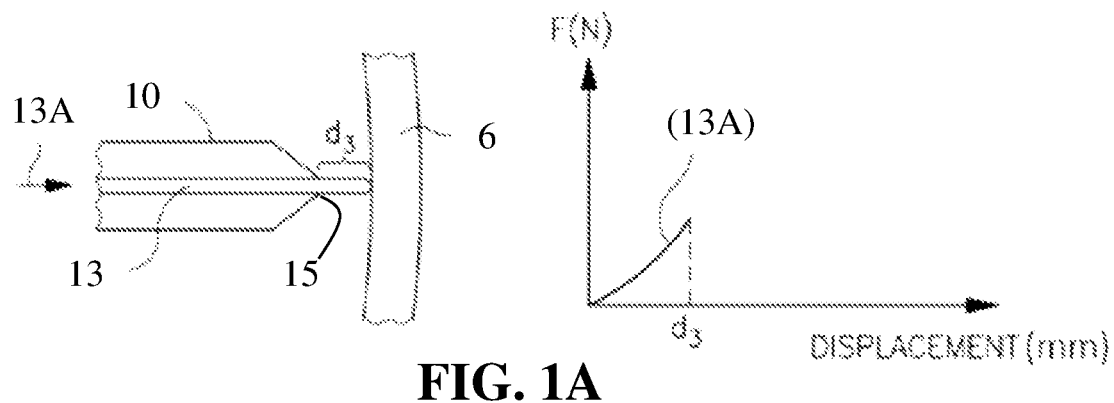
FIGS. 1A-1C schematically illustrate exemplary scenarios in using a pusher-probe to safely enter the epidural space, according to some embodiments of the invention.
Figure 1B:
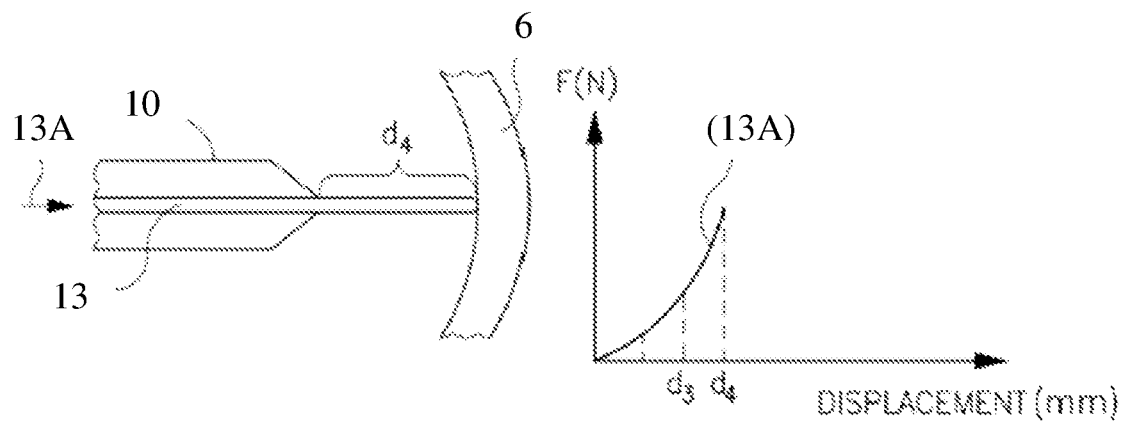

The present invention, in some embodiments thereof, relates to techniques (systems, methods) for identifying a target anatomic location in a subject's body, including of humans or other mammals, and for optionally delivering a medicinal substance to the target anatomic location in the subject's body, or for performing a different treatment or effect to a target tissue, following transtissual progression (penetrating and optionally cutting through layers of body tissue) of a medical device and reaching the body tissue mass with a distal tip thereof. Some embodiments of the present invention involve acquiring mechanical properties of body tissue mass following the medical device transtissual progression. In exemplary embodiments, the medicinal substance is, or includes, a drug, for example, an anesthetic agent, and the target anatomic location is epidural space in the subject's body.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. The following exemplary embodiments may be illustratively described in the context of exemplary needle placement procedures for ease of description and understanding. However, the invention is not limited to the specifically illustratively described devices and methods, and may be adapted to various clinical applications without departing from the overall scope of the invention.

In the relevant field(s) of the invention, application of prior art techniques has limitations, and may be accompanied by various possible errors, especially during transtissual progression before reaching target bodily matter or anatomic location. For example, during transtissual progression of an epidural needle in a patient, the needle tip may encounter voids or fat deposits characterized by low resistance similar to that found in an epidural space. Epidural needle systems may be configured to automatically stop progressing and hold in-place upon entering such low resistance (void or fat deposit) bodily matter or anatomic location. In such cases, a physician needs to analyze the situation in order to confidently determine that the epidural needle tip is not in the target bodily matter or anatomic location. Thereafter, the physician would need to override the automatic needle stop or hold in-place mode, and continue manipulating the epidural needle delivery apparatus, in order for the needle to eventually reach the target epidural bodily matter or anatomic location. Such additional procedures relating to analyzing the situation and overriding the needle stop or hold in-place mode may involve additional sources of error, as well as reduce overall efficiency in administration of medicinal material to the correct target epidural bodily matter or anatomic location in the patient.

At least some of the various limitations and problems associated with prior art techniques relating to needle injection type medicinal substance or/and material delivery to patients are addressed, and overcome by, at least some embodiments of the herein disclosed invention.

Some embodiments of the present invention relate to techniques (systems and associated methods) that include several structural and functional characteristics and properties (and special technical features thereof) which lead to highly accurately and precisely (reproducibly) identifying a target anatomic location penetrated to by a medical device following transtissual progression (advancement) thereof through a body tissue mass. Such highly accurate and precise target anatomic location identification is attained, in part, by highly accurately and precisely acquiring mechanical properties of a body tissue mass (matter) following transtissual progression (advancement) of the medical device and reaching the body tissue mass with a distal tip thereof. Such exemplary embodiments of the invention involve allowing an efficient and seamless type of transtissual progression (advancement) of a needle, for example, an epidural needle, until reaching the target body mass (matter) and target anatomic location, while avoiding, or at least minimizing, generation of false or/and potentially false feedback information and data.

In some embodiments, the medical device is a specially designed, constructed, and operative 'pusher-probe' whose distal end is provided in a cannula lumen. In exemplary embodiments, the pusher-probe is a noncompliant rigid member, particularly configured and suitable for 'pushing (probing) through' and 'mechanically manipulating' (deforming) soft tissue it encounters and progresses (advances) through, in a manner whereby the pusher-probe exhibits minimal to no deformation.

Exemplary embodiments of the system include a specially designed, constructed, and operative 'extending mechanism' that includes a cam member and associated components configured for enabling selective traveling of the distal end of the medical device (for example, the pusher-probe) in a cannula lumen, such that the medical device distal end (pusher-probe distal end) becomes repositioned between a retracted position and a protruding position.

Exemplary embodiments of the system include a data-information analyzing device having a specially designed, constructed, and operative 'triggering mechanism' that includes a 'winged' hub member and associated components thereof.

Implementation of some embodiments of the invention enable safely positioning a medical device, such as an introducer, a stylet, a cannula, or a pusher-probe type member, inside mammalian tissue. The term 'pusher-probe', as used herein, in a non-limiting manner, refers to a component (member) exhibiting structural and functional characteristics, properties, and features associated with both 'pushing' and 'probing'. Particularly, in the context of having structure and function (operation) suitable for 'pushing' tissue, and also particularly, in the context of having structure and function (operation) suitable for 'probing' tissue.

According to an aspect of the invention, provided are techniques (exemplary system and method embodiments) for identifying a target anatomic location penetrated to by a medical device distal tip following transtissual progression thereof through a body tissue mass. According to an aspect of the invention, provided are techniques (exemplary system and method embodiments) for acquiring mechanical properties of a body tissue mass following transtissual progression of a medical device and reaching the body tissue mass with a distal tip thereof.

In exemplary embodiments, the system includes a hollow introducer, or a cannular member, having a longitudinal axis and a distal end and a pusher-probe, or a stylet, movable through a lumen inside the cannular member and arranged to be controllably pushed out of the distal end of the cannular member and against the mammalian tissue. The cannular member may include any of: a thin needle, a Veress needle, an epidural needle, a biopsy needle, a trocar, a cannula, a catheter, a Tuohy type needle, a spinal needle, a pencil point needle, a guidewire, a surgical instrument and a sharp tool.

In some embodiments, the pusher-probe includes an inner lumen and at least one distal orifice arranged to introduce fluid into the tissue to sense tissue pressure. In exemplary embodiments, the pusher-probe is structurally noncompliant or/and rigid at least to a degree it maintains axial stiffness to resistive forces applied from incoming tissue mass in contact with its distal end. Optionally and alternatively, the pusher-probe is configured to receive its pushing strength or/and incompliance to change in shape or/and in size from the surrounding walls of the cannular member, and be flexible upon extending fully or partially, or if further than a certain threshold length beyond the cannular member. In exemplary embodiments, the pusher-probe is configured and functions as a convey for a medicinal substance (e.g., in a form of a catheter) after withdrawal of the cannular member.

The phrase "medicinal substance", as used herein, in a non-limiting manner, refers to a substance having properties of medicine. For example, the medicinal substance may be, or include, a pharmaceutical substance, such as a pharmaceutical product, preparation, or formulation. For example, the medicinal substance may be, or include, a therapeutic substance having therapeutic (treatment or healing) properties. For example, the medicinal substance may be, or include, filling material for a body part, such as filling material for a bone or other body part. In exemplary embodiments, the medicinal substance is, or includes, a drug, for example, an anesthetic agent, and the target anatomic location is epidural space in the subject's body.

The pusher-probe is optionally arranged to perform a push-pull movement, along with enabling measurement of the force applied on the pusher-probe by the mammalian tissue per the displacement of the mammalian tissue, in order to facilitate determining the type of tissue by a data-information processing/programming unit. For example, the pusher-probe may have a blunt tip arranged to enable a pushing action without cutting of mammalian tissue, although in some instances it may be advantageous to provide a pusher-probe arranged to penetrate a tissue ahead of the cannular member, for example, in order to increase the tactile feedback of the operator of the cannular member. In some embodiments, the pusher-probe is arranged to detect bony structures ahead of the cannular member in order to protect the cannular member of being damaged by bony structures.

In some embodiments, the system includes an actuator which is optionally fixated to the cannular member. In some embodiments, the actuator is arranged to controllably actuate and push the pusher-probe out of the distal end of the cannular member or pull it back towards the distal end. Optionally, the actuator is configured to immediately pull back, or at least allow an immediate retraction of, the pusher-probe following a protruding position of the pusher-probe distal end, optionally, to a maximal protrusion length.

Optionally, the actuator is arranged to actuate and push the pusher-probe against the tissue in a first predefined velocity, and to pull it back in a second predefined velocity. The second predefined velocity is optionally higher than 5 mm per second to enable fast retraction of the mammalian tissue towards the advancing cannular member in order to facilitate reducing the overshoot of the cannular member during penetration into the mammalian tissue.

A sensor may be provided, arranged to sense and measure a force or a pressure required to push the pusher-probe against the mammalian tissue. The system may further include a data-information processing/programming unit arranged to record and analyze measurements and determine therefrom a type of the mammalian tissue and transitions between different mammalian tissues and cavities.

Figure 1C:
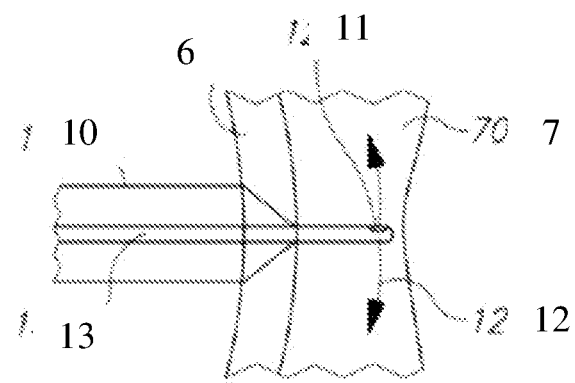
Figure 2A:
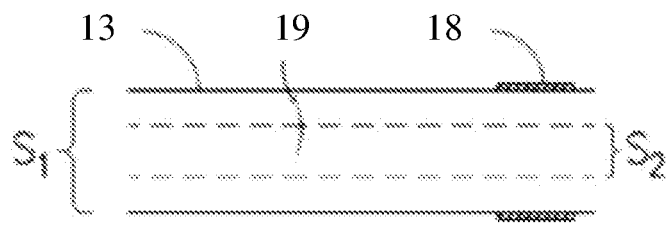
FIGS. 2A-2D schematically illustrate exemplary pusher-probe configurations, according to some embodiments of the invention.
Figure 2B:
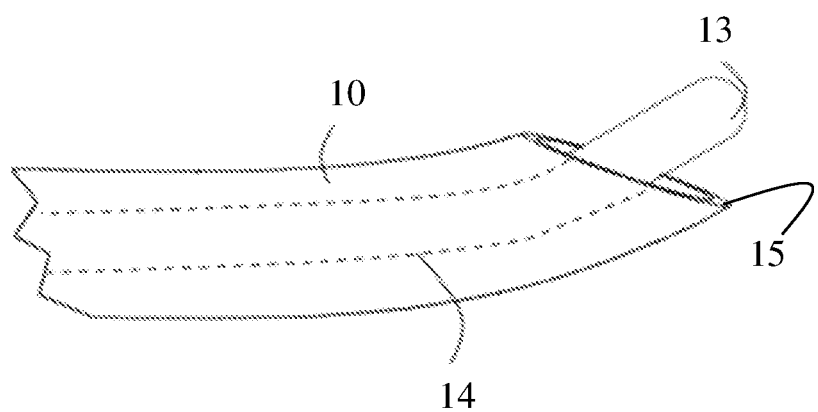
Figure 2C:
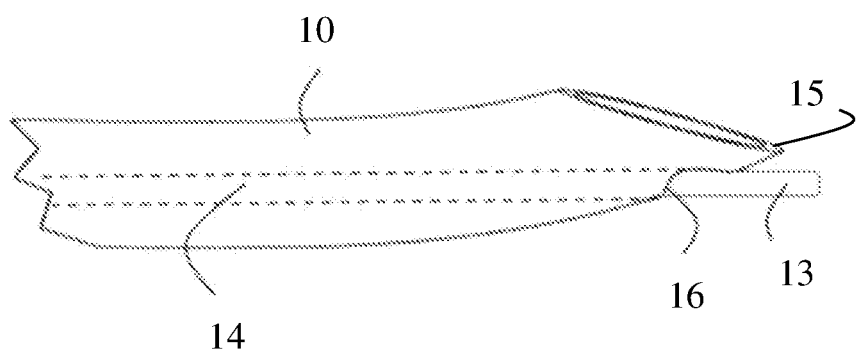

Referring now to the drawings, FIGS. 1A-1C, and FIGS. 2A-2D, schematically illustrate exemplary scenarios of using a pusher-probe 13 to safely enter an epidural space 7, according to some embodiments of the invention. Pusher-probe 13 may be applied from within a needle or a cannular member 10, e.g., pushed through needle inner lumen or cannular lumen 14, or from within any sharp introducer such as a trocar, veress needle, Tuohy needle, pencil point needle, quincke needle, vascular cannulation or surgical tool. In exemplary embodiments, an actuator (actuation mechanism) actuates and controls the advancement (progression, protrusion) of pusher-probe 13 by applying an appropriate force 13A. In exemplary embodiments, the actuator is fixated to cannular member. In exemplary embodiments, pusher-probe 13 can be pushed through a needle having a curved tip, such as a Tuhoy needle (FIG. 2B), or through an additional opening 16 in the curved region of the needle (FIG. 2C).

In exemplary embodiments, pusher-probe 13 may be advanced to push resilient tissue such as ligamentum flavum tissue 6 or other types of tissues. Pusher-probe 13 may be sufficiently blunt so as to allow measuring tissue resistance when tissue is being pushed (displaced) to a certain distance (graphs FIGS. 1A, 1B) without penetrating the tissue.

Pusher-probe 13 may be reciprocally/repeatedly and controllably pushed forward (13A) ahead of cannular member 10 and then pulled back towards cannular member tip 15 to measure tissue resistance to manipulation. The push-pull movement may be performed when cannular member 10 is static or as it advances. The push-pull movement may also be continuous along the penetration through different tissues, or may be event-driven, for example, by a decision of the operator or by reaching a certain reading threshold.

An actuator may be applied to push (advance) pusher-probe 13 at a constant velocity and pull it backwards with the same velocity, or with a different velocity. For example, applied pushing (progression or advancement) velocity may be in a range of between about 1 mm per second and about 5 mm per second, while pulling velocity may be in a range of between about 5 mm per second and about 20 mm per second. Pusher-probe 13 may controllably traverse a distance in a range of between about 1 mm and about 5 mm at a constant velocity, and a controlling system may measure the force applied on pusher-probe tip 15 by tissue as a function of the traversed distance. The measurements may be used to indicate tissue type and deformation and may be used to monitor the advancement of cannular member 10. For example, the measurements may be compared to known tissue responses of ligamentum flavum 6). A controlling system may include a sensor (for instance, a load cell). One advantage of such a force measurement is measuring only the forces applied on tip or distal end of pusher-probe 13 by adjacent tissue, and optionally excluding, for example, the friction between cannular member 10 and tissue in contact. The measurement could be also sent to a data-information processing/programming unit in order to further analyze the data with mathematical tools, for example, to calculate the force or work required by the pusher-probe 13 to push the tissue or/and the resistive force applied by the incoming tissue mass to distal end of pusher-probe 13 during tissue manipulation (e.g., during protrusion and/or retraction of the pusher-probe with respect to distal end of cannular member 10).

In yet another embodiment, the controlling system maintains preconfigured force applied on pusher-probe 13, by pushing pusher-probe 13 further ahead of cannular member 10 when measured force drops below the preconfigured force, or by pulling pusher-probe 13 backwards towards cannular member tip 15 when measured force exceeds the preconfigured force. By further analyzing pusher-probe traversed distances, the type of tissue engaged with pusher-probe 13 can be determined.

Pusher-probe 13 can also be advantageous in detecting bony structures ahead of cannular member 10. When cannular member 10 is facing a bony structure, a measurement of force applied on pusher-probe 13 during a pushing movement will be substantially large with respect to other possible tissue resistance recordings, thus indicating the existence of a bony structure ahead of cannular member 10. In an epidural injection, for example, such indication will assist the operator in adjusting the onward path of cannular member 10 before reaching a bony structure that can harm the cannular member tip and risk the entire procedure.

Figure 2D:
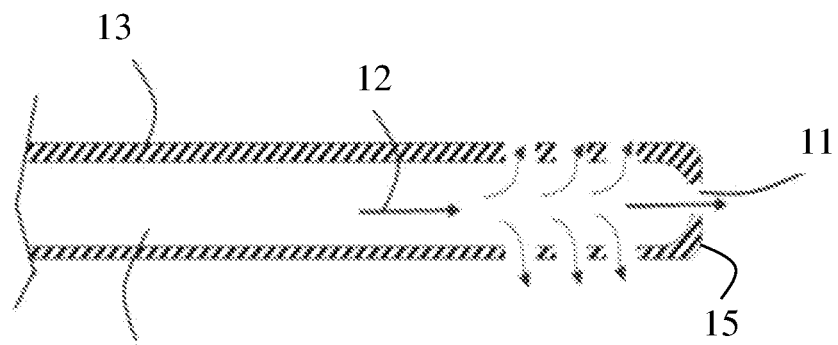

In exemplary embodiments (for example, as illustrated in FIGS. 1C and 2D), pusher-probe 13 may include an internal pusher-probe lumen for delivering fluid 12, for example, a medication or an inert substance, to carry out the loss of resistance technique (LORT), through an opening 11 at the end of pusher-probe 13. Pusher-probe 13 may include several lateral orifices to deliver fluid 12 in several directions (as shown in FIG. 2D). Such measurement provides epidural space identification with cannular member penetration.

In another embodiment, pusher-probe 13 may be used to perform the penetration into epidural space 7 ahead of cannular member 10. Such an embodiment may be beneficiary since pusher-probe 13 smaller outer diameter will reduce the tissue trauma during penetration in comparison to a standard needle, such as in the Tuohy needle configuration (shown in FIG. 2B), optionally, having an outer diameter in a range of between about 1.2 mm and about 1.6 mm. Even in case pusher-probe 13 penetrates dura mater, the damage is much smaller than done by a penetration of cannular member 10. In exemplary embodiments, pusher-probe 13 in the form shown in FIG. 2A may have a diameter S1 in a range of between about 0.8 mm and about 0.9 mm, and an internal lumen 19 thereof may have a diameter S2 in a range of between about 0.5 mm and about 0.7 mm.

Pusher-probe 13 may be made of any biocompatible material known in the art, such as different kinds of plastic, nylon, stainless steel or Nitinol.

Pusher-probe 13 may be configured to receive its pushing strength from surrounding cannular member, and be flexible upon extending over a certain threshold beyond cannular member 10, thus adding another safety layer in preventing dangerous overshooting during penetration. For example, pusher-probe 13 may be configured to become flexible when extending, for example, 4 mm ahead of cannular member tip 15, so that when cannular member 10 is static and pusher-probe 13 is being pushed forward, maximum overshoot will not exceed 4 mm. In exemplary embodiments, pusher-probe 13, as in configuration of FIG. 2A, may be strengthened by a supportive member 18 which may be in a form of a ring or a reinforcing spring.

In exemplary embodiments, pusher-probe 13 may be configured as a catheter (e.g., controllable via a Luer fitting) that may be advanced as described into epidural space 7 and then be left there after removal of cannular member 10 (in case pusher-probe strength is provided by cannular member 10, cannular member removal leaves pusher-probe 13 as flexible catheter 13 in the epidural space). In one embodiment, after detection of epidural space 7 a locking mechanism of pusher-probe 13 may be unfastened and an actuator may be disconnected hence leaving pusher-probe 13 and cannular member 10 inside epidural space 7. Then, cannular member 10 may be removed, and pusher-probe 13 may be connected to an extension tube that can be used as a catheter for administered substances into epidural space 7. In another embodiment, upon detection of epidural space 7, pusher-probe 13 may be removed and a medication be administered either directly through cannular member 10 using a syringe, or through an epidural catheter that may be threaded through cannular member 10.

Alternatively, a medication may be administered through pusher-probe 13 or/and through cannular member 10 while pusher-probe 13 is still within cannular member 10.

Reference is made to FIGS. 3A-3F which schematically illustrate partial cut views of an exemplary medical device 5, and exemplary scenarios representing steps in an exemplary method for using a system 20 for acquiring mechanical properties of body tissue mass (such as of a first body tissue mass BTM1 and a second body tissue mass BTM2 located distally to BTM1) following transtissual progression of medical device 5, with a distal tip thereof, according to some embodiments of the invention. Medical device 5 optionally includes a needle, such as an epidural needle. During transtissual progression, medical device 5 may encounter body tissue masses of any type or any anatomic location (including spaces or gaps). Such tissue or anatomic locations may include at least one of skin, subcutaneous tissue, muscle tissue, artery wall tissue, vein wall tissue, fascia, adipose tissue, intestine, cartilage, ligamentum flavum, epidural space, or tissues adjacent or within it, and dura mater.

System 20 includes a cannular member 21 enclosing a cannula lumen 22 opened at a cannula distal end 23. In case that medical device 5 includes a needle, then, for example, medical device 5 includes cannular member 21 while cannula distal end 23 includes a sharp edge. In some such embodiments, cannular member 21 is one of a Tuohy needle, a Crawford needle, a Hustead needle, a Weiss needle, Sprotte Spezial needle, a Wagner needle, a Cheng needle, a Crawley needle, a Foldes needle, a Bell needle and an Eldor needle.

A pusher-probe 24 having a pusher-probe distal end 25 is provided in cannula lumen 22. In exemplary embodiments, pusher-probe 24 is a noncompliant rigid member, particularly configured and suitable for 'pushing through' and 'mechanically manipulating' (deforming) soft tissue it encounters and progresses (advances) through, in a manner whereby the pusher-probe 24 exhibits minimal to no deformation. Optionally, and as shown in FIGS. 3A-3F, pusher-probe 24 includes an elongated member 31 ending in the pusher-probe distal end 25, and slidable in cannula lumen 22. Elongated member 31 is, for example, incompressible so as not to yield to clenching forces, meaning, that under normal clenching forces (such as forces developed by manually pushing a blunt cannula in a body), under which it is not supposed to yield or break, the elongated member 31 shall not compress about its long axis. In some embodiments, pusher-probe 24 is rigid, and in other embodiments it is elastically or plastically bendable.

Pusher-probe distal end 25 is positionable from a retracted position 26 (shown in FIG. 3A), being mostly or fully enclosed within cannula lumen 22, to a protruding position 27 (shown in FIG. 3B), in which pusher-probe distal end 25 protrudes out of cannula distal end 23 to a length up to a maximal protrusion length. In some embodiments, when cannula distal end 23 is in front of the first body tissue mass BTM1, pusher-probe distal end 25 is configured to mechanically manipulate a portion P1 of the body tissue mass during repositioning to retracted position 26 or/and to protruding position 27. In some embodiments, mechanical manipulation is achieved by thrusting pusher-probe distal end 25 into mass portion P1 and then releasing contact with it (as shown in FIGS. 3B and 3C, respectively).

Pusher-probe distal end 25 is, for example, sized or/and shaped such to avoid penetration into the body tissue mass during repositioning(s) thereof. In some such embodiments, pusher-probe distal end 25 is blunt (having a broad or rounded end) or/and dull (not having a sharp edge or point) in order to harmlessly manipulate a tissue portion in direct contact.

Figure 3A:
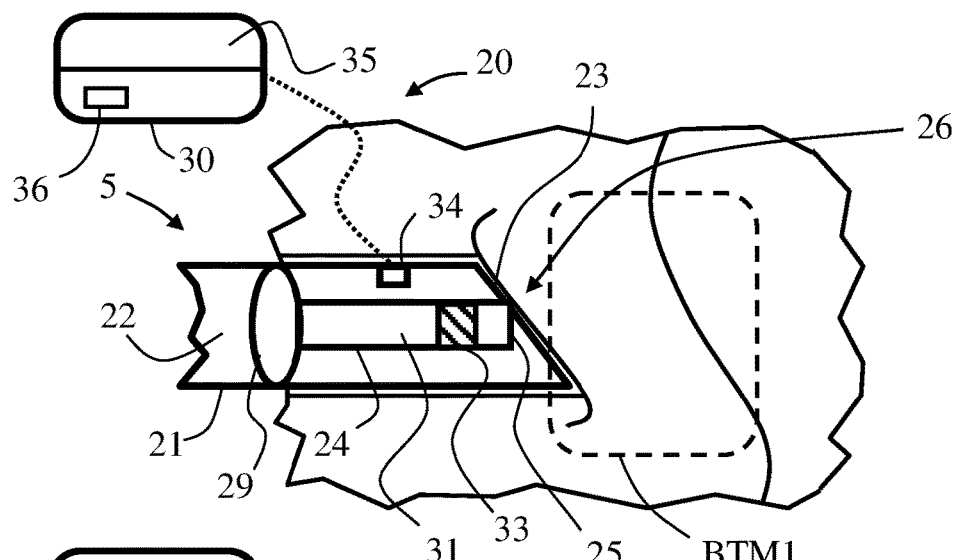
FIGS. 3A-3F schematically illustrate partial cut views of an exemplary medical device, and exemplary scenarios representing steps in an exemplary method for using a system for acquiring mechanical properties of body tissue mass following transtissual progression of the medical device, according to some embodiments of the invention.
Figure 3B:
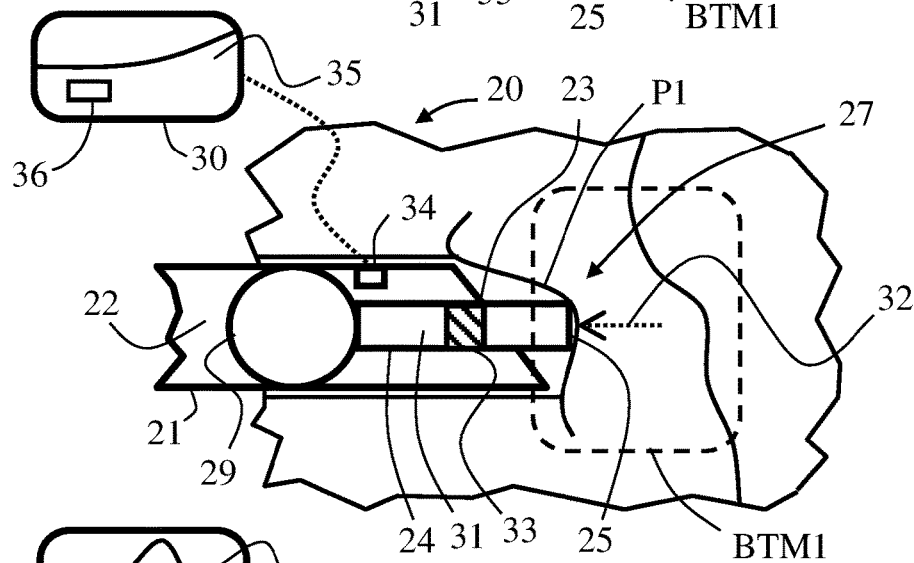
Figure 3C:
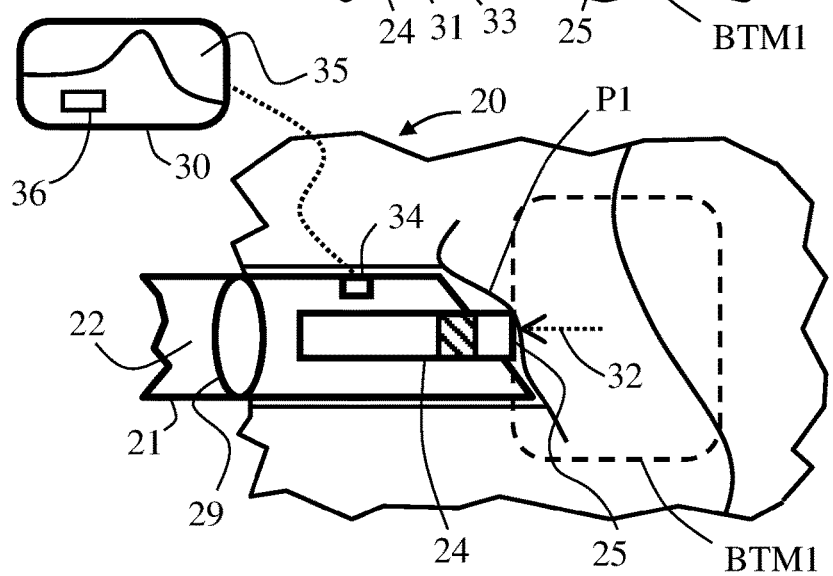

In some embodiments, an actuation mechanism 29 is provided as part of system 20 and is adapted to actuate protrusion of pusher-probe distal end 25 relative to cannula distal end 23, and to allow an immediate follow-up retraction of pusher-probe distal end 25 if it is under a retractive force 32 (as shown in FIG. 3C). In some embodiments, actuation mechanism 29 is adapted for automatic reciprocal repositioning of pusher-probe distal end 25 between retracted position 26 and protruding position 27, optionally, during a defined actuation period. A reciprocal repositioning includes a plurality of a stroke cycles, each including a single forward stroke from the retracted position to the protruding position and a single backward retraction from the protruding position to the retracted position. In some embodiments, the stroke cycles have a frequency in a range of between about 1 Hz and about 20 Hz, optionally, between about 4 Hz and about 10 Hz. Optionally, the reciprocal repositioning facilitates unhindered transtissual progression with medical device 5 through soft tissue with a progression velocity equal to or less than about 5 mm per second, optionally, equal to or less than about 3 mm per second. In some embodiments, the sensed effect is sampled with a sampling rate in a range of between 50 Hz and about 1000 Hz, optionally, between about 100 Hz and about 500 Hz.

Other than immediate information about a current sensed data of the manipulated tissue or reaction (or absence of reaction), using a small cycle duration combined with a high sampling rate, can generate processed and analyzed information, based on the captured data, which can be indicative of currently penetrated and incoming tissue masses, as well as of possible anticipated and immediate indications for penetrating a target or an unwanted tissue, organ or anatomic location.

Another beneficial feature is the continuous uninterrupted travel of the epidural needle until reaching the target bodily tissue mass or anatomical location. The use of substantially low cycle durations allows an overall relatively uninterrupted needle progression since that although each protruding position of pusher-probe thrusting into incoming tissue may result in a minute brake, the immediate pusher-probe retraction actually maintains a continuous customary progression rate.

A sensor 34 may be adapted to correlate a mechanical property of the (manipulated) body tissue mass with a sensed effect resulting from a reaction of the body tissue mass to the mechanical manipulation. The mechanical property may be force-to-tissue deflection profile, Young modulus, stiffness, failure or yield properties, stress and strain, of the body tissue mass portion (P1).

The reaction of the body tissue mass may include retractive force 32 if it is applied by the body tissue mass at a contact area with pusher-probe distal end 25, if, for example, it possesses elastic properties. Optionally, alternatively or additionally, as shown, for example, in FIGS. 3A-3B, and in FIGS. 3D-3E, a retractive force is applied by a retraction spring 33 compressible during pusher-probe distal end 25 repositioning from retracted position 26 to protruding position 27.

In some embodiments, pusher-probe distal end 25 in protruding position 27 is distanced from cannula distal end 23 by at least about 0.2 mm, optionally, by at least about 0.5 mm, optionally, by at least about 1 mm, or higher, or lower, or an intermediate value. In some embodiments, the maximal protrusion length is equal to or less than about 10 mm, optionally, equal to or less than about 5 mm, optionally, equal to or less than about 3 mm, optionally about 2.5 mm, or higher, or lower, or an intermediate value. In some embodiments, a distance of pusher-probe distal end 25 to cannula distal end 23 in protruding position 27 is variable. Optionally, it is determined according to the mechanical property of the (manipulated) body tissue mass. In some embodiments, system 20 is configured such that the distance is in a range of between about 0.2 mm and about 5 mm, optionally, between about 0.5 mm and about 3 mm. Optionally, protruding position 27 is preset in response to previous sensed effect(s). The sensed effect may be correlated with at least one force component of retractive force 32, such as an axial force component acting along elongated member 31 during at least forward repositioning (i.e., extension) of pusher-probe distal end 25.

Sensor 34 may be or include a force sensor, a motion sensor, a proximity sensor or any other sensor type. In some embodiments, sensor 34 is a force sensor configured to respond to the sensed effect correspondingly to the force component. Optionally, alternatively or additionally, sensor 34 is a motion sensor configured to respond to the sensed effect associated with a motion of a system component within cannula lumen 22 during repositioning of pusher-probe distal end 25; the system component may be one of pusher-probe 24, pusher-probe distal end 25, a spring, a bellow, an elastic member and a component connected to pusher-probe 24. The motion of the system component may include at least one of sliding, extension and compression along cannula lumen 22 length or portion thereof.

In some embodiments, a data-information analyzing device 30 is provided and includes an integrated circuit or a data-information processing/programming unit programmed (in FIGS. 3A-3F, generally exemplified by component 36 shown inside data-information analyzing device 30. Integrated circuit 36 or data-information processing/programming unit 36 is configured to assign a numerical value to the sensed effect. Data-information analyzing device 30 may also include a memory, wherein data-information processing/programming unit 36 is programmed to store a database of previous numerical values assigned to previous sensed effects or/and other stored information, and to compare the numerical value of the sensed effect to the database. Data-information analyzing device 30 may be a portable device, operatively connectable (linkable), via a wired configuration or/and a wireless configuration, to sensor 34 (in FIGS. 3A-3F, generally exemplified by the dashed line between data-information analyzing device 30 and sensor 34). Alternatively, data-information analyzing device 30 may be embedded in medical device 5, in cannular member 21 or in pusher-probe 24.

In some embodiments, and as shown, system 20 includes a signifying device 35 linked with data-information analyzing device 30 or/and directly with sensor 34. Signifying device 35 optionally includes at least one of a screen, a LED, a printer, an audio signal transducer, a tactile signal transducer, and an audiovisual transducer, and optionally, is adapted to signify a tissue mass property indicator indicative of the sensed effect. Optionally, alternatively, or additionally, signifying device 35 is adapted to signify a property change indicator indicative of a change between the sensed effect and a baseline; the baseline may be a stored information or/and a value linked to previous measurement.

In some embodiments, system 20 includes or is connectable to a syringe (for example, syringe 152 shown in FIGS. 13A and 13B), such as an LOR syringe. Such syringe may be connectable to cannular member 21, or that cannular member 21 may be provided in the syringe or in a needle connectable to the syringe.

An exemplary embodiment of a method for acquiring mechanical properties of body tissue mass using system 20 includes the following exemplary steps (procedures) [not necessarily in same order] and associated components for implementing thereof.

Transtissueally penetrating a soft tissue with cannular member 21 until reaching an unpenetrated body tissue mass BTM1 with cannula distal end 23 (as shown in FIG. 3A).
  Mechanically manipulating body tissue mass BTM1 by repositioning pusher-probe distal end 25 to protruding position 27 out of the cannula distal end 23 (as shown in FIG. 3B).
  Mechanically manipulating is performed, for example, in a manner non-traumatic to the body tissue mass BTM1, and optionally, includes at least one of laterally stretching, distally compressing, distally thrusting, distally curving, distally bending, distally pushing and rotationally twisting the body tissue mass, or/and immersing, fully or partially, in the body tissue mass, with pusher-probe distal end 25.

Allowing pusher-probe distal end 25 to immediately retract up to retracted position 26 (FIG. 3C).

Recording a sensed effect resulting from the mechanical manipulation by pusher-probe 24 causing the body tissue mass BTM1 to react thereto.

Correlating the recorded sensed effect with a mechanical property of the body tissue mass BTM1.

Pusher-probe 24 may be axially supported by an elastic member (e.g., a spring, such as retraction spring 33) configured to continuously force pusher-probe distal end 25 to proximally shift within cannula lumen 22 up to retracted position 26, such that pusher-probe distal end 25 immediately retracts following allowing immediate retraction of pusher-probe distal end 25. Optionally, alternatively or additionally, pusher-probe distal end 25 is configured to spring back following the allowing in response to elastic properties of the body tissue mass (FIG. 3C).

Signaling a tissue mass property indicator indicative of the sensed effect or/and a property change indicator indicative of a change between the sensed effect and a baseline (as plotted by signaling device 35 in FIGS. 3B and 3C, comparing to null signal shown in FIG. 3A).

Optionally, connecting a syringe to cannular member 21 and applying the syringe with cannular member 21 to facilitate performing of a loss of resistance technique at an anatomic location inside of or beyond body tissue mass BTM1.

Repeating (manually or automatically), optionally, reciprocally, the transtissueally penetrating, the mechanically manipulating, the allowing, or/and the recording, until, optionally, detecting a signal indicative of a target tissue or of a space adjacent to or between tissues.

Figure 3D:
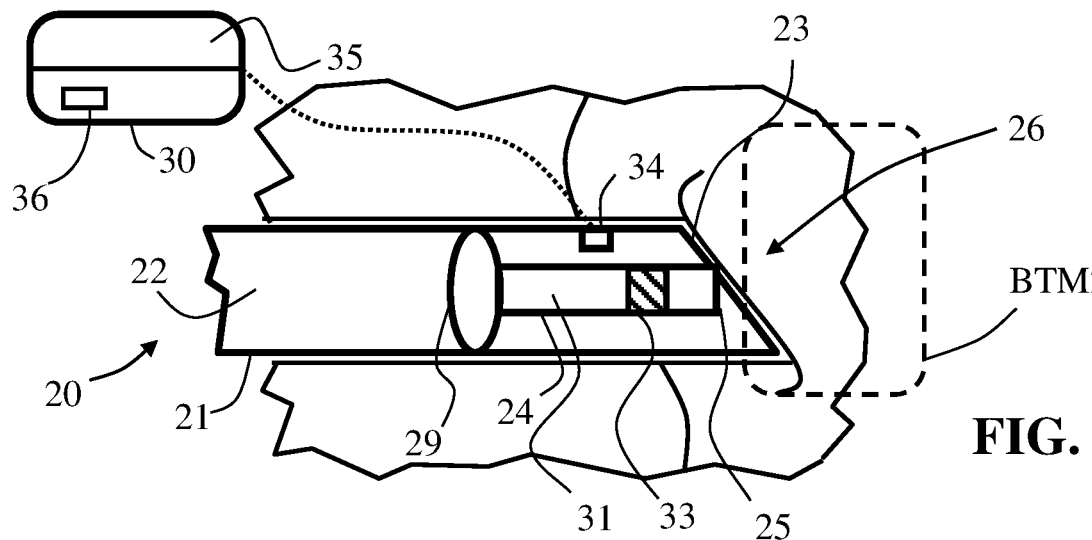
Figure 3E:
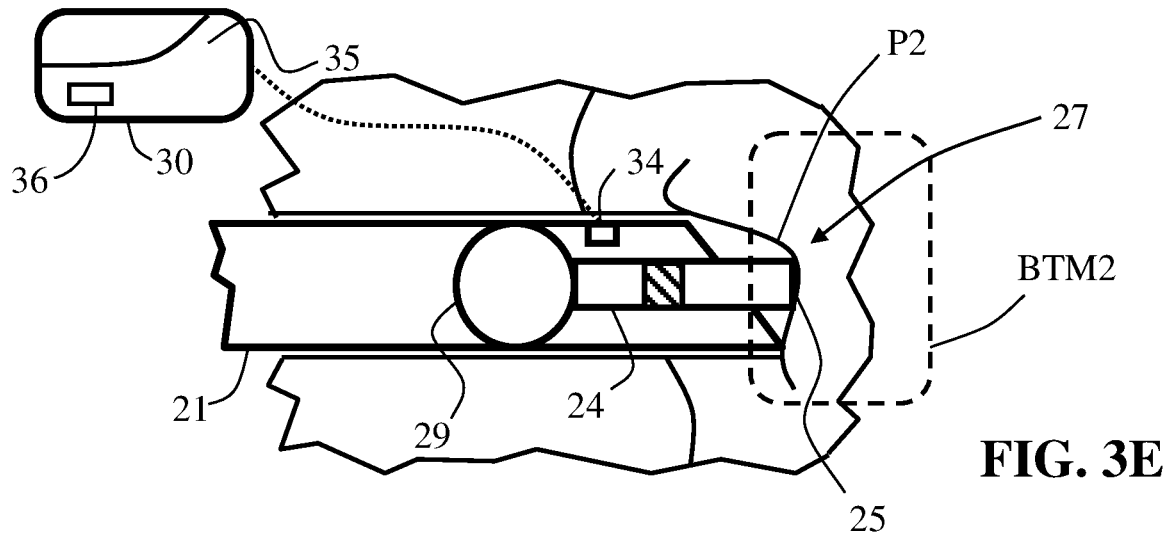
Figure 3F:
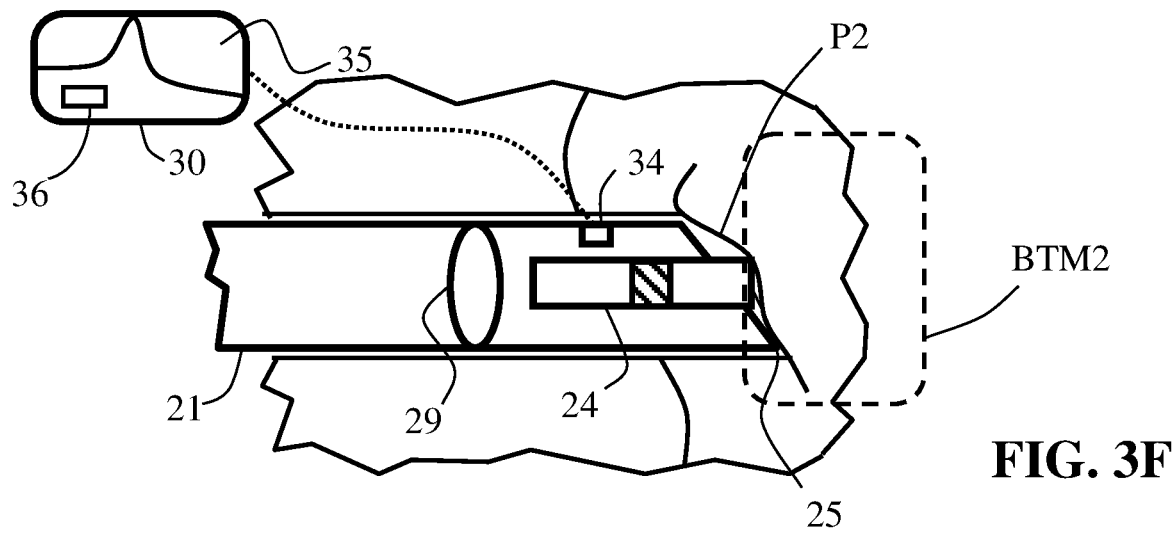

FIGS. 3D-3F illustrate repeated steps, as described above, following further transtissual progression by cannula distal end 23 until reaching portion P2 of second body tissue mass BTM2 (FIG. 3D). Body tissue mass BTM2 is mechanically manipulated by repositioning pusher-probe distal end 25 to protruding position 27 out of the cannula distal end 23 (FIG. 3E). Pusher-probe distal end 25 is then allowed to immediately retract up to retracted position 26 (FIG. 3F).

In additional exemplary embodiments of the method for acquiring mechanical properties of body tissue mass using system 20, until or/and after reaching a target tissue or intertissual space, pusher-probe 24 may have the capacity and configuration to serve as a local delivery device for immediate or prolonged medicinal or therapeutic treatments. In such exemplary embodiments, pusher-probe 24 encloses a pusher-probe lumen extending therealong. Optionally, the method includes at least one of the following additional steps (procedures) [not necessarily in same order] and associated components for implementing thereof.

Delivering a fluid/substance or a medical tool across or through pusher-probe 24 into or adjacent to the target tissue or the space adjacent to or between tissues while pusher-probe 24 is enclosed mostly or fully inside cannular member 21.

Withdrawing pusher-probe 24 from within cannular member 21, and delivering a fluid/substance or a medical tool through cannular member 21 into or adjacent to the target tissue or the space adjacent to or between tissues.

Withdrawing cannular member 21 over pusher-probe 24, and delivering a fluid/substance (e.g., medication) or a medical tool across or through pusher-probe 24 (e.g., via the pusher-probe lumen) into or adjacent to the target tissue or the space adjacent to or between tissues.

Reference is now made to FIGS. 4A-4D which schematically illustrate exemplary mechanical manipulations of differently supported body tissue mass portions using an exemplary system 40, according to some embodiments of the invention. System 40 may be similar to or different than system 20, or include similar or different components thereto. System 40 includes a cannular member 41 enclosing a cannula lumen 42 opened at a cannula distal end 43. A pusher-probe 44 having a pusher-probe distal end 45 is provided in cannula lumen 42. In exemplary embodiments, pusher-probe 44 is a noncompliant rigid member, particularly configured and suitable to push through and mechanically manipulate (deform) soft tissue it encounters and progresses (advances) through, while exhibiting minimal to no self-deformation. Pusher-probe 44 includes an uncompressible elongated member slidable it cannula lumen 42. Pusher-probe distal end 45 is positionable from a retracted position 46 (shown in FIGS. 4A and 4C), being mostly or fully enclosed within cannula lumen 42, to a protruding position 47 (shown in FIGS. 4B and 4D), in which pusher-probe distal end 45 protrudes out of cannula distal end 43 to a length up to a maximal protrusion length. Pusher-probe distal end 45 is configured to mechanically manipulate a portion (such as portion P3 in FIGS. 4A-4B and portion P4 in FIGS. 4C-4D) of the body tissue mass during repositioning to retracted position 46 or/and to protruding position 47. In some embodiments, mechanical manipulation is achieved by thrusting pusher-probe distal end 45 into any of the mass portions and then releasing contact with it. As demonstrated in FIGS. 4A-4B, system 40 is configured such that upon the body tissue mass being distally supported by a denser object, such as a bone BN, the body tissue mass portion P3 compresses against the denser object when thrust into with pusher-probe distal end 45. As demonstrated in FIGS. 4C-4D, system 40 is configured such that upon the body tissue mass being distally opened to a space, such as epidural space EPS, the body tissue mass portion P4 curves into the space when thrust into with pusher-probe distal end 45. These different behaviors will be reflected in the recorded sensed effects, so a sensor or/and a data-information analyzing device (for example, sensor 34 or/and data-information analyzing device 30 described above and shown in FIGS. 3A-3F) can be set to assess adjacent bony tissue or/and spaces.

FIGS. 5A-5B schematically illustrate an exemplary system 50 including an exemplary axially expandable pusher-probe, according to some embodiments of the invention, as opposed to the previously described pusher-probe designs with a sliding an uncompressible elongated member. Otherwise, system 50 may be similar to or different than system 20 or/and system 40, or include other similar or different components thereto. System 50 includes a cannular member 51 enclosing a cannula lumen 52 opened at a cannula distal end 53. A pusher-probe 54 having a pusher-probe distal end 55 is provided in cannula lumen 52. In exemplary embodiments, pusher-probe 54 is a noncompliant rigid member (when internally pressurized to a minimal predefined value), particularly configured and suitable to push through and mechanically manipulate (deform) soft tissue it encounters and progresses (advances) through, while exhibiting minimal to no self-deformation. Pusher-probe 54 includes a portion 58 axially expandable and compressible in cannula lumen 52, such that pusher-probe distal end 55 is positionable from a retracted position 56 (shown in FIG. 5A), being mostly or fully enclosed within cannula lumen 52, to a protruding position 57 (shown in FIG. 5B), in which pusher-probe distal end 55 protrudes out of cannula distal end 53 to a length up to a maximal protrusion length. Portion 58 is optionally restricted from radial expansion during the repositioning, optionally, by using expansion limiting means on its boundaries. Pusher-probe distal end 55 is configured to mechanically manipulate a portion of the body tissue mass during repositioning to retracted position 56 or/and to protruding position 67. In some embodiments, mechanical manipulation is achieved by thrusting pusher-probe distal end 55 into any of the mass portions and then releasing contact with it. A sensor 59 may be used to capture a sensed effect, for example, by sensing variable pressure or force reacting on portion 58, or/and a change of length thereof.

FIGS. 6A-B schematically illustrate exemplary systems 60 and 65 including exemplary pusher-probes configured to allow passage of fluid therethrough and thereacross, respectively, according to some embodiments of the invention. Any of systems 60 and 65 may be similar to or different than any of system 20, system 40 or/and system 50, or include other similar or different components to any of them. System 60 (FIG. 6A) includes a pusher-probe 61 enclosed in a cannula 62 and including an inner pusher-probe lumen 63 allowing passage of fluids or/and properly sized medical tools therethrough, when in a retracted position or/and when in a protruding position. System 65 (FIG. 6B) includes a pusher-probe 66 enclosed in a cannula 67 maintaining a gap in between cannula lumen 62 and outer boundaries of pusher-probe 66, allowing passage of fluids or/and properly sized medical tools thereacross, when in a retracted position or/and when in a protruding position.

Figure 7A:
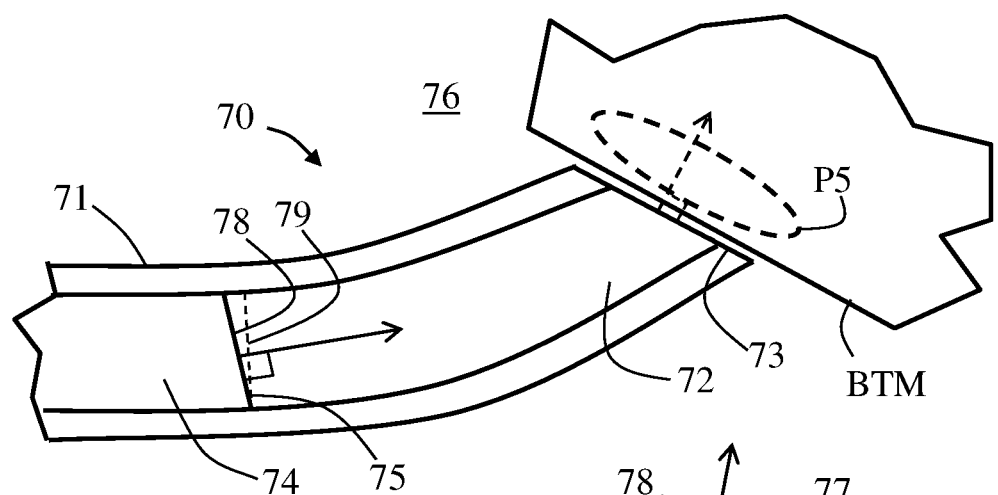
FIGS. 7A-7B schematically illustrate an exemplary system including an exemplary cannular member having a cannular lumen being curved towards its distal end, according to some embodiments of the invention.
Figure 7B:
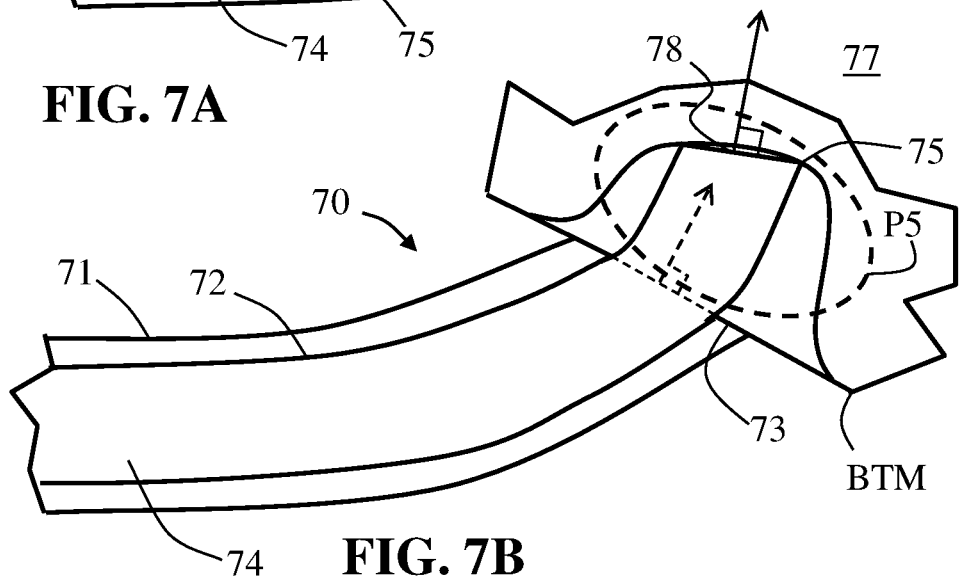

FIGS. 7A-7B schematically illustrate an exemplary system 70 including an exemplary cannular member 71 having a cannular lumen 72 being curved towards a distal end 73 thereof, according to some embodiments of the invention. System 70 may be similar to or different than any of systems 20, 40, 50, 60 and 65, or include other similar or different components to any of them (for instance, yet not limited to, the possibility of a curvature of a cannula lumen portion). In exemplary embodiments, system 70 includes a noncompliant rigid pusher-probe 74 having a pusher-probe distal end 75 and is provided in cannula lumen 72. Pusher-probe 74 is positionable from a retracted position 76 (FIG. 7A), being mostly or fully enclosed within cannula lumen 72, to a protruding position 77 (FIG. 7B), in which pusher-probe distal end 75 protrudes out of cannula distal end 73 to a length up to a maximal protrusion length. Pusher-probe distal end 75 is configured to mechanically manipulate a portion P5 of body tissue mass BTM during repositioning to retracted position 76 or/and to protruding position 77. In some embodiments, mechanical manipulation is achieved by thrusting pusher-probe distal end 75 into mass portion P5 and then releasing contact with it. In some embodiments, pusher-probe distal end 75 includes an angled contacting surface 78, angled relatively to a transversal cross section 79 of any surrounding portion of cannular member 71 adjacent thereto when fully enclosed within cannula lumen 72. In some embodiments, system 70 is designed such and contacting surface 78 is angled such, that contacting surface 78 faces portion P5 of body tissue mass BTM when pusher-probe distal end 75 is in protruding position 77, and inclined to portion P5 when pusher-probe distal end 75 is in retracted position 76. Optionally, cannula distal end 73 is beveled such that it coincides with contacting surface 78.

Figure 8A:
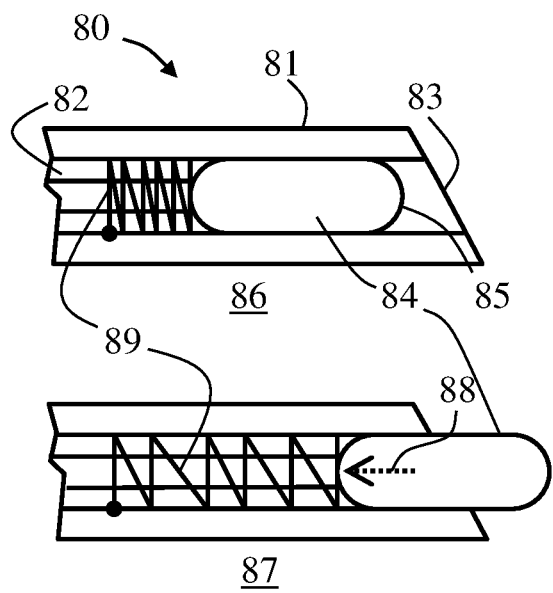
FIGS. 8A-8B schematically illustrate an exemplary system incorporating different exemplary pusher-probe retraction techniques, according to some embodiments of the invention.
Figure 8B:
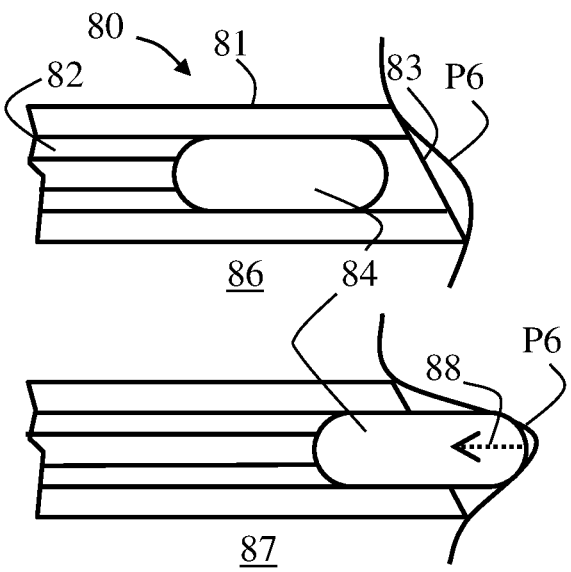

Reference is made to FIGS. 8A-8B which schematically illustrate an exemplary system 80 incorporating different exemplary pusher-probe retraction techniques (in FIG. 8A vs. In FIG. 8B), according to some embodiments of the invention. System 80 may be similar to or different than any of systems 20, 40, 50, 60, 65 and 70, or include other similar or different components to any of them. System 80 includes a cannular member 81 enclosing a cannula lumen 82 opened at a cannula distal end 83. A pusher-probe 84 having a pusher-probe distal end 85 is provided in cannula lumen 82. In exemplary embodiments, pusher-probe 84 is a noncompliant rigid member, particularly configured and suitable to mechanically manipulate (deform) soft tissue it encounters and progresses (advances) through, while exhibiting minimal to no self-deformation. Pusher-probe 84 is positionable from a retracted position 86, being mostly or fully enclosed within cannula lumen 82, to a protruding position 87, in which pusher-probe distal end 85 protrudes out of cannula distal end 83 to a length up to a maximal protrusion length. Pusher-probe distal end 85 is configured to mechanically manipulate a portion P6 of body tissue mass during repositioning to retracted position 86 or/and to protruding position 87. In some embodiments, mechanical manipulation is achieved by thrusting pusher-probe distal end 85 into mass portion P6 and then releasing contact with it.

In some embodiments, an actuation mechanism (for example, actuation mechanism 29 shown in FIGS. 3A-3F) is provided as part of system 80 and is adapted to actuate protrusion of pusher-probe distal end 85 relative to cannula distal end 83, and to allow an immediate follow-up retraction of pusher-probe distal end 85 if it is under a retractive force 88, either if it is originating from an action of embedded retracting means such as a retraction spring 89 (as shown in FIG. 8A), by portion P6 (as shown in FIG. 8B), or in a combination thereof. Therefore, the reaction of the body tissue mass may include retractive force 88 if it is applied by the body tissue mass at a contact area with pusher-probe distal end 85, if, for example, it possesses elastic properties. Optionally, alternatively or additionally, retractive force 88 is applied by a retraction spring 89 extendable or compressible relative to a less stressed condition thereof during pusher-probe distal end 85 repositioning from retracted position 86 to protruding position 87.

FIGS. 9A-9D schematically illustrate an exemplary system 90 having a variable pusher-probe protrusion position, acting upon different exemplary tissue types or/and exemplary anatomic locations, according to some embodiments of the invention. System 90 may be similar to or different than any of systems 20, 40, 50, 60, 65, 70 and 80, or include other similar or different components to any of them. System 90 includes a cannular member 91 enclosing a cannula lumen 92 opened at a cannula distal end 93. A pusher-probe 94 having a pusher-probe distal end 95 is provided in cannula lumen 92. In exemplary embodiments, pusher-probe 94 is a noncompliant rigid member, particularly configured and suitable to push through and mechanically manipulate (deform) soft tissue it encounters and progresses (advances) through, while exhibiting minimal to no self-deformation. Pusher-probe 94 is positionable from a retracted position 96 (shown in FIG. 9A), being mostly or fully enclosed within cannula lumen 92, to a variable protruding position 97 (shown having different protrusion lengths in FIGS. 9B-9D), in which pusher-probe distal end 95 protrudes out of cannula distal end 93 to a length in a range of between a minimal protrusion length $98_{min}$ and a maximal protrusion length $98_{max}$.

In some embodiments, system 90 includes a tissue resistance sensitive member, such as a tactile spring 99, allowing relative backward motion of pusher-probe distal end 95 deriving from retractive force applied by the thrust body tissue mass, superimposed over the forward or backward motion imposed by the system actuation mechanism (for example, actuation mechanism 29 shown in FIGS. 3A-3F). Alternatively, while pusher-probe distal end protrudes out of cannula distal end, proximal end of tactile spring compresses towards pusher-probe distal end once the pusher-probe distal end thrusts into the body tissue mass. Thus, the pusher-probe distal end protrudes to a length in a range of between a minimal protrusion length $98_{min}$ and a maximal protrusion length $98_{max}$.

Therefore, distinct body tissue mass, differentiated by resistivity to mechanical manipulations imposed by pusher-probe 94 (e.g., by pushing or thrusting into such tissue mass), will be associated with different protruding positions and protrusion lengths of pusher-probe distal end 95 relative to a stroke position imposed by the actuation mechanism, in a way that the resulting protruding position 97 is located between minimal protrusion length $98_{min}$ and maximal protrusion length $98_{max}$.

Figure 9A:
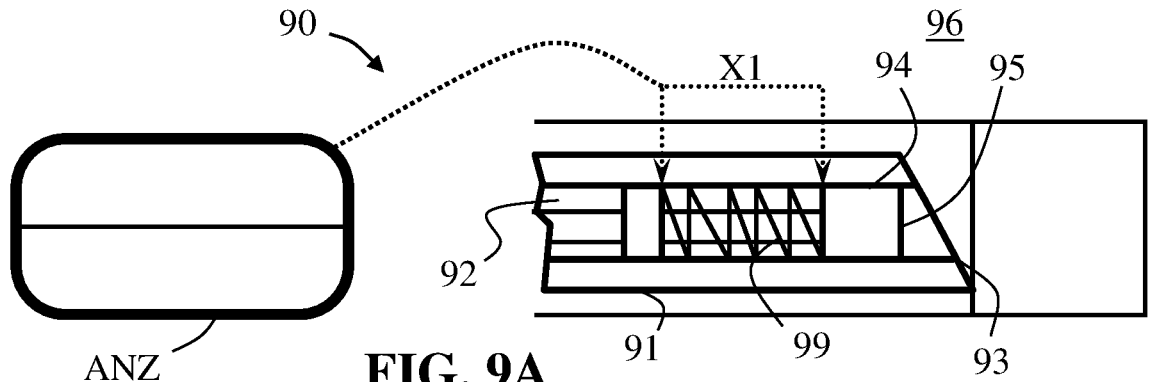
FIGS. 9A-9D schematically illustrate an exemplary system having a variable pusher-probe protrusion position acting upon different exemplary tissue types or/and different exemplary anatomic locations, according to some embodiments of the invention.
Figure 9B:
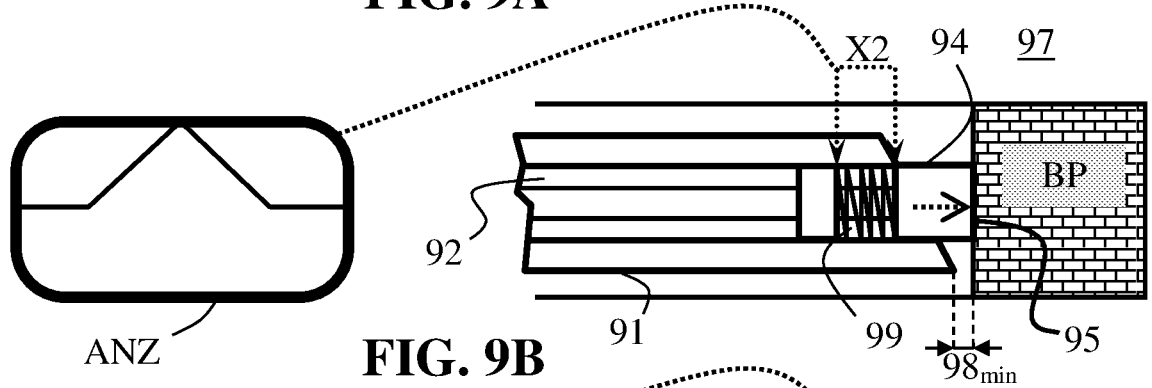

The nominal positioning of system 90 is presented in FIG. 9A, in which cannula distal end 93 is in contact with the body tissue mass, pusher-probe distal end 95 is in a retracted position 96, and tactile spring 99 is in a least-stressed (e.g., maximally extended) resulting in a length X1. FIG. 9B shows a first marginal scenario in which pusher-probe distal end 95 thrusts into a non-yielding or rigid body tissue mass, such as a bony portion BP. As pusher-probe 94 is further pressed towards bony portion BP, the pusher-probe distal end 95 does not advance yet tactile spring 99 compresses until it is fully compressed or/and reaches a compression force equaling the maximal thrusting force applied by the actuation mechanism or/and any other externally applied force to system 90 or to the medical device linked thereto. If the max thrusting force is greater than the maximal force, compressing tactile spring 99 to its full extent, the pusher-probe distal end 95 will still hold in-place but the cannula distal end 93 will shift backwardly (i.e., proximally) until final stroke state shown in FIG. 9B, resulting in a length X2 of tactile spring 99 and in a protruding position 97 corresponding to minimal protrusion length $98_{min}$.

Figure 9C:
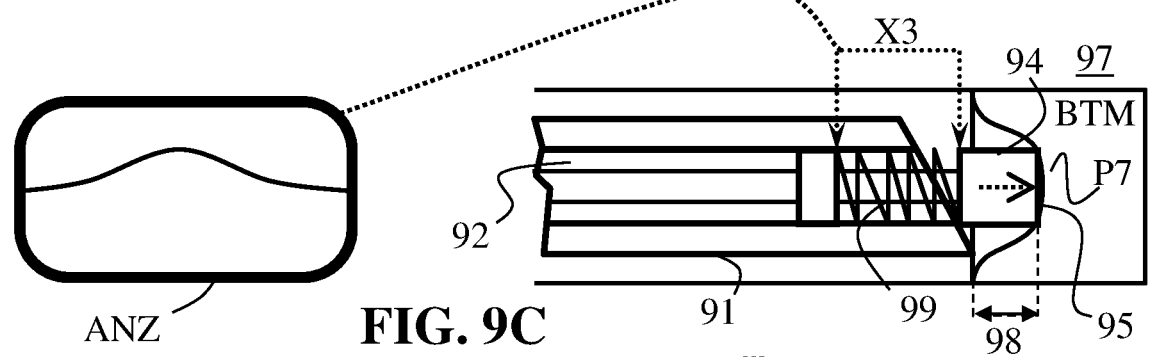
Figure 9D:
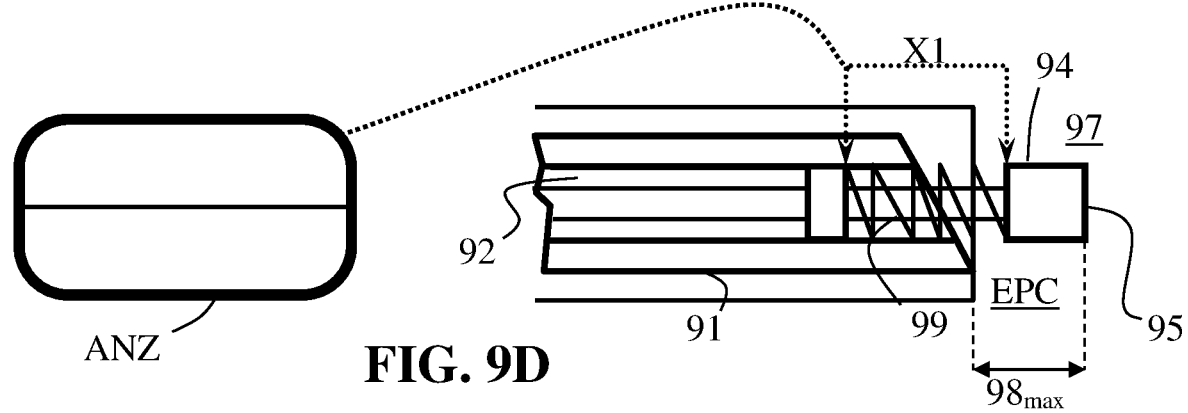

FIG. 9D shows the other marginal scenario in which pusher-probe distal end 95 thrusts into a non-resistive body tissue mass or an intertissual space, such as epidural space EPC. As pusher-probe 94 is pressed towards space EPC, the pusher-probe distal end 95 advances unhindered, encountering little or no resistance. Therefore, tactile spring 99 does not compress and maintains its least-stressed length X1. The final stroke state is shown in FIG. 9D, resulting in a length X1 of tactile spring 99 and in a protruding position 97 corresponding to maximal protrusion length $98_{max}$.

FIG. 9C shows the interaction of system 90 with a yielding/soft or elastic body tissue mass BTM including a soft tissue portion P7. Similarly to previously discussed systems, system 90 is configured such that pusher-probe distal end 95 is configured to mechanically manipulate portion P7 during repositioning to retracted position 96 or/and to protruding position 97. In some embodiments, mechanical manipulation achieved by thrusting pusher-probe distal end 95 into mass portion P7 and then releasing contact with it. Since that portion P7 reacts with an increasing resistive force to pusher-probe distal end 95 thrust and advance thereinto, tactile spring 99 will compress in parallel to portion P7 deformation. The final stroke state is shown in FIG. 9C, resulting in a length X3 of tactile spring 99, optionally, greater than X2 and smaller than X1, and in a protruding position 97 associated with a length 98 greater than minimal protrusion length $98_{min}$ and less than maximal protrusion length $98_{max}$.

A sensor or/and a data-information analyzing device ANZ may be adapted to correlate a mechanical property of the (manipulated) body tissue mass with a sensed effect resulting from reaction of the particular body tissue mass to the mechanical manipulation or merely the incoming thrust, or to the absence of reaction in case of a space or a totally non-resistive matter. Data-information analyzing device ANZ may use information such as measured compression force or/and variable length of the tactile spring 99 during motion or at end-points. This may be combined with information derived from protruding position 97 in any stroke cycle of pusher-probe distal end 95.

In some embodiments, minimal protrusion length $98_{min}$ is at least about 0.2 mm, optionally, at least about 0.5 mm, optionally, at least about 1 mm, or higher, or lower, or an intermediate value. In some embodiments, the maximal protrusion length $98_{max}$ is equal to or less than about 10 mm, optionally, equal to or less than about 5 mm, optionally, equal to or less than about 3 mm, or higher, or lower, or an intermediate value. In some embodiments, system 90 is configured such that distance 98 is in a range of between about 0.2 mm and about 5 mm, optionally, between about 0.5 mm and about 3 mm.

FIGS. 10A-10D schematically illustrate an exemplary system 100 having a fixed pusher-probe protrusion position acting upon different exemplary tissue types or/and different exemplary anatomic locations, according to some embodiments of the invention. System 100 may be similar to or different than any of systems 20, 40, 50, 60, 65, 70 and 80, or include other similar or different components to any of them. System 100 includes a cannular member 101 enclosing a cannula lumen 102 opened at a cannula distal end 103. A pusher-probe 104 having a pusher-probe distal end 105 is provided in cannula lumen 102. In exemplary embodiments, pusher-probe 104 is a noncompliant rigid member, particularly configured and suitable to push through and mechanically manipulate (deform) soft tissue it encounters and progresses (advances) through, while exhibiting minimal to no self-deformation. Pusher-probe 104 is positionable from a retracted position 106 (shown in FIG. 10A), being mostly or fully enclosed within cannula lumen 102, to a fixed protruding position 107 (shown in FIGS. 10B-10D), in which pusher-probe distal end 105 protrudes out cannula distal end 103 to a fixed length despite any encountered resistance or absence of resistance.

Figure 10A:
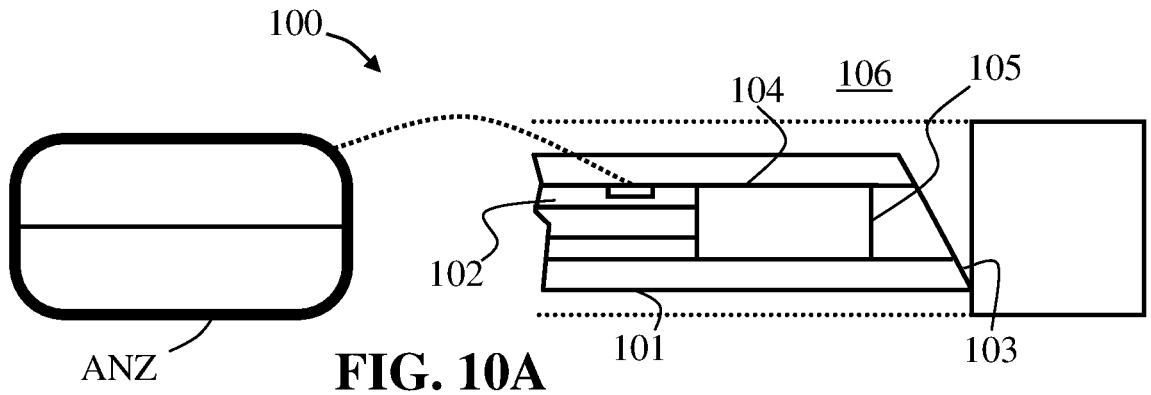
FIGS. 10A-10D schematically illustrate an exemplary system having a fixed pusher-probe protrusion position acting upon different exemplary tissue types or/and different exemplary anatomic locations, according to some embodiments of the invention.
Figure 10B:
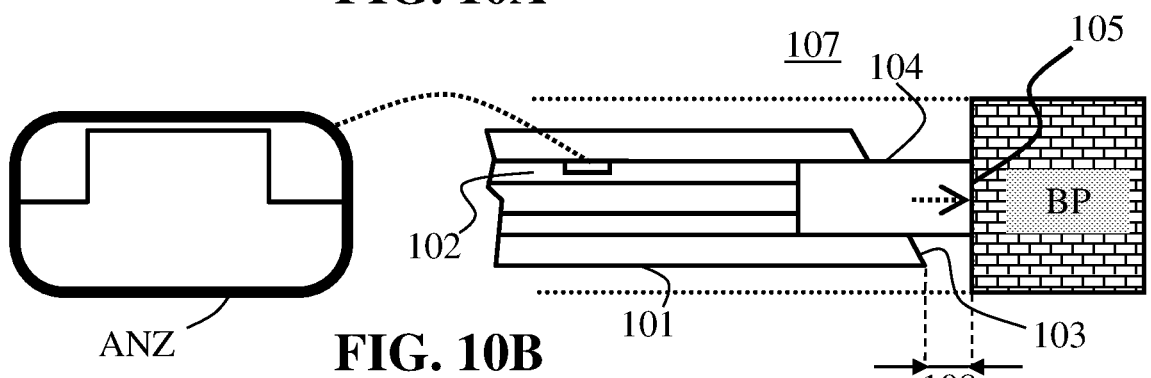

The nominal positioning of system 100 is presented in FIG. 10A, in which cannula distal end 103 is in contact with the body tissue mass and pusher-probe distal end 105 is in a retracted position 106. FIG. 10B shows a first marginal scenario in which pusher-probe distal end 105 thrusts into a non-yielding or rigid body tissue mass, such as a bony portion BP. As pusher-probe 104 is further pressed towards bony portion BP, the pusher-probe distal end 105 does not advance yet the cannula distal end 103 will shift backwardly (i.e., proximally) until the final stroke state shown in FIG. 10B, resulting in protruding position 107 equaling a predetermined or otherwise fixed distance 108 (following retraction of cannular member 101 from bony portion BP and pusher-probe distal end 105. FIG. 10D shows the other marginal scenario in which pusher-probe distal end 105 thrusts into a non resistive body tissue mass or an intertissual space, such as epidural space EPC. As pusher-probe 104 is pressed towards space EPC, the pusher-probe distal end 105 advances unhindered, encountering little or no resistance.

The final stroke state is shown in FIG. 10D, in which protruding position 107 is associated with fixed length 108.

Figure 10C:
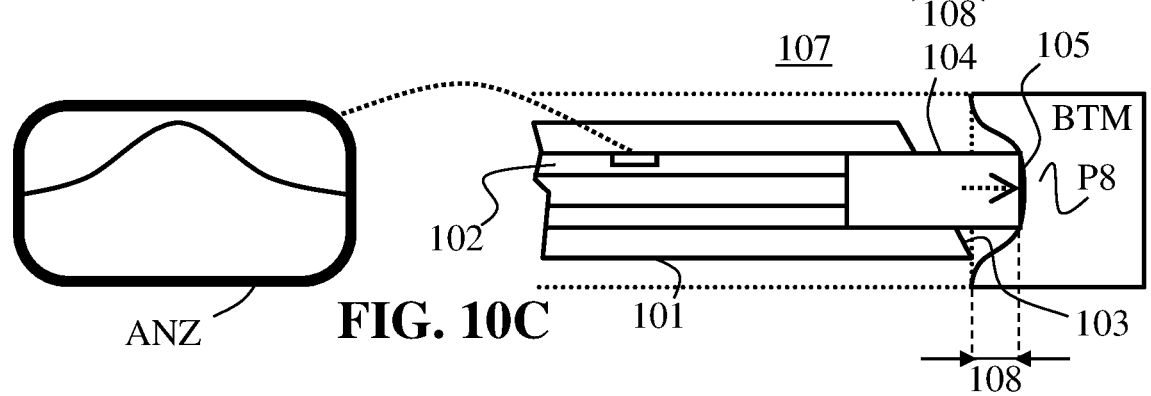
Figure 10D:
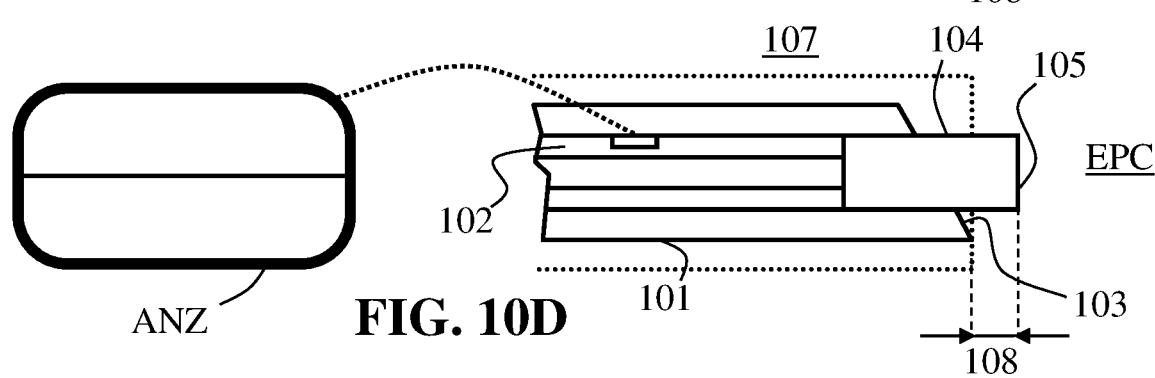

FIG. 10C shows the interaction of system 100 with a yielding/soft or elastic body tissue mass BTM including a soft tissue portion P8. Similarly to previously discussed systems, system 100 is configured such that pusher-probe distal end 105 is configured to mechanically manipulate portion P8 during repositioning to retracted position 106 or/and to protruding position 107. In some embodiments, mechanical manipulation is achieved by thrusting pusher-probe distal end 105 into mass portion P8 and then releasing contact with it. The final stroke state is shown in FIG. 10C, in which protruding position 107 is associated with fixed length 108.

A sensor or/and a data-information analyzing device ANZ may be adapted to correlate a mechanical property of the body tissue mass with a sensed effect resulting from the reaction of the particular body tissue mass to the mechanical manipulation or merely the incoming thrust, or to the absence of reaction in case of a space or a totally non-resistive matter. Data-information analyzing device ANZ may use information such as measured force applied to pusher-probe 104 by the tissue in contact during its reposition cycle(s).

In some embodiments, system 100 is configured such that length 108 is a fixed value, optionally, predetermined or/and programmed, in a range of between about 0.2 mm and about 5 mm, optionally, between about 0.5 mm and about 3 mm.

Figure 11:
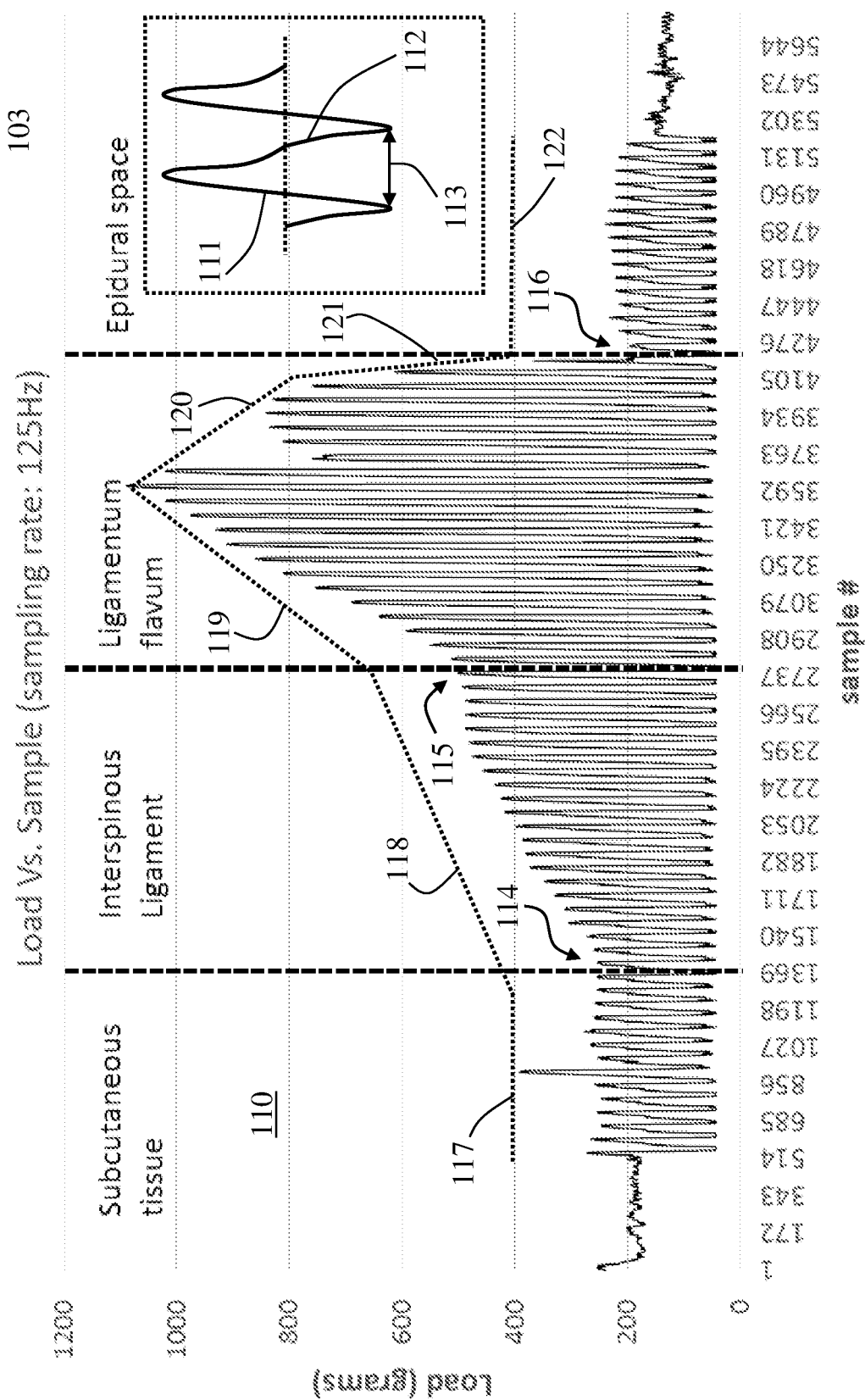
FIG. 11 illustrates an exemplary visual representation of exemplary data sampled using an exemplary system during transtissual progression until reaching epidural space, according to some embodiments of the invention.

FIG. 11 illustrates an exemplary visual representation of exemplary data sampled using an exemplary system during transtissual progression until reaching epidural space, according to some embodiments of the invention. The trial was conducted on Jun. 2, 2014 on a fresh female domestic pig cadaver. The system used a cannular element in the form of a 17GX3.5" Tuohy needle and a pusher-probe in the form of a pusher-probe (outer diameter 1 mm) reciprocally repositioning between a fixed retracted position, 2.5 mm posterior to the needle tip, and a fixed protruding position, of 1 mm distal to the needle tip. The needle was inserted through the skin in an intervertebral space in the lumbar spine by an anesthesiologist. The sensed effect to the pusher-probe, correlated with the resistive force during forward strokes and backwards retractions and measured in grams, was picked up by FC-22 compression load cell 0-10 lbs (Phidgets, Inc), analyzed and plotted as graph 110 in FIG. 11.

As shown in FIG. 11, as the needle progressed transtissually distally from the subcutaneous tissue to the epidural space, the pusher-probe or pusher-probe was repeatedly thrust forward and retracted back within the needle lumen using a motor, and the sensed effect was recorded during both forward stroke motion (shown as rapid steep inclines, similar to illustrated incline 111) and backward retraction motion (shown as rapid slope declines, similar to illustrated decline 112), in each cycle (similar to illustrated cycle 113). The average needle transtissual progression rate was 1 mm per second, stroke cycle duration was about 500 milliseconds and the sampling rate of the picked up sensed effect was 125 Hz.

The immediately recognized, pre-analyzed or processed information is the pusher-probe load in different samplings over different anatomic locations along needle line of progression. As shown, the repetitive load in low resistance anatomic locations such as in subcutaneous tissue and epidural space is significantly lower than in other areas such as in the interspinous ligament and the ligamentum flavum. Following at least one stroke cycle (although more cycles may be needed for accurate assessment) the medical practitioner may immediately recognize penetration into the target location, such as the epidural space. The smaller the stroke cycle duration (the higher the stroke cycle frequency), the tissue sensing resolution improves.

The small stroke cycle duration combined with a high sampling rate can also generate processed and analyzed information, based on the captured data, which can be indicative of currently penetrated and incoming tissue mass, as well as of possible anticipated and immediate indications for penetrating a target or an unwanted tissue, organ or anatomic location. As shown in graph 110, the continuous sampling and the repeated reciprocal pusher-probe reposition cycles indicate an immediate change in slope while passing through different anatomic locations, different tissue masses with variable resistance, or/and different organs, for example, transfer region 114 indicative of passing from subcutaneous tissue to interspinous ligament, transfer region 115 indicative of passing into the ligamentum flavum, and transfer region 116 indicative of passing into the epidural space. The plateau graph segments 117 (indicative of passage through the subcutaneous tissue) and 122 (indicative of passage within epidural space) versus the varying inclined graph segments 118 (indicative of passage through interspinous ligament) and 119 (indicative of passage through most part of the ligamentum flavum) demonstrate an assessment tool for characterization of tissue and anatomic locations along needle path. The transition between inclining graph segment 119 and declining graph segment 120 (which later changes to an immediate drop shown in graph segment 121) may alert in advance that the needle approaches end of travel through the ligamentum flavum and entry to the epidural space.

In some embodiments, the actuation mechanism used in the system includes a motion source, optionally, for generating efficient continuous reciprocal motion. The motion source may include a linear actuator, optionally including a conversion mechanism for converting rotation to linear motion. Optionally, alternatively or additionally, the motion source includes a motor, such as a DC motor or a step motor generating continuous or stepped rotational motion, respectively. The motion source may include gearing, and it may be manually or automatically controllable. In some embodiments, the actuation mechanism includes a coupling linking the motion source to the pusher-probe. In some embodiments, the coupling may be selectively engageable, such as a clutch coupling, and may include a first member (e.g., a drive member) releasably engageable with a second member (e.g., a piston member) which is connected to the pusher-probe.

Reference is now made to FIGS. 12A-12E which illustrate an exemplary system 130 including an exemplary motor and an exemplary clutch coupling, according to some embodiments of the invention. System 130 may be similar to or different than any of systems 20, 40, 50, 60, 65, 70, 80, 90 and 100, or include other similar or different components to any of them. System 130 includes a cannular member 131 enclosing a cannula lumen opened at a cannula distal end 133. A pusher-probe 134 having a pusher-probe distal end 135 is provided in cannula lumen. In exemplary embodiments, pusher-probe 134 is a noncompliant rigid member, particularly configured and suitable to push through and mechanically manipulate (deform) soft tissue it encounters and progresses (advances) through, while exhibiting minimal to no self-deformation. Pusher-probe 134 is positionable from a retracted position, being mostly or fully enclosed within cannula lumen, to a protruding position, in which pusher-probe distal end 135 protrudes out of cannula distal end 133 to a length up to a maximal protrusion length. Pusher-probe distal end 135 is configured to mechanically manipulate a portion of body tissue mass during repositioning to retracted position or/and to protruding position. In some embodiments, mechanical manipulation is achieved by thrusting pusher-probe distal end 135 into mass portion and then releasing contact with it.

In some embodiments, system 130 includes an actuation mechanism 136 that is adapted to actuate protrusion of pusher-probe distal end 135 relative to cannula distal end 133, and to allow an immediate follow-up retraction of pusher-probe distal end 135 under a retractive force originating from an action of retraction spring 137, and optionally, in combination with a resistive force applied by the encountered tissue. Actuation mechanism 136 includes a motion source in the form of a motor 138, optionally, an electric motor, which is configured for providing continuous rotational motion within a chosen duration.

Motor 138 is linked to pusher-probe 134 through a linear clutch coupling 139 which includes a drive member 140 releasably engageable with a piston member 141 connected to pusher-probe 134. Drive member 140 is axially fixed and rotatable in response to a torque applied thereto by motor 138. Piston member 141 is rotationally and axially fixed to pusher-probe 134, and the pusher-probe is rotationally fixed and axially shiftable in cannula lumen between the retracted position and the protruding position. Drive member 140 includes a rotary cam 142 including several peripheral teeth 143 rotationally engageable, sequentially, with a corresponding number of concavities 144 and convexities 145 that are circularly distributed on an opposing surface 146 of piston member 141. When teeth 143 move towards engaging with convexities 145, drive member 140 pushes piston member 141 forward thereby forcing pusher-probe 134 to advance distally up to pusher-probe distal end 135 reaching the protruding position (as shown in FIG. 12D).

Retraction spring 137 which axially supports pusher-probe 134 may be in a form of a compression spring and configured for minimal internal stress when the concavities 144 engage with teeth 143, such that upon disengagement of teeth 143 and convexities 145 the pusher-probe 134 is allowed to retract and is forced by retraction spring 137 to shift proximally up to pusher-probe distal end 135 reaching the retracted position when concavities 144 engage back with teeth 143 (as shown in FIG. 12C). In some embodiments, pusher-probe distal end 135 is configured to spring back from the protruding position thus allowing reengagement of piston member 141 with drive member 140 in response to elastic properties of the body tissue mass. In case of a significant change in resistance or elasticity of the body tissue mass in contact with pusher-probe distal end 135, this will affect the reciprocal elongation-compression motion of retraction spring 137, such that reengagement will not be in same timing if such change had occurred. Optionally, the duration of such reengagement is timed for providing an assessment of the tissue mass elastic properties or/and gradient thereof.

In an alternative option no retractive element, such as retraction spring 137 is used, so that as long as pusher-probe distal end 135 thrusts into motion resistive tissue, the reaction imposed by the tissue will force pusher-probe 134 back until drive member 140 and piston 141 reengage to the compacted form shown in FIG. 12C. If pusher-probe distal end advances to a protruding position in a low resistance tissue or in a space, there will not be any reaction and piston member 141 will remain in a distal position (as shown in FIG. 12D) or continue its travel distally and shift away from drive member 140 (as shown in FIG. 12E). This may be a further indication for reaching an intertissual space such as the epidural space. In such embodiment, the protrusion of pusher-probe 134 beyond cannula distal end may protect the tissue ahead of cannular member 131 from puncture.

A sensor 147 is used to correlate a mechanical property of the (manipulated) body tissue mass with a sensed effect resulting from a reaction of the body tissue mass to the mechanical manipulation. The mechanical property may be force-to-tissue deflection profile, Young modulus, stiffness, failure or yield properties, stress and strain, of the body tissue mass portion (P1). Sensor 147 may be used for sensing sensed effects and for transferring data to a data-information analyzing device 146. Sensor 147 may be or include a force sensor, a motion sensor, a proximity sensor or any other sensor type. In some embodiments, sensor 147 is a force sensor configured to respond to the sensed effect correspondingly to the force component. Data-information analyzing device 146, optionally, includes a data-information processing/programming unit (for example, similar to data-information processing/programming unit 36 shown in FIGS. 3A-3F) programmed to assign a numerical value to the sensed effect, and may also include a memory, wherein the data-information processing/programming unit is programmed to store a database of previous numerical values assigned to previous sensed effects or/and other stored information, and to compare the numerical value of the sensed effect to the database. In some embodiments, system 130 includes a motor control sensor (for example, in FIG. 12B, referenced by 149) configured to respond to sensed effects associated with a change in motor variable such as power consumption derivative, current, back electromotive force, angular velocity, torque, or/and direction of rotation, during repositioning.

In scenarios where a syringe should be connected to the system, it may be advantageous to put the motion source off-axis, as demonstrated in FIGS. 13 and 14. FIGS. 13A-13C schematically illustrate an exemplary system 150 that includes an exemplary motor and an exemplary scotch yoke mechanism, according to some embodiments of the invention. System 150 may be similar to or different than any of systems 20, 40, 50, 60, 65, 70, 80, 90 and 100, or include other similar or different components to any of them. System 150 includes a cannular member 151 enclosing a cannula lumen opened at a cannula distal end 153. A pusher-probe 154 having a pusher-probe distal end 155 is provided in cannula lumen. In exemplary embodiments, pusher-probe 154 is a noncompliant rigid member, particularly configured and suitable to push through and mechanically manipulate (deform) soft tissue it encounters and progresses (advances) through, while exhibiting minimal to no self-deformation. Pusher-probe 154 is positionable from a retracted position, being mostly or fully enclosed within cannula lumen, to a protruding position, in which pusher-probe distal end 155 protrudes out of cannula distal end 153 to a length up to a maximal protrusion length. Pusher-probe distal end 155 is configured to mechanically manipulate a portion of body tissue mass during repositioning to retracted position or/and to protruding position. In some embodiments, mechanical manipulation is achieved by thrusting pusher-probe distal end 155 into mass portion and then releasing contact with it. System 150 is connectable to a syringe 152, such as LOR syringe, fluidly linkable to pusher-probe 154 or to cannula distal end 153.

In some embodiments, system 150 includes an actuation mechanism 156 that is adapted to actuate protrusion of pusher-probe distal end 155 relative to cannula distal end 153 Actuation mechanism 156 includes a motion source in the form of a motor 158, optionally, an electric motor, which is configured for providing continuous rotational motion within a chosen duration. Motor 158 is mechanically linked to pusher-probe 154 using a reciprocating motion mechanism in the form of a scotch yoke mechanism 159, which converts the continuous rotational motion of motor 158 into a reciprocal linear motion that activates pusher-probe distal end 155. Scotch yoke mechanism 159 includes a piston 160 directly coupled to a sliding yoke 161 with a slot 162 that engages a pin 163 on a rotating disc 164 fixed to the rotor of motor 158. As disc 164 rotates with the rotor, pin 163 is forced to slide reciprocally up and down in slot 162 causing yoke 161 to a reciprocal linear motion along a path imposed by piston 160. Piston 160, which is connected to pusher-probe 154, moves together with pusher-probe 154 according to the linear motions of yoke 161. Optionally, alternatively or additionally, actuation mechanism 156 that is adapted to allow an immediate follow-up retraction of pusher-probe distal end 155 under a retractive force originating from an action of a retraction spring or/and by a resistive force applied by the encountered tissue.

Figure 14A:
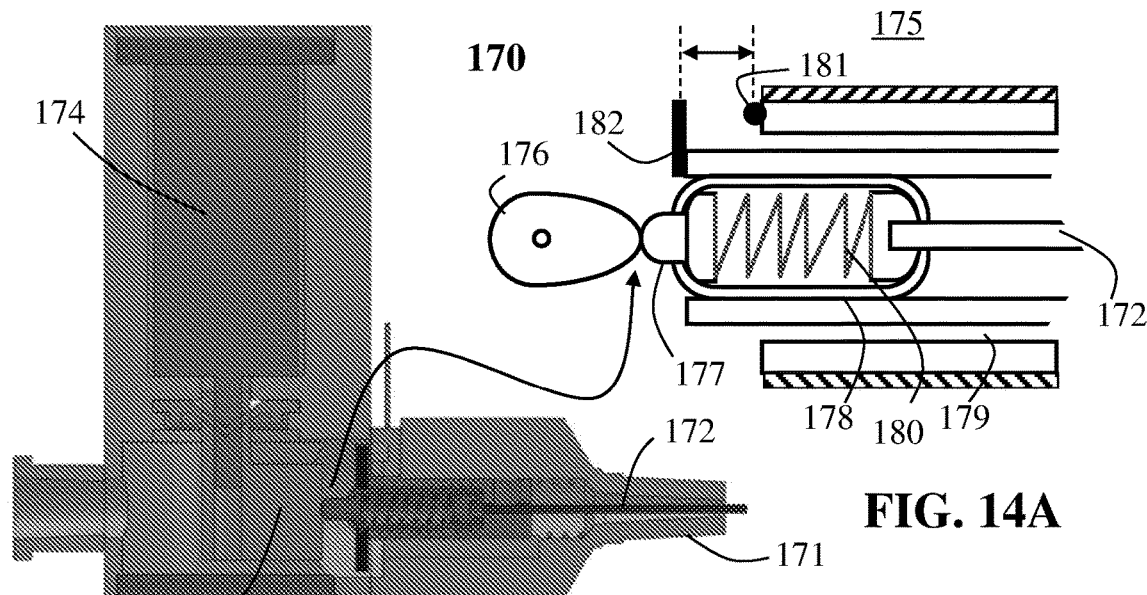
FIGS. 14A-14C schematically illustrate an exemplary system including an exemplary motor and an exemplary camshaft mechanism, according to some embodiments of the invention.
Figure 14B:
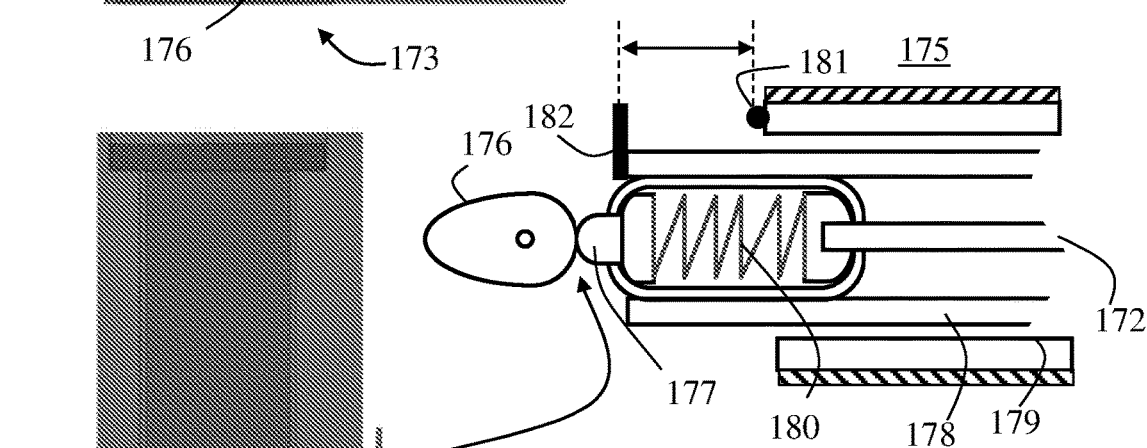
Figure 14C:
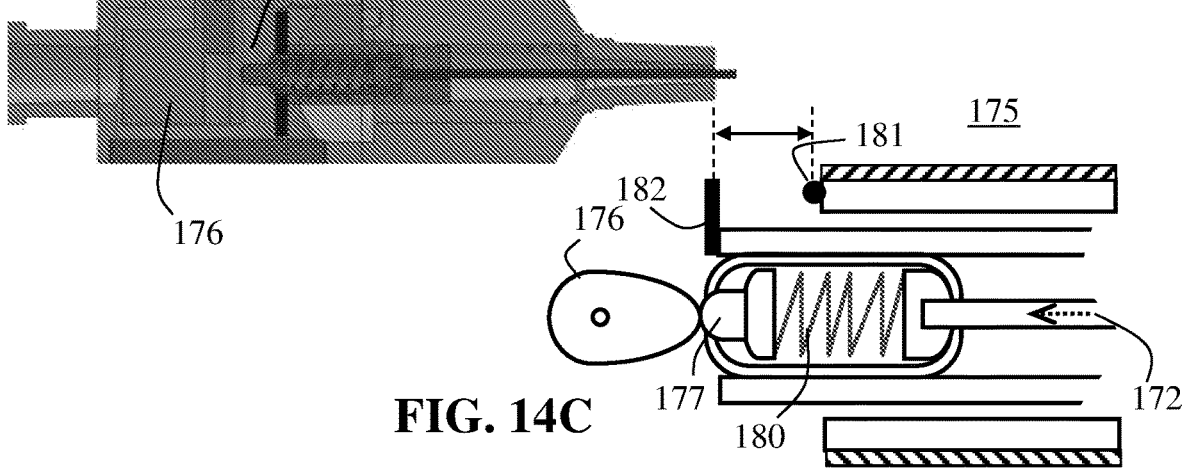

FIGS. 14A-14C schematically illustrate an exemplary system 170 which includes an exemplary motor and an exemplary camshaft mechanism, according to some embodiments of the invention. System 170 may be similar to or different than any of systems 20, 40, 50, 60, 65, 70, 80, 90 and 100, or include other similar or different components to any of them. System 170 includes a cannular member 171 enclosing a cannula lumen opened at a cannula distal end. A pusher-probe 172 (shown in part) having a pusher-probe distal end is provided in the cannula lumen. In exemplary embodiments, the pusher-probe is a noncompliant rigid member, particularly configured and suitable to push through and mechanically manipulate (deform) soft tissue it encounters and progresses (advances) through, while exhibiting minimal to no self-deformation. Pusher-probe 172 is positionable from a retracted position, being mostly or fully enclosed within cannula lumen, to a protruding position, in which pusher-probe distal end protrudes out of cannula distal end to a length up to a maximal protrusion length. Pusher-probe distal end is configured to mechanically manipulate a portion of body tissue mass during repositioning to retracted position or/and to protruding position. In some embodiments, mechanical manipulation is achieved by thrusting pusher-probe distal end into mass portion and then releasing contact with it. System 170 is connectable to a syringe, such as LOR syringe, fluidly linkable to the pusher-probe or to the cannula distal end.

In some embodiments, system 170 includes an actuation mechanism 173 that is adapted to actuate protrusion of pusher-probe distal end relative to cannula distal end, and to allow an immediate follow-up retraction of pusher-probe distal end under a retractive force originating from an action of a retraction spring or/and by a resistive force applied by the encountered tissue. Actuation mechanism 173 includes a motion source in the form of a motor 174, optionally, an electric motor, which is configured for providing continuous rotational motion within a chosen duration. Motor 174 is mechanically linked to pusher-probe 172 using a reciprocating motion mechanism in the form of a camshaft mechanism 175, which converts the continuous rotational motion of motor 174 into a reciprocal linear motion that activates pusher-probe distal end. Camshaft mechanism 175 includes a rotatable cam member 176 including a minimal radius and a maximal radius, both originating from center of rotation. Cam member 176 is fixed to the rotor of motor 174 by its center of rotation. A follower, in a form of a spring loaded ball member 177, is in constant engagement with outer boundaries of cam member 176 and is confined to possible linear travel in housing 178 or/and in slot 179. A measuring spring 180 is located in housing 178 and keeps ball member 177 in a normally extending position away from housing 178 and towards cam member 176. Housing 178 is connected with its distal side (away from cam member 176) to pusher-probe 172, so interaction with tissue of different resistance will affect positioning of housing along slot 179. Therefore, ball member 177 is affected by three variables: the reciprocal rotation movement of cam member 176, the constant extension force applied by measuring spring 180, and the variable force reacted upon the housing from manipulated tissue in contact.

FIG. 14A shows a first scenario in which cam member 176 applies maximal pushing force to ball member 177 as it engages it with its maximal radius, but since the tissue does not react with enough resistance to the thrust by pusher-probe 172, the cam member forces the entire housing 178 (with pusher-probe 172) to a maximal stroke up to maximal protruding position of pusher-probe distal end. FIG. 14B shows a second scenario in which cam member 176 applies minimal pushing force to ball member 177 as it engages it with its minimal radius, so only a mild resistance by the tissue (or/and optionally using a retracting spring) retracts the entire housing 178 (with pusher-probe 172) back to retracted position of pusher-probe distal end. FIG. 14C shows a third scenario in which cam member 176 applies maximal pushing force to ball member 177 (as in the first scenario), but since the tissue react to the thrust by pusher-probe 172 with a resistive force greater than the force applied by measuring spring 180, the ball member is pressed in between cam member 176 and the reacting tissue, and forced to retract into housing 178 while measuring spring 180. This way pusher-probe distal end still protrudes out of cannula distal end, yet to a protrusion length less than the maximal protrusion length.

System 170 includes a proximity sensor 181 which provide values correlated with a distance of marking flag, in a form of a reflective washer 182, thereto. Sensor 181 is fixated to slot 179 while the reflective washer is fixated to the reciprocally sliding housing 178. In the first scenario of FIG. 14A the distance between sensor 181 and washer 182 is smallest and indicating minimal resistance applied to pusher-probe 172 while in protruding position. In the second scenario of FIG. 14B the distance between sensor 181 and washer 182 is greatest and indicating that pusher-probe 172 is in a retracted position. In the third scenario of FIG. 14C the distance between sensor 181 and washer 182 between the maximal and minimal distances indicating a resistance applied to pusher-probe 172 correlating to the measured distance, while pusher-probe 172 is in a protruding position.

Reference is made to FIGS. 15A-15D which schematically illustrate an exemplary manually controllable system 200 including an exemplary extending mechanism, according to some embodiments of the invention. In some embodiments, system 200 is intended for identifying an intertissual space penetrated to by a medical device distal tip, optionally, following transtissual progression thereof through a body tissue mass. In some embodiments, system 200 includes a cannular member 201 enclosing a cannula lumen 202 opened at a cannula distal end 203 having a sharp edge 204. A pusher-probe 205 with a pusher-probe distal end 206 (for example, dull or blunt) is provided in cannula lumen 202. Pusher-probe distal end 206 is positionable from a retracted position 207, being mostly or fully enclosed within cannula lumen 202, to a protruding position 208, in which pusher-probe distal end 206 protrudes out of the cannula distal end 203 to a length 209 between a minimal protrusion length 210 and a maximal protrusion length 211.

System 200 includes an extending mechanism 212 including a cam member 213, a follower 214 shiftable from a first station 215 to a second station 216 on the cam member 213, and a plunger 217 configured for selective traveling in cannula lumen 202 or housing while forcing relative motion between cam member 213 and follower 214, resulting in repositioning of pusher-probe distal end 206 between the retracted position 207 and the protruding position 208, or vice versa.

In some embodiments, when follower 214 rests in first station 215, pusher-probe distal end 206 maintained in retracted position 207 and when follower 214 rests in second station 216, pusher-probe distal end 206 is maintained in a position with minimal protrusion length 210. In some embodiments, first station 215 and second station 216 are separated with an edge 218. Follower 214 includes at least one engaging member 222 (optionally, in the form of a fin) movable between first station 215 and edge 218 or between second station 216 and the edge, for example, in a combined axial and rotational movement. In some embodiments, extending mechanism 212 is arranged such that only upon the pusher-probe distal end 206 reaching maximal protrusion length 211, the engaging member 222 is pressed to pass across edge 218 and to shift from first station 215 to second station 216.

Button 220 is arranged for axial movements along a fixed distance, translating to an axial movement of pusher-probe 205. Button 220 may be a manually operable push button or an automatically operable button, for instance, using an actuation mechanism, such as a motor.

In some embodiments, system 200 includes a tissue resistance sensitive member, such as a tactile spring 221, allowing to decrease the translation of follower 214 and subsequently, pusher-probe distal end 206, in comparison to button 220 axial translation as a result of retractive force applied by the thrust body tissue mass. Therefore, distinct body tissue masses, differentiated by resistivity to mechanical manipulations imposed by pusher-probe 205 (e.g., by thrusting or hammering into them), will derive different protruding positions of pusher-probe distal end 206 relative to button position imposed by the operator, in a way that the resulting protruding position 209 is located between minimal protrusion length 210 and maximal protrusion length 211. In some embodiments, tissue resistance sensitive member 221 can be a bellow, a pressurized elastic bag or any other elastic element that reacts to resistive force.

A retractive member 219, optionally, in the form of a soft compression spring, is configured to immediately lock engaging member 222 in first station 215 or second station 216, after crossing over edge 218.

FIG. 15A shows a first scenario in which pusher-probe distal end 206 is fully retracted and held in place by retracting spring 219. Plunger 217 does not engage with follower 214 and tactile spring 221 is fully relaxed. FIG. 15B shows a second scenario in which cannular member 201 is positioned in front of an elastic tissue portion ETP following transtissual progression thereto. Push button 220 is fully pressed inwardly and forces plunger 217 to engage with the at least one engaging member 222 of follower 214. The elastic tissue portion ETP reacts to the mechanical manipulation (e.g., thrust thereinto by pusher-probe distal end 206) with significant resistance that compresses tactile spring 221 while pusher-probe distal end 206 protrudes until reaching forces equilibrium between the resistive tissue and the force applied by tactile spring 221 while the opposing force applied by retraction spring 219 is negligible. Since that tactile spring 221 was not fully compressed, the engaging members 222 was not able to move across edge 218 and shift from first station 215 to second station 216.

FIG. 15C shows a third scenario in which cannular member 201 has penetrated into a space and pusher-probe 205 encounters little or no resistive force. Therefore, by fully pressing button 220 the tactile spring 221 maintains its maximal length so engaging member 222 can move across edge 218 and shift to rest in second station 216. In some embodiments, plunger 217 is rotationally fixed while follower 214 can be forced to rotate when fully pressed by the plunger until reaching over edge 218. FIG. 15D shows the forth scenario in which the engaging member 219 rests in second station 216, and pusher-probe distal end 206 is partially retracted to a final resting position within the target anatomic location. Button's 220 new position signify the correct placement of pusher-probe. Moreover, pusher-probe distal end 206 protruding from cannula distal end 203 can protect the surrounding tissue from further progression by leaning over sharp edge 204.

According to an aspect of the invention, provided are techniques (exemplary system and method embodiments) for delivering a medicinal substance (such as a drug, for example, an anesthetic agent) to a target location (for example, an epidural space) in a subject's body.

Reference is made to FIGS. 16A-16H which illustrate exemplary embodiments of an exemplary system 300 for delivering a medicinal substance to a target anatomic location in a subject's body, optionally, by first identifying a target anatomic location penetrated to by a medical device distal tip following transtissual progression thereof through a body tissue mass.

Figure 16A:
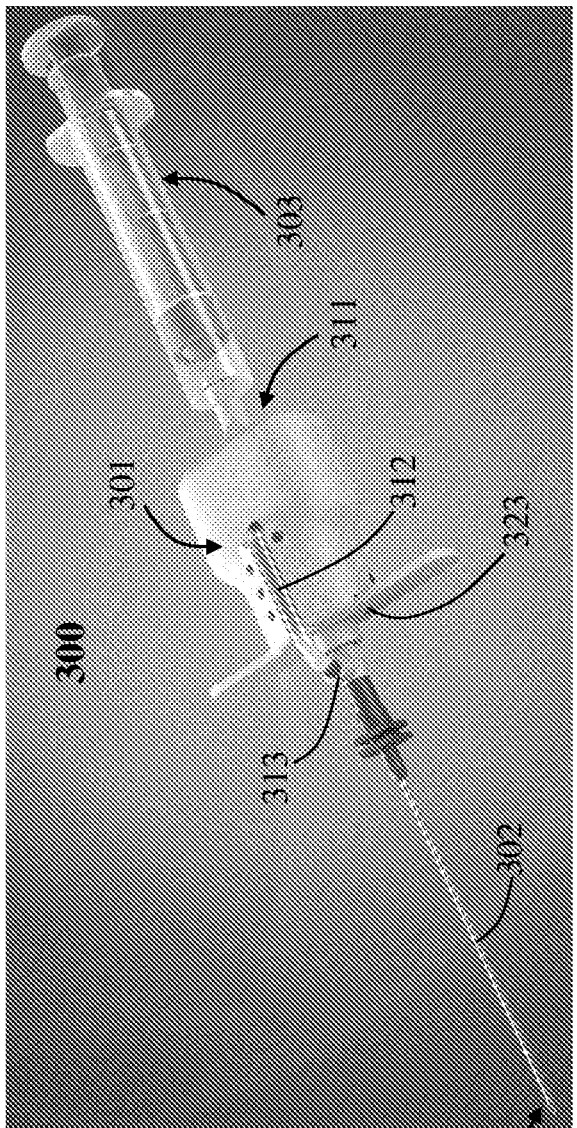
Figure 16I:
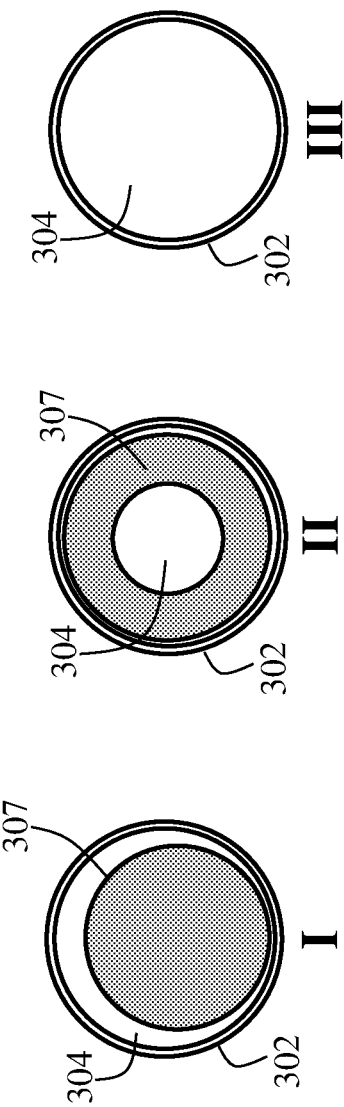
FIG. 16I schematically illustrates different options for delivering a medicinal substance to a target location via a cannula lumen of an exemplary system, according to some embodiments of the invention.
Figure 16B:
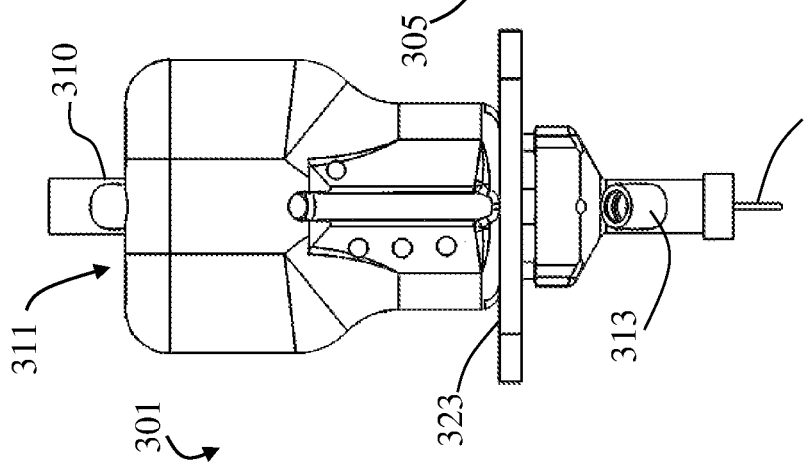

As shown in FIGS. 16A-16B, system 300 includes a handheld housing 301 that is connectable with a cannular member 302 in a proximal side thereof, and with a syringe 303 in another side thereof. Cannular member 302 encloses a cannula lumen 304 opened at a cannula distal end 305 having a sharp edge 306 (shown in FIG. 16C, for example). A pusher probe 307 having a dull or blunt pusher-probe distal end 308 is provided in cannula lumen 304 and is slidable therein (shown in FIG. 16C, for example). Housing 301 incorporates an actuation mechanism 309 that is adapted to actuate repeated protrusions of pusher-probe distal end 308 relative to cannula distal end 305 (shown in FIG. 16D, for example), as described in more detail below.

System 300 is configured for advancing towards the target location in the subject's body by pushing forward cannular member 302. Sharp edge 306 can be used for transtissual penetration through soft tissue along an advancement path at intervals when pusher-probe distal end 308 is retracted proximally thereto (as shown in FIG. 16C-II), while, optionally, advancement is interrupted with resistance thereto by incoming body tissue mass at other intervals when pusher-probe distal end 308 is protruded distally to sharp edge 306 (as shown in FIG. 16C-I). An operator may cease advancing the system upon recognizing that cannula distal end 305 is at the chosen target location, and may then deliver a medicinal substance to the target location via cannula lumen 304. In some embodiments, system 300 is configured also, or even particularly, for targeting an epidural space and for delivering a drug thereto, which may include an anesthetic agent.

Syringe 303 may be used with air or with an inert substance (such as saline solution) for avoiding reaction with body tissues, and later be replaced with a syringe containing a medicinal substance. Syringe 303 may be designated and use as a loss-of-resistance (LOR) syringe. A coupling 310 is provided at proximal end 311 of housing 301 for coupling with syringe 303, optionally particularly to an LOR type syringe. Coupling 310 may be a slip-on connector type (e.g., luer-slip connector), or a locking connector (e.g., a luer-lock connector). Coupling 310 is in fluid communication with cannula lumen 304, and may be interconnected with a fluid channel 312 provided in-between, via a cannula fluid port 313, which may be in a form of a luer-slip connector or a locking connector, for example. Fluid channel 312 may include an at least partially transparent portion for allowing presence of fluid thereinside, such as blood or optionally other colored fluid. In an alternative exemplary embodiment, a port opened to cannula lumen 304, such as cannula fluid port 313, may be configured for direct coupling with a syringe. In some embodiments, fluid can be passed via cannula lumen 304 only in the absence of pusher-probe 307 thereinside, while in other embodiments, pusher-probe 307 or a different dedicated member can be configured such that fluid travels thereacross or/and therethrough when if in retracted position or/and in protruding position relative to cannula distal end 305.

Referring back to FIG. 16C, and as mentioned above, pusher-probe distal end 308 is positionable from a retracted position (as shown in scenario II), being enclosed within cannula lumen 304, to a protruding position (as shown in scenario I), in which pusher-probe distal end 308 protrudes out of cannula distal end 305 to a length L in a range of between a minimal protrusion length and a maximal protrusion length. Maximal protrusion length is optionally equal to or less than about 10 mm, or optionally about 5 mm, or optionally about 3 mm, or optionally 2.5 mm.

In some embodiments, pusher-probe 307 is noncompliant rigid relative to body tissue mass in contact at least if it is within cannular member 302, this way the substantially entire resistance of the body tissue mass to manipulation (i.e., the resisting force applied to pusher-probe 307 in reaction to protrusion or/and thrust towards the body tissue mass) can be transferred directly and immediately with minimal energy loss along length of pusher-probe 307 (e.g., if, alternatively, elastic or plastic behavior would occur in a conforming/flexible member placed within cannular member 302). In some embodiments, pusher-probe distal end 308 is configured to mechanically manipulate a portion of the body tissue mass, via thrusting into and then releasing contact with it, during repositioning of pusher-probe distal end 308 to the retracted position or/and to the protruding position. Pusher-probe distal end 308 is optionally sized or/and shaped so as to prevent penetration thereof into the body tissue mass during repositioning.

In some embodiments, distance L of pusher-probe distal end 308 to cannula distal end 305 in the protruding position is determined according to said mechanical property of the body tissue mass, and wherein distance L is in a range of between about 0.2 mm and about 5 mm. Optionally, the mechanical manipulation is non-traumatic to the body tissue mass and includes at least one of laterally stretching, distally compressing, distally curving, distally bending, distally pushing, and rotationally twisting the body tissue mass, with pusher-probe distal end 308, or/and at least partially immersing in the body tissue mass with pusher-probe distal end 308.

Actuation mechanism 309 is adapted to actuate repeated protrusions of pusher-probe distal end 308 relative to cannula distal end 305 which include continuous cycles of a protrusion of pusher-probe distal end 308 relative to cannula distal end 305 followed by an immediate retraction of pusher-probe distal end 308 if under a refractive force. Such retractive force can be applied, for example, by a retraction spring 321 (shown in FIG. 16G) which changeable in length during repositioning of pusher-probe distal end 308 from retracted position to protruding position.

Optionally, actuation mechanism 309 is adapted for automatic reciprocal repositioning of pusher-probe distal end 308 between the retracted position and the protruding position during a defined actuation period.

Figures 16G, 16H:
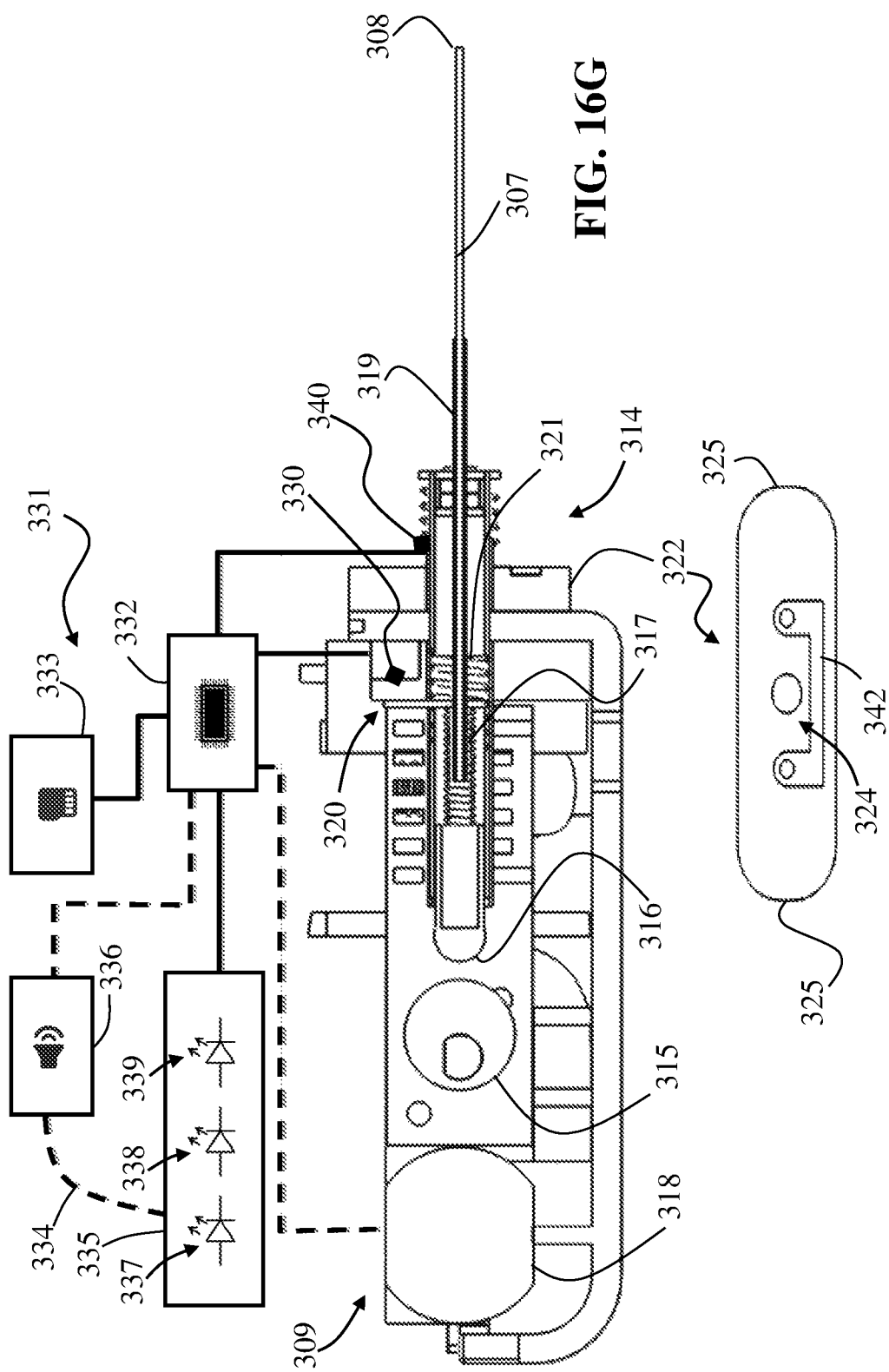

As shown in FIG. 16E and FIG. 16G, actuation mechanism 309 includes an extending mechanism 314 comprising a cam member 315, and a follower 316 shiftable from a first station S1 to a second station S2 on cam member 315. Follower 316 is configured for applying forces to pusher-probe 307 thereby effecting change in position of pusher-probe distal end 308 relative to cannula distal end 305, in accordance with a continuously variable distance X of follower 316 from rotation center 344 of cam member 315 or/and with resistance to pusher-probe 307 by incoming body tissue mass. Extending mechanism 314 may be configured such that pusher-probe distal end 308 remains in retracted position, when follower 316 rests in first station S1. Similarly, extending mechanism 314 may be configured such that pusher-probe distal end 308 protrudes out through cannula distal end 305 when follower 316 rests in second station S2.

In some embodiments, extending mechanism 314 includes a measuring spring 317 provided between follower 316 and pusher-probe 307, and configured to change in length between a first, optionally compressed or relaxed, length and a second compressed length, optionally related to a difference between an activating force applied thereto by follower 316 and an opposing resistive force applied thereto by pusher-probe 307. Optionally, the resistive force equals the resistance to pusher-probe 307 applied by an incoming body tissue mass.

FIG. 16E, in scenario I, shows cam member 315 and follower 316 positioned in first station S1, in which measuring spring 317 is at its maximally allowed or prescribed length, optionally relaxed (i.e., non-stressed), and pushing-probe distal end 308 is provided entirely proximally to sharp edge 306 of cannular member 302 (as shown in FIG. 16C, scenario II, for example). In both scenarios II and III of FIG. 16E, cam member 315 and follower 316 in second station S2, yet in scenario III measuring spring 317 is further compressed, with respect to its length in scenario II, since resistance to pusher-probe distal end 308 applied by an incoming body tissue mass is greater in magnitude. Pusher-probe 307 may be connected to measuring spring 317 via another structural member, such as a tube 319 that is connected in one end thereof to a proximal end of pusher-probe 307, and with another end thereof to measuring spring 317, and optionally also to a marking flag 320 which serves, in this exemplary embodiment, as proximity indicator in sensing/measuring activity as will we further detailed below.

In exemplary embodiments, measuring spring 317 has a spring constant of about 1.4 N/mm, so system 300 can be configured for measuring resistances of incoming body tissue mass within a range of between about 0 N and about 4 N, corresponding to measuring spring compression between about 0 mm and about 3 mm, using pusher-probe 307 and extending mechanism 314 configured for a maximal protrusion of about 2.5 mm between pusher-probe distal end 308 and cannula distal end 305 or sharp edge 306 (if no resistance is applied thereto), and full retraction of about 0.5 mm proximally to sharp edge 306.

Table 1 summarizes possible exemplary indications for tissue types or/and anatomic locations ("Anatomic Indication") determined according to situation of extending mechanism 314 ("Pusher-Probe Protrusion" and "Measuring Spring Compression"):

TABLE 1

Exemplary Anatomic Indications determined according to exemplary Pusher-Probe Protrusion lengths and exemplary Measuring Spring Compression lengths.

| Pusher-Probe Protrusion [min] | Measuring Spring Compression [mm] | Anatomic Indication |
|---|---|---|
| 1.7-2 | 0.5-0.8 | Supraspinous ligament |
| 1.7-1.5 | 0.8-1.0 | Interspinous ligament |
| 1.5-0.5 | 1.0-2.0 | Ligamentum Flavum |
| 2.3 | 0.2 | Epidural Space |

Actuation mechanism 309 further includes a motion source 318 (e.g., a DC motor) for providing continuous reciprocal repositioning to pusher-probe distal end 308 relative to cannular member distal end 305. Such reciprocal repositioning may include a plurality of stroke cycles, each comprising a single forward stroke from retracted position to protruding position, and a single backward retraction from the protruding position to the retracted position. Optionally, each stroke cycle has a frequency in a range of between about 1 Hz and about 20 Hz. In some embodiments, such reciprocal repositioning facilitates unhindered transtissual progression of the medical device through soft tissue with a progression velocity equal to or less than about 5 mm per second.

In some embodiments, system 300 includes a trigger mechanism 322 which may be intended to control parameters such as extent and timing of sensing, measuring or/and signaling in parallel to use of system 300, for example in order to diminish probability of false-positive results. As an example, a potential false-positive measurement may be caused, in absence of trigger mechanism 322, for example, in case that system 300 is shifted backwards (proximally) so pusher-probe 307 is withdrawn to a space or a gap possibly created by cannular member distal end 306 previously passing therethrough with its sharp edge 306. Trigger mechanism 322, shown for example in FIG. 16F, includes a winged hub member 323 that includes a hub body 324 coupled with at least one wing-like flange 325 sized and shaped for effective finger pressing thereto. Winged hub member 323, as shown in this exemplary embodiments, includes two wing-like flanges 325 connected at opposing locations around hub body 324, so as to allow pressing thereof in-parallel by two fingers from two sides around cannular member 302. Hub body 324 is slidably connected via a structural portion 327 of system 300 proximally to cannular member 302 and is slidable from a first hub position HP1 (shown in FIG. 16F, scenario I) to a second hub position HP2 (shown in FIG. 16F, scenario II) distal to first hub position HP1.

In some embodiments, trigger mechanism 322 includes a hub retracting mechanism 326, optionally including a hub spring, configured for resisting motion of winged hub member 323 away from first hub position HP1. Hub retracting mechanism 326 is optionally configured for such motion resisting only if pressed with a force greater than a predetermined threshold force. Optionally, alternatively or additionally, hub retracting mechanism 326 is configured for retracting winged hub member 323 relative to structural portion 327 after reaching second hub position HP2 or/and if pressed with a force less than the predetermined threshold force.

As previously described, an activation cycle of pusher-probe 307 includes a single protrusion maneuver followed by a single retraction of pusher probe distal end 308, as determined by a single rotation cycle of cam member 315 around its rotation center 344 (as shown in FIG. 16E, for example). In some embodiments, system 300 (e.g., via extending mechanism 314 configuration) is configured such that the activation cycle of pusher-probe 307 includes an effective measuring period, particularly relevant for measuring tissue characteristics, where the effective measuring period is equal to, or shorter in duration than, the entire cycle duration.

Referring back to FIG. 16G, a sensor 330, in a form of proximity sensor, is provided in system 300, which is configured for measuring the distance to marking flag 320 which is connected to measuring spring 317. Continuous measurements (e.g., periodical sampling of distance related data) by sensor 330 can be used to calculate/determine extent of compression of measuring spring 317, optionally and particularly when follower 316 is in S2 position, which can be adapted for correlating a mechanical property of the body tissue mass, in direct contact with pusher-probe distal end 308, with a sensed affect resulting from the body tissue mass reacting to mechanical manipulation by pusher-probe distal end 308. Optionally, sensed effects are sampled with a sampling rate in a range of between about 50 Hz and about 1,000 Hz.

In some embodiments, this effective measuring period is determined by at least one of: (1) any continuous period in which measuring spring 317 is stressed (e.g., compressed), (2) any continuous period in which marking flag 320 is distanced away from sensor 330 by no more than a predetermined value (for example, distances equal to or less than about 4 mm), and (3) relative positioning of cam member 315 (between and including stations S1 and S2). In some embodiments, the sensed information can be also used for determining protrusion, or/and calculating/determining protrusion length, of pusher-probe distal end 308 to cannula distal end 305, which may be useful, for example, for locking pusher-probe 307 in a protrusion state, or in a retraction state. A data-information analyzing device 331 is also provided and includes an integrated circuit or/and a data-information processing/programming unit, in a form of microprocessor 332, programmed to assign a numerical value to the sensed affect. Data-information analyzing device 331 also includes a memory 333 linked with microprocessor 332. Data-information processing/programming unit (microprocessor 332) is programmed to store in memory 333 a database of previous numerical values assigned to previous sensed affects or/and other stored information, and to compare the numerical value of the (new/incoming) sensed affect to the previous numerical values of the database.

In some embodiments, a signifying device 334 is provided in system 300 and linked with data-information analyzing device 331, optionally directly with microprocessor 332. Signifying device 334 optionally includes at least one of a visual signaling unit 335 and an audio signaling unit 336. Visual signaling unit optionally includes at least three light-emitting diodes (LEDs). In exemplary embodiments, each LED is optionally functional (e.g., activated by microprocessor 332), unitarily or/and in combination with other LEDs, within a first range of numerical values assigned to a first group of sensed affects that represent characteristics of (e.g., resistance applicable by) a body tissue mass. In an exemplary embodiment, a first LED 337 is functional upon measuring resistance relating to protrusion of pusher-probe distal end 308, with certain mechanical characteristics (e.g., thrust force, momentum, cycle rate, velocity or/and other), against subcutaneous tissue. Optionally and additionally, a second LED 338 is functional upon measuring resistance relating to protrusion of pusher-probe distal end 308, with certain mechanical characteristics (e.g., thrust force, momentum, cycle rate, velocity or/and other), against interspinous ligament. Optionally and additionally, a third LED 339 is functional upon measuring resistance relating to protrusion of pusher-probe distal end 308, with certain mechanical characteristics (e.g., thrust force, momentum, cycle rate, velocity or/and other), against ligamentum flavum. Optionally and additionally, all three LEDs 337, 338 and 339 are functional (e.g., blinking together) upon measuring resistance relating to protrusion of pusher-probe distal end 308, with certain mechanical characteristics (e.g., thrust force, momentum, cycle rate, velocity or/and other), against tissues (e.g., fatty tissue) present in the epidural space. Audio signaling unit 336, optionally comprising a buzzer, may be applied to produce audio signals upon change in activity of any of the LEDs.

FIG. 16H shows an exemplary design for winged hub member 322 with an embedded electrical conductive liner 342 that closes a circuit with a hub locator 340, provided adjacent or on structural portion 327, only upon positioning of winged hub member 322 in the second hub position HP2. In some embodiments, microprocessor 332 is linked with hub locator 340 and is operable in a predetermined action only when conductive liner 342 closes a circuit with hub locator 340. Microprocessor 332 interrogates or/and passively receives signals or other information from both hub locator 340 and sensor 330 in order to determine if to allow activation of motion source 318 and optionally to what extent (e.g., torque or velocity) or/and to determine if to activate or change status of signifying device 334 or any component thereof, for example in order to avoid false-positive readings. In some embodiments, microprocessor 332 is programmed to allow or command first activation of motion source 318 or/and sensor 330 only if hub locator 340 first identifies a continuous positioning of winged hub member 322 in the second hub position HP2 for at least 1-2 seconds, thereby representing intentional activation of system 300 by the system operator. Optionally, additionally or alternatively, system 300 can be configured for allowing activation of motion source 318 or/and changing status of signifying device 334, or any component thereof, only if hub locator 340 identifies position of winged hub member 332 in second hub position HP2 for at least about 0.3 second to about 1 second, thereby representing intentional progression of cannular member 302 by the system operator.

A battery 341 (shown in FIG. 16F, for example) is provided for powering at least one of data-information analyzing device 331 and components thereof, motion source 318, and signifying device 334 and components thereof.

FIG. 16I schematically illustrates different options for delivering a medicinal substance to a target location via cannula lumen 304 of the exemplary system 300, according to some embodiments of the invention. Scenario I of FIG. 16I shows a first example where pusher-probe 307 has total cross section having a smaller diameter than of inner diameter of cannular member 302, therefore fluid can travel thereacross, for example when pusher-probe 307 is in retracted position or/and when in protruding position. For example, maximal or average outer diameter of pusher-probe 307 is equal to or less than 2 mm, or equal to or less than 1 mm, or equal to or less than 0.7 mm, optionally about 0.54 mm, or optionally about 0.6 mm, while, optionally, maximal or average diameter of cannula lumen 304 is greater than pusher-probe diameter by at least about 0.1 mm, or by at least about 0.2 mm, or by at least about 0.5 mm. In some embodiments, a minimal free area for fluid passage is at least about 0.2 mm$^2$, or optionally at least about 0.5 mm$^2$, or optionally at least about 0.8 mm$^2$.

Scenario II of FIG. 16I shows a second example where pusher-probe 307 has an inner lumen sharing a volume with cannula lumen 304, therefore fluid can travel therethrough, for example when pusher-probe 307 is in retracted position or/and when in protruding position. Scenario III of FIG. 16I shows a third example where pusher-probe 307 is absent (e.g., after removal from cannular member 302), therefore fluid can through cannula lumen 304.

FIG. 17 is a flow diagram of an exemplary embodiment (indicated as, and referred to by, reference number 400), including the indicated exemplary steps (procedures) and associated equipment thereof, of a method for delivering a medicinal substance to a target anatomic location in a subject's body. In FIG. 17, exemplary embodiment 400 of the method includes exemplary steps (procedures) represented by separate blocks (frames) which are assigned reference numbers, for example, 404, 408, 412, etc. . . . In a non-limiting manner, and in some embodiments, such as exemplary embodiment 400, the medicinal substance delivery method includes the following exemplary steps (procedures) and associated equipment.

In 404, there is providing a system including: a cannular member enclosing a cannula lumen opened at a cannula distal end having a sharp edge; a pusher-probe having a dull or blunt pusher-probe distal end; and an actuation mechanism adapted to actuate repeated protrusions (advancements) of the pusher-probe distal end relative to the cannula distal end.

In 408, there is applying the actuating mechanism to effect continuous cycles of a protrusion (advancement) of the pusher-probe distal end relative to the cannula distal end, followed by an immediate retraction of the pusher-probe distal end when the pusher-probe is under a retractive force.

In 412, there is advancing towards the target anatomic location in the subject's body by pushing forward the cannular member, via transtissually penetrating soft tissue with the cannula distal end sharp edge at intervals when the pusher-probe distal end is retracted proximally to the cannula distal end sharp edge, wherein the advancing is interrupted with resistance thereto by incoming body tissue mass at other intervals when the pusher-probe distal end is protruded distally to the cannula distal end sharp edge.

In 416, there is recognizing that the cannula distal end is at the target anatomic location for ceasing the advancing.

In 420, there is delivering, via the cannula lumen, the medicinal substance to the target anatomic location in the subject's body.

FIGS. 18A-18G illustrate exemplary embodiments of implementing an exemplary method for delivering a medicinal substance to a target anatomic location in a subject's body, using the exemplary system 300. As shown in these exemplary embodiments, the target anatomic location is an epidural space, and the medicinal substance is a drug, where the drug may be an anesthetic agent, or may include an anesthetic agent.

Figure 18A:
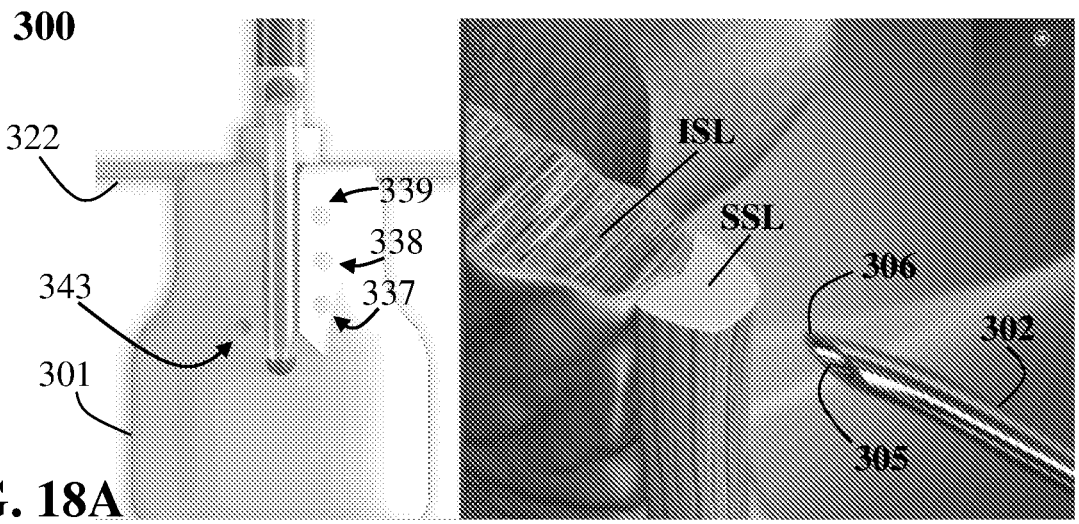

As shown in FIG. 18A, system 300 is provided and then powered on (a power-LED 343 is shown as activated), nevertheless protrusion-retraction cycles of pusher-probe distal end 308 are not operative since that winged hub member 322 is not pressed or not in second hub position HP2 for at least 2 seconds. Upon pressing towards subject's body or/and penetration into subcutaneous tissue SCT with sharp edge 306 of cannular member 302, winged hub member 322 is pressed continuously while located in second hub position HP2, therefore actuating mechanism 309 is applied to effect continuous cycles of a protrusion of pusher-probe distal end 308 relative to cannula distal end 305, followed by an immediate retraction of pusher-probe distal end 308 under a retractive force applied by retraction spring 321. In some embodiments, system 300 is configured such that actuating mechanism 309 is halted immediately upon repositioning of winged hub member 322 away from second hub position HP2, or after such repositioning for at least a predetermined minimal time (for example, at least 0.3 second).

System 300 can then be advanced towards the target location in the subject's body by pushing forward cannular member, including transtissually penetrating soft tissue with sharp edge 306 at intervals when pusher-probe distal end 308 is retracted proximally to sharp edge 306. Advancing can be interrupted with resistance to pusher-probe distal end 308 by incoming body tissue mass at other intervals when it is protruded distally to sharp edge 306. In some embodiments, pusher-probe distal end 308 remains noncompliant and rigid relative to the body tissue mass, thereby projecting in line with cannula distal end 305 when protruded distally to sharp edge 306. During the advancing, data-information analyzing device 331 may perform at least one of the following data-information analytical operations or actions,

- Measuring a sensed effect resulting from resistance to protrusion of pusher-probe distal end 308 during system 300 advancing.
- Correlating the sensed effect to a previous record indicative of a known bodily region or/and body tissue mass.
- Comparing the sensed effect with an immediately previous recorded sensed effect
- Signaling upon at least one of the following measuring steps (procedures):
  - Measuring a sensed effect resulting from body tissue mass resistance in magnitude taken from a range or ranges of predetermined values.
  - Measuring a sensed effect being at least 20-50% different than an immediately previous recorded sensed effect.
  - Measuring a change between recorded sensed effects being indicative of a known bodily region or/and body tissue mass or of penetration from a first bodily region comprising mostly of first tissue type to a second bodily region comprising mostly from a second tissue type.
- Excluding or/and pausing measurement when measuring spring 317 is unstressed or/and when marking flag 320 is distanced away from sensor 330 by more than a predetermined maximal value (e.g., 4 mm or more).

In some embodiments, at least one of the applying and the advancing is ceased immediately upon recognizing that the cannula distal end is at the target anatomic location, for example, in the epidural space.

In some embodiments, at least one of the applying, the advancing and the recognizing is facilitated only if winged hub member 322 is at, or distal to, second hub position HP2.

Figure 18B:
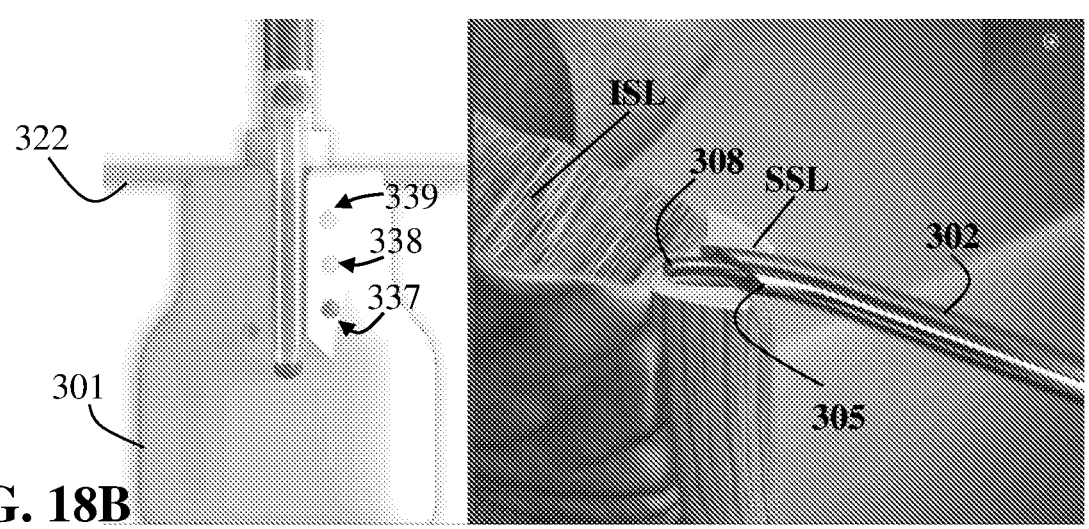

FIG. 18B shows a second instance where cannula distal end 305 is located within supraspinous ligament SSL following penetration thereto. First one or several cycles of protrusions in supraspinous ligament SSL are used for measuring resistance applied by this body tissue mass against distal progression of pusher-probe distal end 308, until penetrating to a different anatomical location with body tissue mass characterized in different resistance. During this period, first LED 337 is active as shown.

Figure 18C:
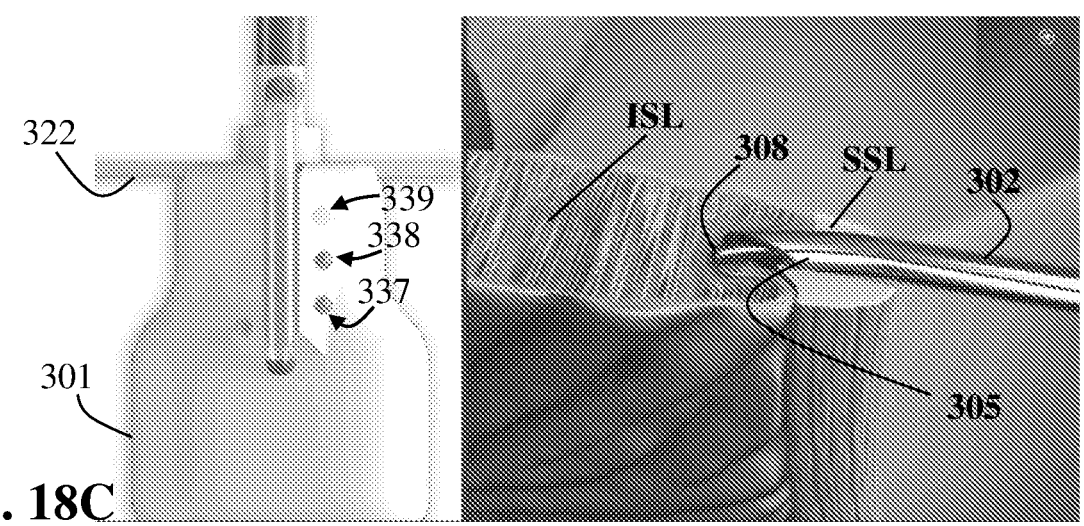

FIG. 18C shows a third instance where cannula distal end 305 is located within interspinous ligament ISL following penetration thereto across supraspinous ligament SSL. First one or several cycles of protrusions in interspinous ligament ISL are used for measuring resistance applied by this body tissue mass against distal progression of pusher-probe distal end 308, which is known to be greater than resistance applied by supraspinous ligament SSL During this period, both first LED 337 and second LED 338 are active as shown.

FIG. 18D shows another instance where cannula distal end 305 is in interspinous ligament ISL yet in proximity to ligamentum flavum LF, so although resistance may be different (known to be greater) than in previous instance shown in FIG. 18C, still it is preset within same range of resistances so only first LED 337 and second LED 338 are kept active.

FIG. 18E shows a fifth instance where cannula distal end 305 is located within ligamentum flavum LF following penetration thereto across interspinous ligament ISL. First one or several cycles of protrusions in ligamentum flavum LF are used for measuring resistance applied by this body tissue mass against distal progression of pusher-probe distal end 308, which is known to be greater than resistance applied by interspinous ligament ISL. During this period, all three LEDs 337, 338 and 339, are active as shown.

FIG. 18F shows a sixth instance where cannula distal end 305 is located within epidural space ES following penetration thereto across ligamentum flavum LF. An immediate fall of resistance applied to pusher-probe distal end 308 relative to resistance previously applied by ligamentum flavum LF. During this period, all three LEDs 337, 338 and 339, are active and blink. Once it is recognized that cannula distal end 305 is at the target location, the advancing is ceased on order to prevent undesired penetration to dura mater DM. In some embodiments, system 300 is configured such that immediately upon immediate fall of resistance applied to pusher-probe distal end 308 relative to resistance previously applied by ligamentum flavum LF, or immediately upon recognizing presence of cannula distal end 305 at the target location/epidural space ES, pusher-probe distal end 308 maintains a protruding position relative to sharp edge 306 so as to prevent further penetration into the dura mater DM. These operations or procedures may be performed, for example, via using a dedicated code or program in microprocessor 332 and by proximity sensor measurements 330.

Figure 18G:
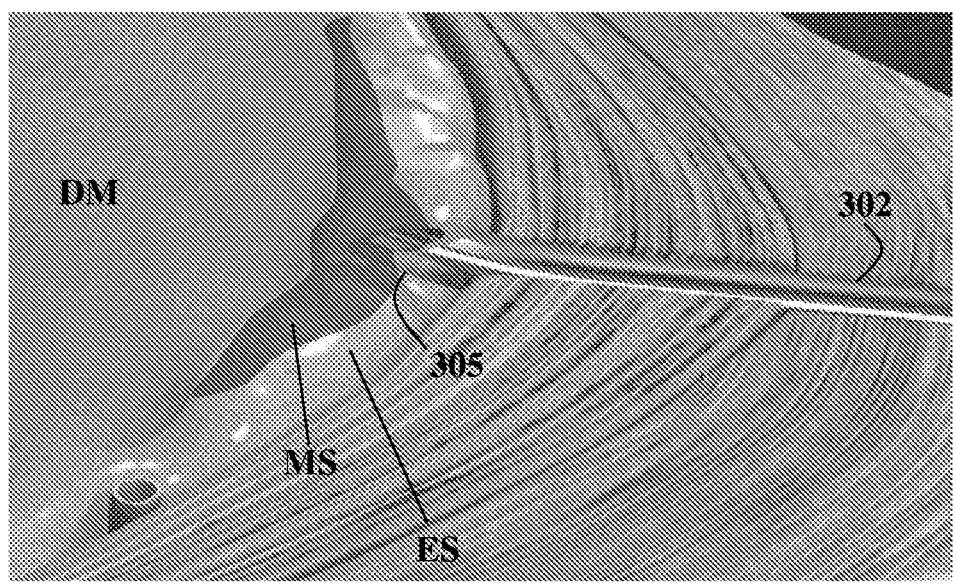

In some embodiments, as a possible safety measure, syringe 303 may be applied for performing of a loss of resistance (LOR) technique in subacromial space SAS. Once it is finally determined, that cannula distal end 305 is in the target location, namely, in this particular exemplary embodiment, in epidural space ES, syringe 303 or a different syringe can be applied for delivering a medicinal substance MS there, via cannula lumen 304, as shown in FIG. 18G. Optionally, pusher-probe 307 is removed from cannula lumen 304 prior to delivering medicinal substance MS to epidural space ES.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at east one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

The phrase 'operatively connected', as used herein, equivalently refers to the corresponding synonymous phrases 'operatively joined', and 'operatively attached', where the operative connection, operative joint, or operative attachment, is according to a physical, or/and electrical, or/and electronic, or/and mechanical, or/and electro-mechanical, manner or nature, involving various types and kinds of hardware or/and software equipment and components.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for identifying a target anatomic location penetrated by a medical device distal tip following transtissual progression thereof through a body tissue mass, the system comprising:
   a cannular member enclosing a cannula lumen open at a cannula distal end having a sharp edge;

a pusher-probe having a pusher-probe distal end provided in said cannula lumen, said pusher-probe distal end is positionable from a retracted position, being enclosed within said cannula lumen, to a protruding position, in which said pusher-probe distal end protrudes out of said cannula distal end to a length in a range of between a minimal protrusion length and a maximal protrusion length; and an actuation mechanism adapted to actuate repeated protrusions of said pusher-probe distal end relative to said cannula distal end including continuous cycles of a protrusion of said pusher-probe distal end relative to said cannula distal end followed by an immediate retraction of said pusher-probe distal end when under a retractive force.

2. The system of claim 1, wherein said actuation mechanism includes an extending mechanism comprising a cam member, and a follower shiftable from a first station to a second station on said cam member, wherein said follower is configured for applying forces to said pusher-probe thereby effecting change in position of said pusher-probe distal end relative to said cannula distal end, in accordance with distance of said follower from rotation center of said cam member or/and with resistance to said pusher-probe by incoming body tissue mass.

3. The system according to claim 2, wherein said pusher-probe distal end is configured for remaining in said retracted position, when said follower rests in said first station, and wherein said pusher-probe distal end is configured for remaining in said minimal protrusion length, when said follower rests in said second station.

4. The system according to claim 2, wherein said extending mechanism includes a measuring spring between said follower and said pusher-probe configured to change in length between a first length and a second length related to a difference between an activating force applied thereto by said follower and an opposing resistive force applied thereto by said pusher-probe.

5. The system according to claim 4, wherein said extending mechanism is configured such that a length or a change in length of said measuring spring correlate with a mechanical property of the body tissue mass.

6. The system according to claim 4, wherein said resistive force equals said resistance to said pusher-probe by said incoming body tissue mass.

7. The system according to claim 4, wherein said measuring spring is connected to a marking flag provided between said measuring spring and said pusher-probe, said marking flag is movable with motions of said pusher-probe relative to a stationary proximity sensor, applicable to measuring distance to said marking flag, between a predetermined range of distances, therefrom, and wherein said range of distances is between 0 and 7 mm.

8. The system according to claim 7, wherein a complete single rotation cycle of said cam member around said rotation center thereof affects an activation cycle of said pusher-probe, including a single protrusion maneuver followed by a single retraction of said pusher probe distal end, wherein said system is configured such that said activation cycle includes an effective measuring period being equal to, or shorter in duration than, the entire cycle duration, said effective measuring period corresponds with said proximity sensor measuring particularly of distances within said range of distances.

9. The system according to claim 8, wherein said effective measuring period is determined by at least one of: any continuous period in which said measuring spring is stressed, any continuous period in which said marking flag is distanced away from said proximity sensor by no more than a predetermined value or/and by about 4 mm or less, and by relative positioning of said cam member.

10. The system according to claim 1, wherein said pusher-probe is noncompliant and rigid relative to the body tissue mass when provided at least partially within said cannula.

11. The system according to claim 1, wherein said pusher-probe distal end is configured to mechanically manipulate a portion of the body tissue mass, via thrusting into and then releasing contact with said portion of the body tissue mass, during repositioning of said pusher-probe distal end to said retracted position or/and to said protruding position.

12. The system according to claim 1, further comprising a sensor adapted to correlate a mechanical property of the body tissue mass with a sensed affect resulting from the body tissue mass reacting to mechanical manipulation.

13. The system according to claim 12, further comprising a data-information analyzing device including an integrated circuit or/and a data-information processing/programming unit programmed to assign a numerical value to said sensed affect.

14. The system according to claim 13, wherein said data-information analyzing device comprises a memory, wherein said data-information processing/programming unit is programmed to store a database of previous numerical values assigned to previous sensed affects or/and other stored information, and to compare said numerical value of said sensed affect to said previous numerical values of said database.

15. The system according to claim 13, further comprising a trigger mechanism comprised of:
a winged hub member including a hub body coupled with at least one wing-like flange sized and shaped for effective finger pressing thereto, said hub body is slidably connected via a structural portion of the system proximally to said cannular member and slidable from a first hub position to a second hub position distal to said first hub position.

16. The system according to claim 15, wherein said trigger mechanism comprises a hub retracting mechanism configured for resisting motion of said winged hub member away from said first hub position.

17. The system according to claim 16, wherein said hub retracting mechanism is configured for allowing motion only when pressed distally with a force greater than a predetermined threshold force.

18. The system according to claim 16, wherein said hub retracting mechanism is configured for retracting said winged hub member relative to said structural portion of the system after reaching said second hub position or/and when pressed distally with a force less than said predetermined threshold force.

19. The system according to claim 15, further comprising a hub locator configured for signaling to said data-information analyzing device a predetermined signal corresponding to at least one of a location of said winged hub member at said second hub position and a location of said winged hub member away from said first hub position, for at least 0.3 second;
wherein said data-information analyzing device is programmed to assign said numerical value to said sensed affect, or/and to indicate proximity of, or positioning in, a target anatomic location, only upon or while receiving said predetermined signal from said hub locator.

20. The system according to claim 13, comprising a signifying device linked with at least one of said data-information analyzing device and said sensor, and including at least one of a visual signaling unit and an audio signaling unit.

21. The system according to claim 1, wherein said pusher-probe distal end is sized or/and shaped so as to prevent penetration thereof into the body tissue mass during repositioning.

22. The system according to claim 1, wherein said pusher-probe is configured such that fluid travels thereacross or/and therethrough when in said retracted position or/and when in said protruding position.

23. The system according to claim 1, wherein said maximal protrusion length is equal to or less than about 5 mm.

24. The system according to claim 1, wherein distance of said pusher-probe distal end to said cannula distal end in said protruding position is determined according to a mechanical property of the body tissue mass, and wherein said distance is in a range of between about 0.2 mm and about 5 mm.

25. The system according to claim 1, wherein said pusher-probe distal end is configured to non-traumatically mechanically manipulate the body tissue mass by at least one of laterally stretching, distally compressing, distally curving, distally bending, distally pushing, and rotationally twisting, the body tissue mass, or/and by at least partially immersing in the body tissue mass.

26. The system according to claim 1, further comprising a coupling to a loss of resistance (LOR) type syringe or/and wherein said cannular member includes or is in a form of an epidural needle.

27. The system according to claim 1, wherein said actuation mechanism is adapted for automatic reciprocal repositioning of said pusher-probe distal end between said retracted position and said protruding position during a defined actuation period.

28. The system according to claim 1, wherein said actuation mechanism includes a motion source for providing continuous reciprocal repositioning to said pusher-probe distal end relative to said cannula distal end.

29. The system according to claim 28, wherein said reciprocal repositioning includes a plurality of stroke cycles, each comprising a single forward stroke from said retracted position to said protruding position, and a single backward retraction from said protruding position to said retracted position, wherein said stroke cycles have a frequency in a range of between about 0.5 Hz and about 10 Hz.

30. The system according to claim 28, wherein said reciprocal repositioning facilitates unhindered transtissual progression of the medical device tip through soft tissue with a progression velocity equal to or less than about 5 mm per second.

* * * * *